US009752187B2

(12) United States Patent
Wasserstrom et al.

(10) Patent No.: US 9,752,187 B2
(45) Date of Patent: *Sep. 5, 2017

(54) CATEGORIZATION OF DNA SAMPLES

(75) Inventors: Adam Wasserstrom, Nes-Ziona (IL);
Danny Frumkin, Rehovot (IL)

(73) Assignee: Nucleix, Herzelya (IL)

( * ) Notice: Subject to any disclaimer, the term of this patent is extended or adjusted under 35 U.S.C. 154(b) by 69 days.

This patent is subject to a terminal disclaimer.

(21) Appl. No.: 13/492,187

(22) Filed: Jun. 8, 2012

(65) Prior Publication Data

US 2013/0078626 A1   Mar. 28, 2013

Related U.S. Application Data

(63) Continuation-in-part of application No. PCT/IB2010/003397, filed on Dec. 8, 2010, and a continuation-in-part of application No. PCT/IB2011/000300, filed on Feb. 17, 2011, and a continuation-in-part of application No. 13/029,719, filed on Feb. 17, 2011, and a continuation-in-part of application No. PCT/IB2011/000861, filed on Apr. 19, 2011.

(60) Provisional application No. 61/285,758, filed on Dec. 11, 2009, provisional application No. 61/306,201, filed on Feb. 19, 2010, provisional application No. 61/325,977, filed on Apr. 20, 2010.

(51) Int. Cl.
*C12Q 1/68* (2006.01)

(52) U.S. Cl.
CPC ......... *C12Q 1/6876* (2013.01); *C12Q 1/6809* (2013.01); *C12Q 1/6858* (2013.01); *C12Q 1/6881* (2013.01); *C12Q 2600/154* (2013.01)

(58) Field of Classification Search
None
See application file for complete search history.

(56) References Cited

U.S. PATENT DOCUMENTS

| 6,764,822 | B1  |   | 7/2004  | Butler et al. |
|-----------|-----|---|---------|---------------|
| 6,812,339 | B1  | * | 11/2004 | Venter et al. ............. 536/24.31 |
| 2002/0152035 | A1 |   | 10/2002 | Perlin |
| 2004/0181048 | A1 | * | 9/2004  | Wang ........................... 536/24.3 |
| 2005/0153316 | A1 |   | 7/2005  | Jeddeloh et al. |
| 2005/0158739 | A1 | * | 7/2005  | Jeddeloh ................ C12Q 1/683 435/6.12 |
| 2005/0272065 | A1 | * | 12/2005 | Lakey et al. ...................... 435/6 |
| 2007/0178506 | A1 |   | 8/2007  | Martienssen et al. |
| 2007/0202526 | A1 |   | 8/2007  | Nakami et al. |
| 2007/0207195 | A1 |   | 9/2007  | Yarosh |
| 2007/0275402 | A1 | * | 11/2007 | Lo ......................... C12Q 1/6827 435/6.11 |
| 2008/0153099 | A1 | * | 6/2008  | Allen .................. C12Q 1/6851 435/6.12 |
| 2008/0286773 | A1 |   | 11/2008 | Bender |
| 2009/0018031 | A1 |   | 1/2009  | Trinklein et al. |
| 2009/0053706 | A1 |   | 2/2009  | Laird et al. |
| 2009/0305234 | A1 |   | 12/2009 | Olek et al. |
| 2013/0084571 | A1 |   | 4/2013  | Wasserstrom et al. |

FOREIGN PATENT DOCUMENTS

| CA | 2 699 606 A1 | 3/2009 |
|----|--------------|--------|
| EP | 1 213 360 A1 | 6/2002 |
| EP | 1748080 A2   | 1/2007 |
| EP | 2071035      | 6/2009 |
| WO | WO 02/12328 A2 | 2/2002 |
| WO | WO 2005/040399 A2 | 5/2005 |
| WO | 2007/018601  | 2/2007 |
| WO | WO 2007018601 A1 * | 2/2007 |
| WO | WO 2008/104002 A2 | 8/2008 |
| WO | 2008/140532 A1 | 11/2008 |
| WO | WO 2009/083989 A1 | 7/2009 |
| WO | WO 2011/070441 A2 | 6/2011 |
| WO | WO 2012/070037 A2 | 5/2012 |

OTHER PUBLICATIONS

Holemaon, H et al. MethylScreen: DNA methylation density monitoring using quantitative PCR. Biotechniques, vol. 43, No. 5, p. 683-693, 2007.*
Rubin, CM. et al. Alu repeated DNAs are differentially methylated in primate germ cells. Nucleic Acids Research, vol. 22, No. 23, p. 5121-5127, 1994.*
Lowe et al., A computer program for selection of oligonucleotide primers for polymerase chain reactions. Nucleic Acids Research, vol. 18, No. 7, pp. 1757-1761, 1990.*
Zeschnigk, M. et al. IGF2/H19 hypomethylation in silver-russell syndrome and isolated hemihypoplasia. European journal of Human Genetics, vol. 16, p. 328-334, 2008.*
Zhao, G. et al. Study on the application of parent-of-origin specific DNA methylation markers to forensic genetics. Forensic Science International, vol. 154, p. 122-127, 2005.*
Nakayashiki, N. et al. Studies on differentially methylated parental allele in imprinted genes. Forensic Science International: Genetics, Supplement series 1, p. 572-573, 2008.*
The International Search Report received in the related application No. PCT/IB2010/003397, dated Sep. 11, 2012.

(Continued)

*Primary Examiner* — Prabha Chunduru
(74) *Attorney, Agent, or Firm* — Winston & Strawn LLP

(57) ABSTRACT

The present application describes methods for accurate and cost-effective categorization of DNA samples into different types of in vitro generated DNA or different types of natural DNA such as from different tissues and/or physiological/pathological states. The invention achieves categorization by comparing "signal ratios" that are correlated to ratios of methylation levels at specific genomic loci, but does not rely on calculation of actual methylation levels at any genomic locus. Therefore the disclosed inventive method eliminates the requirement for external DNA species and controls, thereby simplifying and increasing the accuracy of the assay. The described inventive technology also enables performing the categorization of DNA together with DNA profiling in the same reaction, thereby allowing for concomitant categorization and determination of identity of the samples.

17 Claims, 16 Drawing Sheets

(56) References Cited

OTHER PUBLICATIONS

Frumkin, et al., "DNA methylation-based forensic tissue identification", *Forensic Science International: Genetics*, 2010, vol. 5, No. 5, pp. 517-524.
The Search Report received in the parent International Application No. PCT/IB2011/000861, dated Jun. 1, 2012.
Frumkin, et al., "Authentication of forensic DNA samples", *Forensic Science International: Genetics, Elsevier BV*, 2010, vol. 4, No. 2, pp. 95-103.
Holeman, H., et al., "MethylScreen: DNA methylation density monitoring using quantitative PCR" *Biotechniques, Informa Healthcare*, 2007, vol. 43, No. 5, pp. 683-693.
U.S. Appl. No. 13/029,719, filed Feb. 17, 2011, Nucleix Ltd.
Yamagata et al., (2009) Aberrant DNA methylation status in human uterine leiomyoma. Mol Hum Reprod 15(4): 259-67.
Eads et al., (2000) MethyLight: a high-throughput assay to measure DNA methylation. Nucleic Acids Res 28(8): E32. Especially p. 3, col. 1, para. 3.
Fantappié et al., (2001) Lack of DNA methylation in Schistosoma mansoni. Exp Parasitol 98(3): 162-6.
Greiner et al. (2002) Effectiveness of capillary electrophoresis using fluorescent-labeled primers in detecting T-cell receptor gamma gene rearrangements. J Mol Diagn 4(3): 137-43. Abstract.
Herman et al., (1996) Methylation-specific PCR: a novel PCR assay for methylation status of CpG islands. Proc Natl Acad Sci U S A 93(18): 9821-6.
Martin-Magniette et al., (2005) Evaluation of the gene-specific dye bias in cDNA microarray experiments. Bioinformatics 21(9): 1995-2000.
Oakes et al., (2006) Evaluation of a quantitative DNA methylation analysis technique using methylation-sensitive/dependent restriction enzymes and real-time PCR. Epigenetics 1(3):146-52.
Sakamoto et al., (2007) Cell type-specific methylation profiles occurring disproportionately in CpG-less regions that delineate developmental similarity. Genes to Cells 12(10): 1123-32.
Touchman et al., Genebank accession No. G54325.1CBS16 Human EGreen *Homo sapiens* STS genomic, sequence tagged site, Aug. 23, 1999 (online). Retrieved on Feb. 20, 2011 (Feb. 20, 2011). Retrieved from the internet: URL: http://www.ncbi.nlm.nih.gov/nuccore/G54325.1.
von Kanel et al., (2010) Quantitative one-step DNA methylation analysis (qOSMA) using native genomic DNA as template (online). Advances in Genomics Jan. 28-29, 2010 (retrieved Nov. 22, 2011), available on the Internet: URL: http://www.advances-ingenomics.org/presentations NonKanel.pdf. Especially pp. 5, 15.
Yagi et al., (2008) DNA methylation profile of tissue-dependent and differentially methylated regions (T-DMRs) in mouse promoter regions demonstrating tissue-specific gene expression. Genome Res 18(12): 1969-78.
Final office action dated Mar. 19, 2015 for copending U.S. Appl. No. 13/029,719.
Hua et al., (2011), "Quantitative methylation analysis of multiple genes using methylation-sensitive restriction enzyme-based quantitative PCR for the detection of hepatocellular carcinoma," Experimental and Molecular Pathology, 91(1):455-60.
Reinert et al., (2011), "Comprehensive Genome Methylation Analysis in Bladder Cancer: Identification and Validation of Novel Methylated Genes and Application of These as Urinary Tumor Markers," Clin Cancer Res, 17(17):5582-92.
*Homo sapiens* KCNJ2 antisense RNA 1 (head to head) (KCNJ2-AS1), long non-coding RNA. Genebank: NR_036534.1, Nov. 5, 2013 (Nov. 5, 2013). URL: https://www.ncbi.nlm.nih.gov/nuccore/303227915; 2 pages.
*Homo sapiens* potassium voltage-gated channel subfamily J member 2 (KCNJ2), RefSeqGene (LRG_328) on chromosome 17.Genebank: NG_008798.1, Feb. 7, 2016 (Feb. 7, 2016). URL: https://www.ncbi.nlm.nih.gov/nucleotide/209969779?report=genbank&log$=nuclalign&blast_rank=2&RID=VV2JJWYR01R; 6 pages.
Nouzova et al., (2004) Epigenomic changes during leukemia cell differentiation: analysis of histone acetylation and cytosine methylation using CpG island microarrays. J Pharmacol Exp Ther 311(3): 968-81.

* cited by examiner

Figure1A-B
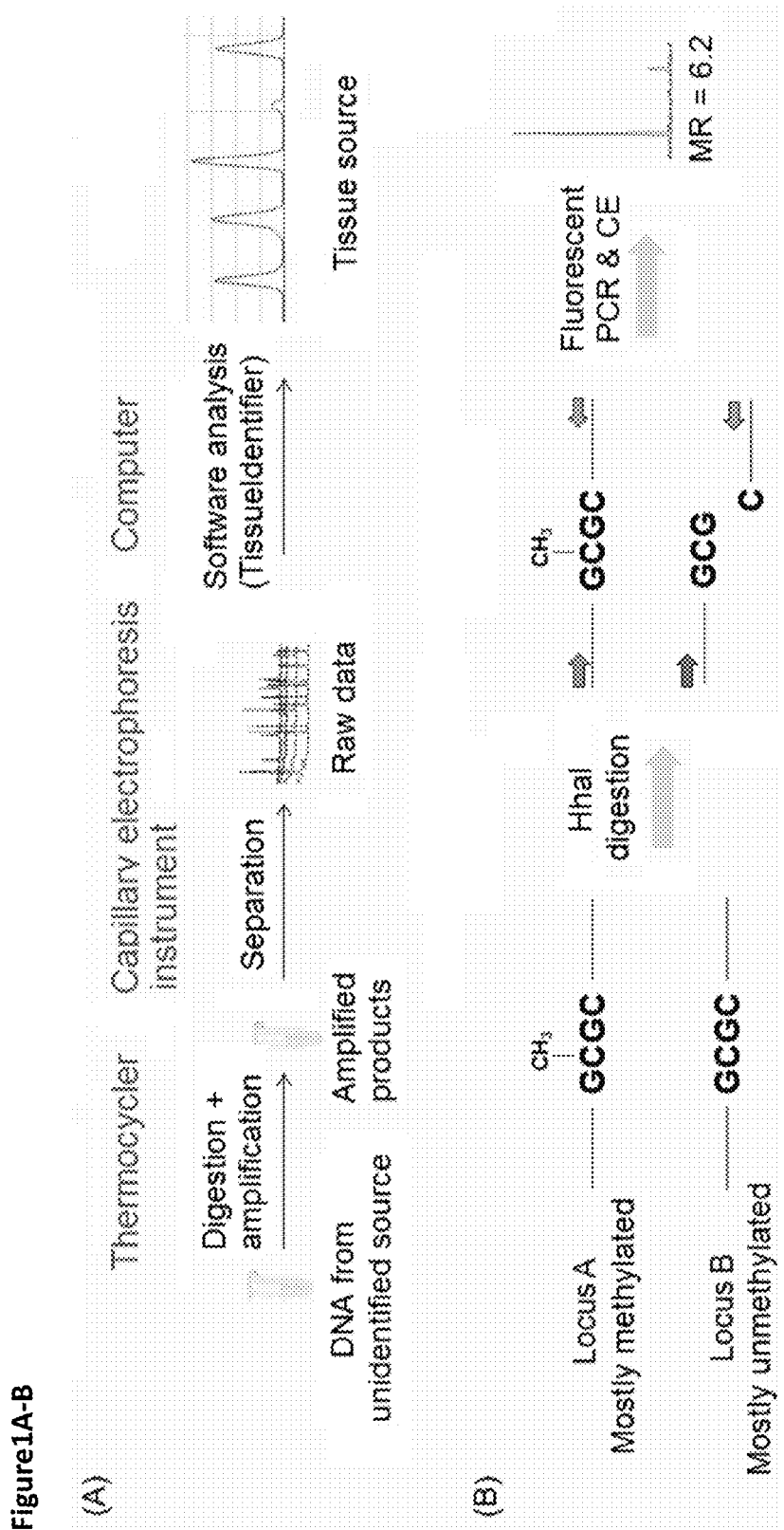

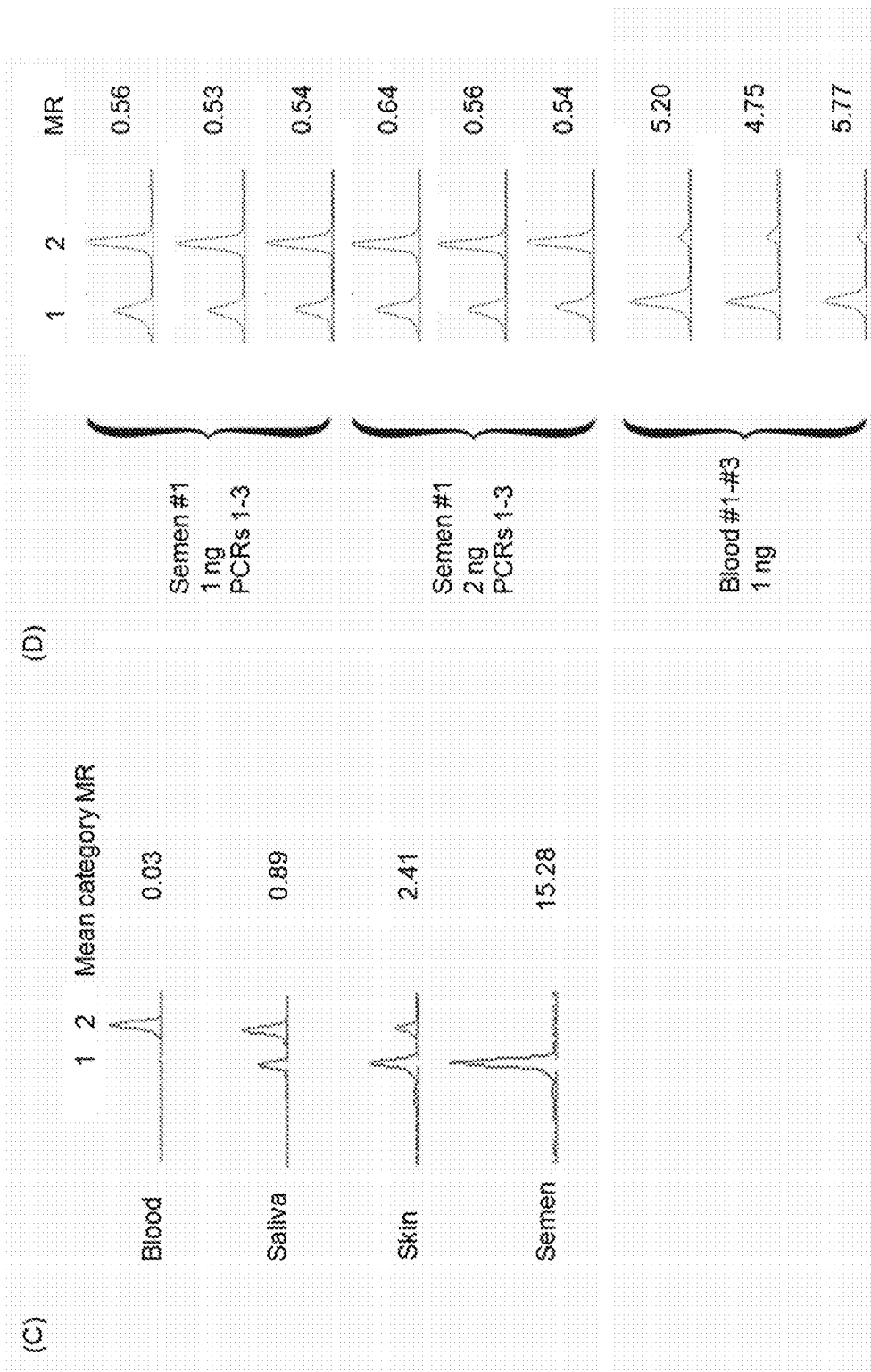
Figure 1C-D

Figure 6
DNAseI-treated blood sample
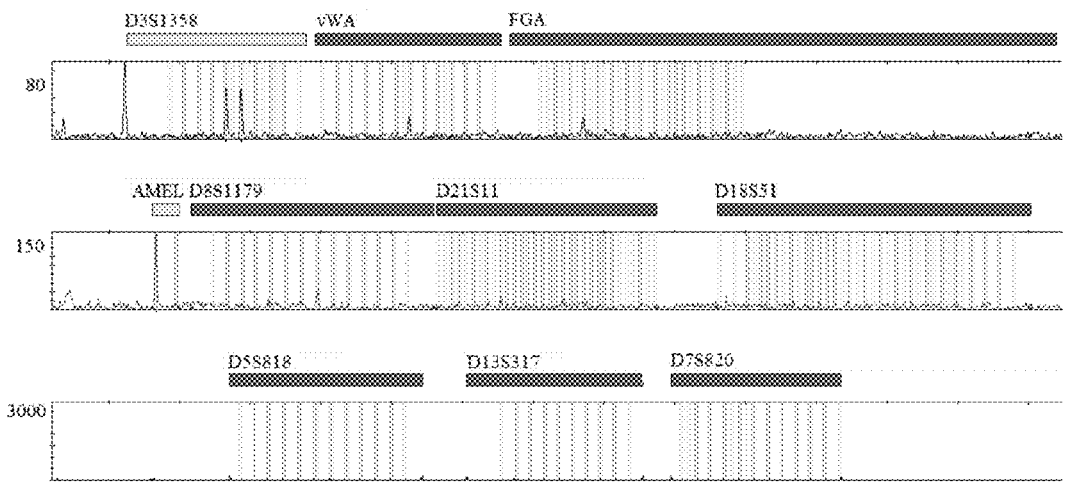
DNAseI-treated semen sample
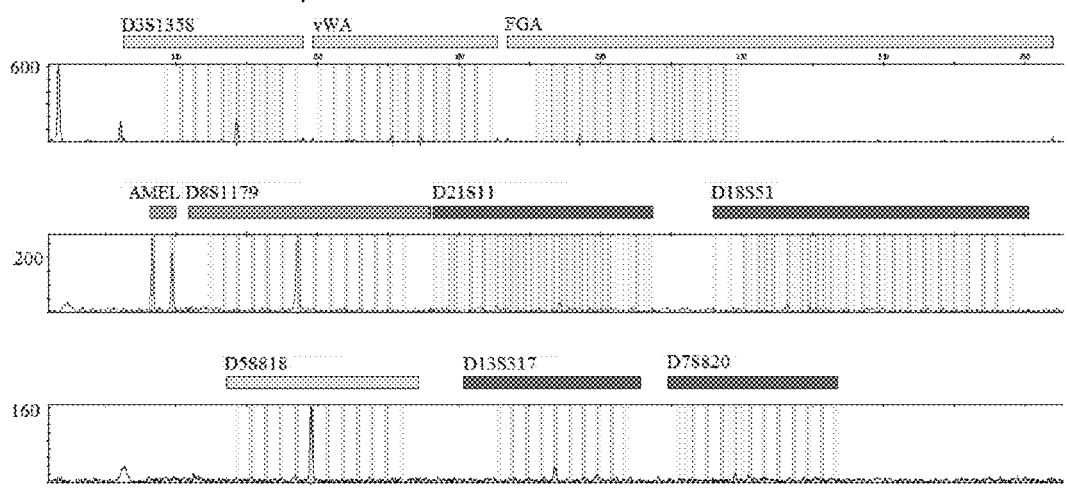

Figure 7

Table 1 – Panel of loci used for tissue identification assay

| # | Locus | Location[a] | Forward primer | SEQ ID NO. | Reverse primer | SEQ ID NO. | Size[b] | Conc.[c] |
|---|---|---|---|---|---|---|---|---|
| 1 | L91762 | Chr12 (73985697) | GCAGCAGGCCGCGGAGAAG (FAM) | 67 | AGCAGCTGTGCCGGGCCAG | 82 | 66 | 0.2µM |
| 2 | L68346 | Chr3 (12175317) | CAGCAACAGCACCCAGCTTG (JOE) | 68 | CACAGGCTCAGTCGCGGATC | 83 | 70 | 0.2µM |
| 3 | L50468 | Chr3 (55492965) | AGGAAACCTCAGTAGCAAAATTG (JOE) | 69 | GCCAGAGACTTTAGGTGTGCATC | 84 | 75 | 0.2µM |
| 4 | L14432 | Chr22 (29861149) | CGTAGGCTGCGGTGAGCTC (FAM) | 70 | GATCCATGCCCGCTGGGATG | 85 | 75 | 0.2µM |
| 5 | L4648 | Chr1 (35815331) | CAGCCTAGACGTCAAGTTACACAG (JOE) | 71 | ACGACCTCCGGATCCAACTG | 86 | 80 | 0.2µM |
| 6 | L39664 | Chr17 (53710330) | CCCAGCTGGTTGGACATGTTG (FAM) | 72 | CACTTCCTTCGTGGACGCC | 87 | 82 | 0.2µM |
| 7 | L30139 | Chr17 (36996489) | GAGAAGCGGGAGGATGAGAC (FAM) | 73 | CCCGCATCTCCTCCGTCCTG | 88 | 84 | 0.2µM |
| 8 | L55429 | Chr5 (1548043) | GCCTTCAGCAGGAAGTCCAC (JOE) | 74 | CCTGTGCCTCACACAGACTC | 89 | 88 | 0.2µM |
| 9 | L62086 | Chr19 (40478538) | GTGCATGGTGTCTGGTACTTC (FAM) | 75 | GAAGCTCTCGTGGACTACTTG | 90 | 89 | 0.1µM |
| 10 | L76138 | Chr19 (3130217) | CAGCCTGCTCTTCACTGCAG (JOE) | 76 | AGAGGCCGATGAAGCCGTAG | 91 | 100 | 0.2µM |
| 11 | L15952 | Chr7 (2741305) | CTCCCTGATTTACGACAAGTTC (FAM) | 77 | GACAGTATGCTGATGCTTCTTG | 92 | 117 | 0.2µM |
| 12 | L36599 | Chr19 (4867642) | AAGGGCAGAGTTCCGCTGTC (FAM) | 78 | CGGATGCAGGAGGATCCTAG | 93 | 130 | 0.2µM |
| 13 | L26688 | Chr17 (77844826) | CGGACCAGATTGCTGGTCAC (JOE) | 79 | CGACCTTGCCAGATGTTTGAC | 94 | 134 | 0.2µM |
| 14 | L81528 | Chr19 (47395603) | AGCCTCATCCACACTGACCAG (JOE) | 80 | TCAGAGCTCTCCTATCTGGAC | 95 | 141 | 0.2µM |
| 15 | L36556 | Chr19 (50962118) | GCCAGGCCGTTGATGATGAC (JOE) | 81 | GAATATGGAGCCCTGGGCAG | 96 | 149 | 0.3µM |

[a] Genomic location of the examined CG according to UCSC version hg18 is provided in brackets following the chromosome number

[b] in bps

[c] The concentration refers to both the forward and reverse primers

Table 2. Signal ratios of L91762/L68346 and L76138/L26688

| | L91762/L68346 | | L76138/L26688 | |
|---|---|---|---|---|
| | mean±std | range | mean±std | range |
| Semen | 0.16±0.14 | 0.04-0.53 | 6.50±5.80 | 2.04-19.00 |
| Blood | 4.36±1.69 | 2.15-7.73 | 0.30±0.20 | 0.08-0.76 |
| Saliva | 7.10±3.30 | 3.36-15.38 | 0.56±0.41 | 0.16-1.54 |
| Skin epidermis | 11.40±4.20 | 4.60-18.28 | 8.41±5.58 | 2.1-19.56 |

Table 3. Loci used for assessing HhaI digestion

| Location* | Forward primer | SEQ ID NO. | Reverse primer | SEQ ID NO. | Size (bp) |
|---|---|---|---|---|---|
| Chr7 (141084738) | GCGAAGGAAGTGCTGGAGTC (FAM) | 97 | GTTTCTTGAAAGGGCCAGACAC | 99 | 94 |
| Chr11 (86241803) | CAAAGTACTGGGGTTACAGGTG (FAM) | 98 | GGATGAACCTTTAAGACATCATC | 100 | 97 |

* Genomic location of the examined CG according to UCSC version hg18 is provided in brackets following the chromosome number (in locus L98328, which does not have a HhaI recognition site, the location is of the beginning of the forward primer)

Figure 10

Table 4. Panel of loci used for semen detection

| Locus | Location[a] | Forward primer | SEQ ID NO. | Reverse primer | SEQ ID NO. | Size[b] | Conc.[c] |
|---|---|---|---|---|---|---|---|
| L68346 | Chr3 (12175317) | CAGCAACAGCACCCAGCTTG (FAM) | 101 | CACAGGCTCAGTCGCGGATC | 103 | 70 | 0.2μM |
| L16264 | Chr2 (2734005) | GGACGAGTTAACTTCCTTAATTTC (FAM) | 102 | GTTTCTTCGCGGAACCTGGTTTAACTTC | 104 | 95 | 0.2μM |

[a] Genomic location of the examined CG according to UCSC version hg18 is provided in brackets following the chromosome number

[b] in bps

[c] The concentration refers to both the forward and reverse primers

Figure 11

Table 5. Detection and quantification of semen component in semen-saliva mixtures

| Sample number | % semen in sample (according to STR typing) | % semen in sample (according to our assay) | Semen detected? |
|---|---|---|---|
| 1 | 100 | 100 | Yes |
| 2 | 100 | 100 | Yes |
| 3 | 100 | 100 | Yes |
| 4 | 76 | 66 | Yes |
| 5 | 57 | 47 | Yes |
| 6 | 30 | 23 | Yes |
| 7 | 16 | 15 | Yes |
| 8 | 0 | 0 | No |
| 9 | 0 | 0 | No |
| 10 | 0 | 0 | No |

Each row represents a single reaction

CATEGORIZATION OF DNA SAMPLES

CROSS-REFERENCE TO RELATED PATENT APPLICATIONS

This application is a Continuation-In-Part of International Patent Application PCT/IB2010/003397, filed Dec. 8, 2010, which claims priority to U.S. Provisional Application 61/285,758 filed on Dec. 11, 2009, and Continuation-In-Part of International Patent Application No.: PCT/IB2011/000861, filed Apr. 19, 2011, which claims priority to U.S. Provisional Application 61/325,977, filed Apr. 20, 2010, and Continuation-In-Part of International Patent Application PCT/IB2011/000300 and U.S. patent application Ser. No. 13/029,719, both filed Feb. 17, 2011 and both claiming priority to U.S. Provisional Patent Application 61/306,201, filed Feb. 19, 2010, which are all incorporated herein by reference in their entirety.

BACKGROUND OF THE INVENTION

Field of the Invention

The present inventive technology relates to methods for accurate and cost-effective categorization and profiling of DNA samples to identify the originating source and identity of the DNA sample or mixed DNA samples.

SUMMARY OF THE INVENTION

The present invention relates to methods for accurate and cost-effective categorization of DNA samples into different types of in vitro generated DNA or different types of natural DNA such as from different tissues and/or physiological/pathological states. The invention achieves categorization by comparing "signal ratios" that are correlated to ratios of methylation levels at specific genomic loci, but does not rely on calculation of actual methylation levels at any genomic locus. Therefore the invention setup eliminates the requirement for external DNA species and/or controls, thereby both simplifying and increasing the accuracy of the assay. The inventive technology also enables performing the categorization of DNA together with DNA profiling in the same reaction, thereby allowing for concomitant categorization and determination of identity of the samples.

One aspect of the present invention is a method for categorization of a DNA sample, the method comprising:
(A) digesting a DNA sample with a methylation-sensitive and/or methylation-dependent restriction endonuclease;
(B) performing PCR on the digested DNA amplifying at least two genomic loci of which at least one is a restriction locus;
(C) determining the intensity of the signal of each amplification product;
(D) calculating "signal ratios" between the intensities of the signals produced by the loci; and
(E) comparing the signal ratios to reference values corresponding to different categories of DNA, wherein the category whose reference values correspond best to the signal ratios is determined to be the category of the DNA sample. That is, for instance, the approximation of the value of a signal ratio to the value of a reference value of a particular DNA category indicates the categorical source of the DNA sample. So if a signal ratio that has a value that is close to the value of a reference category, then the likelihood that the tested DNA sample originated from that particular type of category—based on the similarity in values between the signal ratio and the reference value—is high. Thus, the signal ratio(s) that best correspond to, or best approximate, a particular reference value(s) for a particular DNA category makes it likely that that DNA sample originated from that particular DNA categorical source. For examples about how to compare the signal ratios and category reference values see the disclosure elsewhere in this application, such as in the section entitled Algorithm and Software, which explains how to calculate probability distributions and likelihood probalities that a test DNA sample can be categorized to one or more reference categories.

In one embodiment, DNA digestion and PCR are performed in a single biochemical reaction in which the DNA template, digestion and amplification enzymes, buffers, primers, and accessory ingredients are placed together in a test tube and then the test tube is closed and placed in a thermal cycler, where the reaction takes place.

In one embodiment, the methylation-sensitive restriction endonuclease is unable to cut or digest a DNA if its recognition sequence is methylated. In one embodiment, a methylation-sensitive restriction endonuclease is selected from the group consisting of AatII, Acc65I, AccI, AciI, ACII, AfeI, AgeI, ApaI, ApaLI, AscI, AsiSI, AvaI, AvaII, BaeI, BanI, BbeI, BceAI, BcgI, BfuCI, BglI, BmgBI, BsaAI, BsaBI, BsaHI, BsaI, BseYI, BsiEI, BsiWI, BsII, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, EagI-HF, EciI, EcoRI, EcoRI-HF, FauI, Fnu4HI, FseI, FspI, HaeII, HgaI, HhaI, HincII, HincII, HinfI, HinP1I, HpaI, HpaII, Hpy166ii, Hpy188iii, Hpy99I, HpyCH4IV, KasI, MluI, MmeI, MspA1I, MwoI, NaeI, NacI, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, PshAI, PspOMI, PvuI, RsaI, RsrII, SacII, SaII, SaII-HF, Sau3AI, Sau96I, ScrFI, SfiI, SfoI, SgrAI, SmaI, SnaBI, TfiI, TscI, TseI, TspMI, and ZraI.

In another embodiment, a methylation dependent restriction enzyme can be used to digest a DNA sample. A methylation dependent restriction endonuclease digests only methylated DNA. Examples of such restriction enzymes include but are not limited to McrBC, McrA, and MrrA.

In one embodiment, at least one restriction locus is known to be methylated in natural DNA.

In another embodiment, at least one restriction locus is known to be unmethylated in natural DNA In another embodiment, at least two restriction loci are known to be differentially methylated in natural DNA.

In another embodiment, the signal ratio between at least two loci is known to be different for at least two potential categories.

In another embodiment, primer pairs used to amplify loci are selected to amplify the core short tandem repeat (STR) loci identified in the Federal Bureau of Investigation's Combined DNA Index System (CODIS).

In one embodiment, the CODIS loci are human genomic loci selected from the group consisting of D16S539 (SEQ ID NO. 1), D7S820 (SEQ ID NO. 2), D13S317 (SEQ ID NO. 3), D5S818 (SEQ ID NO. 4), CSF1PO (SEQ ID NO. 5), TPOX (SEQ ID NO. 6), TH01 (SEQ ID NO. 7), vWA (SEQ ID NO. 8), FGA (SEQ ID NO. 9), D21S11 (SEQ ID NO. 10), D8S1179 (SEQ ID NO. 11), D18S51 (SEQ ID NO. 12), and D3S1358 (SEQ ID NO. 13).

In a particular embodiment, the forward and reverse primers of a restriction and/or profile locus are designed to anneal to SEQ ID NO. 1, 2, 3, 4, 5, 6, 7, 8, 9, 10, 11, 12, 13, 14, 15, 16, 17, 18, 19, 20, 21, 22, 23, 24, or 25.

In one embodiment, the forward and reverse primers of a locus are available in a Promega Corporation commercial kit selected from the group consisting of PowerPlex® 16 HS (Cat.# DC2100, DC2101), PowerPlex® 16 (Cat.# DC6530, DC6531), PowerPlex® 2.1 (Cat.# DC6470, DC6471), PowerPlex® 16 BIO (Cat.# DC6540, DC6541), and PowerPlex® ES Systems (Cat.# DC6730, DC6731).

In one embodiment, the forward and reverse primers of a locus are available in an Applied Biosystems/Life commercial kit selected from the group consisting of SGM, SGM+, AmpFlSTR Identifiler, AmpFlSTR Profiler, AmpFlSTR ProfilerPlus, AmpFlSTR ProfilerPlusID, AmpFlSTR SEfiler, AmpFlSTR SEfiler Plus, AmpFlSTR Cofiler, AmpFlSTR Identifiler Direct, AmpFlSTR Identifiler Plus, AmpFlSTR NGM, AmpFlSTR Y-filer, AmpFlSTR Minifiler.

In one embodiment, the forward and reverse primers of a locus are available in a Qiagen commercial kit selected from the group consisting of Investigator ESSPlex, Investigator ESSPlex SE, Investigator Nonaplex ESSPlex, Investigator Hexaplex ESSPlex, Investigator Triplex AFS QS, Investigator Triplex DSF, Investigator IDplex, Investigator Decaplex SE, Investigator HDplex, Investigator Argus X-12, Investigator Y-12 QS, Investigator DIPplex.

In another embodiment, the restriction loci contain a HpaII recognition sequence and are selected from the group consisting of ADD6, ADD10, ADD17 (SEQ ID NOs. 26-28) and Hypo23, Hypo28, Hypo33 (SEQ ID NOs. 29-31). In one embodiment, the DNA sample is mammalian DNA or plant DNA. In one embodiment, the mammalian DNA is DNA from a mammal selected from the group consisting of human, ape, monkey, rat, mouse, rabbit, cow, pig, sheep, and horse. In a particular embodiment, the mammalian DNA is human DNA. In one embodiment, the human DNA is from a male. In another embodiment, the human DNA is from a female.

In one embodiment, the human DNA sample is obtained from a male or female who has a disorder characterized by abnormal DNA methylation. In one embodiment, the disorder is a neurodevelopmental disorder of ICF (immunodeficiency, centromeric instability, and facial anomalies), Rett syndrome, and fragile X syndrome.

In one embodiment, the plant DNA is DNA from a plant. In one embodiment, the plant is a monocotyledonous plant selected from the group consisting of wheat, turf grass, cereal, maize, rice, oat, barley, sorghum, orchid, iris, lily, onion, banana, sugarcane, sorghum, and palm. In another embodiment, the plant is a dicotyledonous plant selected from the group consisting of avocado, potato, tobacco, tomato, sugarbeet, broccoli, cassava, sweet potato, pepper, cotton, poinsettia, legumes, alfalfa, soybean, carrot, strawberry, lettuce, oak, maple, walnut, rose, mint, squash, daisy, and cactus.

In one embodiment of the method, at least two loci are amplified by PCR with fluorescently labeled primers and wherein pairwise comparisons of the intensity of the fluorescent signals corresponding to the loci is performed in order to calculate signal ratios for each pair of loci.

In one embodiment, primer pairs are used to amplify pairs of loci selected from the group of pairs consisting of D3S1358/D18S51, D3S1358/D7S820, D3S1358/Penta_D, D3S1358/TPOX, D3S1358/FGA, TH01/Penta_D, D21S11/D7S820, D21S11/D18S51, D21S11/Penta_D, D21S11/AMEL, D21S11/TPOX, D21S11/FGA, D5S818/D18S51, vWA/D18S51, D5S818/Penta_E, vWA/Penta_E, D5S818/D7S820, D5S818/Penta_D, D5S818/TPOX, D5S818/FGA, D13S317/D7S820, D13S317/Penta_D, D13S317/TPOX, D13S317/FGA, D16S539/D7S820, CSF1PO/D7S820, vWA/D7S820, D8S1179/D7S820, D16S539/TPOX, D16S539/FGA, CSF1PO/Penta_D, CSF1PO/TPOX, vWA/Penta_D, AMEL/TPOX, AMEL/FGA, vWA/D8S1179, vWA/TPOX, vWA/FGA, D8S1179/TPOX, D8S1179/FGA.

In another embodiment, the restriction loci amplicons are smaller than the smallest amplicons used in DNA profiling, which is about 100 bps in size.

In one aspect of the present inventive technology, quantification of amplicon signals is performed and not necessarily the quantification of the amount of DNA templates. By calculating ratios of amplicon signals, no standard curve or reference DNA is needed since it is unnecessary to calculate actual DNA concentrations. In this embodiment, the ratios of amplicon signals is calculated. The signals may be signals detected from any kind of labeling used for detecting PCR amplification products, such as, but not limited to, ethidium bromide staining, sybr green staining, silver staining, or by fluorescence.

With respect to the latter, in one embodiment, the PCR reaction is performed with fluorescently labeled primers, and determination of the intensity of the signals of the amplification products is achieved by separation of products by capillary electrophoresis and quantification of fluorescence signals.

In another embodiment, the PCR is real time PCR, and determination of the intensity of the signals of the amplification products is achieved by quantification of fluorescence signals.

In a particular embodiment, the methylation-sensitive restriction endonuclease is HhaI.

In a particular embodiment, the methylation-sensitive restriction endonuclease is HhaI and the first restriction locus is the TPOX locus.

In a particular embodiment, the methylation-sensitive restriction endonuclease is HhaI and the first restriction locus is the FGA locus.

In a particular embodiment in which categorization is according to semen or non-semen, the methylation-sensitive restriction endonuclease is HhaI, the restriction loci are SD1, SD2, SD3, and SD4 (SEQ ID NOs. 33-36), a digested control locus is SD5 (SEQ ID NO. 37), and an undigested control locus is SD6 (SEQ ID NO. 38).

In a particular embodiment in which categorization is according to blood, saliva, semen, or skin epidermis, the methylation-sensitive restriction endonuclease is HhaI and the restriction loci are SEQ ID NOs. 39-53.

In a particular embodiment in which categorization is performed together with DNA profiling, and is according to semen or non-semen, the methylation-sensitive restriction endonuclease is HhaI, and the restriction loci are SEQ ID NO. 40 and SEQ ID NO. 54.

In one embodiment, a pair of loci are selected from loci with known methylation levels in at least two DNA categories, such that one of the loci in the pair is known to have a higher methylation level than the second locus in that pair in one DNA category but not in the other.

In another embodiment, a pair of loci are selected without knowledge of methylation levels as follows: select a pair of random genomic loci; design fluorescently labeled primers for amplifying each locus; amplify both loci in DNA samples obtained from different categories; separate amplicons with capillary electrophoresis; calculate signal ratios in the different DNA samples; if ratios calculated from samples corresponding to at least one category are significantly different (e.g. as determined by the Kolmogorov-Smirnov test with a threshold of p=0.05) than those obtained from samples corresponding to at least one other category, select the pair for use in assay. In one embodiment, the calculated ratios are compared to a set of ratios obtained from natural samples and to a set of ratios obtained from artificial samples.

With respect to the latter, in one embodiment, the respective mean signal ratios of natural and artificial DNA samples digested with HhaI for specific pairs of loci determined herein are shown below.

|  | Natural DNA | Artificial DNA |
|---|---|---|
| FGA(PowerPlex16)/Hypo12 | 10.3 | 0.89 |
| FGA(PowerPlex16)/Hypo28 | 12.4 | 0.76 |
| TPDX(PowerPlex16)/Hypo12 | 9.7 | 1.12 |

In another embodiment, the calculated ratios are compared to a set of ratios obtained from DNA samples extracted from different tissue categories. See Tables 1-4 presented in FIGS. 7-10 for additional examples of loci sequences and illustrative signal ratios and results used and obtained in accordance with the inventive categorization methods disclosed herein.

In one embodiment this method, or any method described herein, further comprises simultaneously profiling a DNA sample and determining whether the category of the DNA. In one embodiment, the step of profiling a DNA sample is performed according to instructions provided in a commercially available DNA profiling kit. In another embodiment, the commercially available DNA profiling kit is the PowerPlex®16 profiling kit (Promega Corporation).

In one embodiment, with respect to the latter, categorization of DNA is according to tissue types. Any tissue type can be used such as, but not limited to blood, saliva, semen, epidermis, urine, plasma, and hair.

Accordingly, one aspect of the present invention is a method for categorizing a DNA sample, comprising:
(A) digesting a DNA sample with at least one of a methylation-sensitive restriction endonuclease and a methylation-dependent restriction endonuclease;
(B) amplifying at least two genomic loci from the digested DNA, wherein at least one of the loci is a restriction locus;
(C) determining the signal intensity of each amplification product;
(D) calculating signal ratios between the signal intensities of the amplification products; and
(E) comparing the signal ratios to reference values of different DNA categories,
wherein the approximation of the value of a signal ratio to the values of reference ratios of a particular DNA category indicates the categorical source of the DNA sample.

In one embodiment, the reference values against which the signal ratios are compared are from at least one DNA category selected from the group consisting of tissue type, cell type, physiological condition, pathological condition, age, ethnicity, sex, methylation level, species, cell lines, natural DNA and artificially-synthesized DNA, risk of developing a pathological condition, prenatal conditions, prognosis, propensity to respond to treatment, effects of cell line sub-culturing, response to medication.

In another embodiment, the tissue type or cell type is selected from the group consisting of blood, saliva, semen, epidermis, urine, plasma, hair, menstrual blood, vaginal cells and/or secretion, sweat, feces, brain, esophagus, lung, stomach, heart, duodenum, liver, gall bladder, intestine, kidney, adrenal gland, urinary bladder, urethra, colon, testicle, ovary, uterus, vagina, muscle, tendon, ligament, fat, cartilage, bone, endothelial cells, uterine cervix, lymph, thyroid, pituitary gland, cerebellum, and breast.

In a particular embodiment, the tissue type or cell type is blood, saliva, semen, or epidermis.

In another embodiment, the pathological condition is cancer, inflammation, auto-immune disorder, metabolic disorder, infection, degenerative disease, hormonal imbalances, a disorder characterized by abnormal DNA methylation, neurodevelopmental disorder of ICF (immunodeficiency, centromeric instability, and facial anomalies), Rett syndrome, and fragile X syndrome.

In one embodiment, the prenatal condition in Prader-Willi syndrome, Angelman syndrome, Beckwith-Wiedemann syndrome, fragile X syndrome, Russell-Silver syndrome, Transient neonatal diabetes mellitus, Albright hereditary osteodystrophy, McCune-Albright syndrome, Familial nonchromaffin paraganglioma, Maternal and paternal UPD14 syndromes.

In another embodiment, the reference values against which the signal ratios are compared represent categories that are mixtures of other categories.

In another embodiment, the reference values against which the signal ratios are compared are from mixtures of semen and non-semen at various ratios.

In one embodiment, the methylation-sensitive restriction endonuclease is selected from the group consisting of AatII, Acc65I, AccI, AciI, AclI, AfeI, AgeI, ApaI, ApaLI, AscI, AsiSI, AvaI, AvaII, BaeI, BanI, BbeI, BceAI, BcgI, BfuCI, BglI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, EagI-HF, EciI, EcoRI, EcoRI-HF, FauI, Fnu4HI, FseI, FspI, HaeII, HgaI, HhaI, HincII, HincII, HinfI, HinP1I, HpaI, HpaII, Hpy166ii, Hpy188iii, Hpy99I, HpyCH4IV, KasI, MluI, MmeI, MspA1I, MwoI, NaeI, Nan, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, PshAI, PspOMI, PvuI, RsaI, RsrII, SacII, Sa1I, SalI-HF, Sau3AI, Sau96I, ScrFI, SfiI, SfoI, SgrAI, SmaI, SnaBI, TfiI, TscI, TseI, TspMI, and ZraI.

In a particular embodiment, the methylation-sensitive restriction endonuclease is HhaI.

In another embodiment, the methylation-dependent restriction endonuclease is selected from the group consisting of McrBC, McrA, and MrrA.

In one embodiment, the reference DNA category is natural DNA or artificially-synthesized DNA, wherein at least one genomic locus in the natural DNA or artificially-synthesized DNA comprises a core short tandem repeat (STR) locus used for DNA profiling.

In another embodiment, the genomic locus comprises a human locus selected from the group consisting of D16S539 (SEQ ID NO. 1), D7S820 (SEQ ID NO. 2), D13S317 (SEQ ID NO. 3), D5S818 (SEQ ID NO. 4), CSF1PO (SEQ ID NO. 5), TPOX (SEQ ID NO. 6), TH01 (SEQ ID NO. 7), vWA (SEQ ID NO. 8), FGA (SEQ ID NO. 9), D21S11 (SEQ ID NO. 10), D8S1179 (SEQ ID NO. 11), D18551 (SEQ ID NO. 12), and D3S1358 (SEQ ID NO. 13), Penta D (SEQ ID NO. 14), Penta E (SEQ ID NO. 15), and Amelogenin (SEQ ID NOs. 16 and 17), D2S1338 (SEQ ID No. 18), D19S433 (SEQ ID No. 19), ACTBP2SE33 (SEQ ID No. 20), D10S1248 (SEQ ID No. 21), D1S1656 (SEQ ID No. 22), D22S1045 (SEQ ID No. 23), D2S441 (SEQ ID No. 24), and D12S391 (SEQ ID No. 25).

In one embodiment, the primers for amplification of at least one of the genomic loci are available in:

(1) a Promega Corporation commercial kit selected from the group consisting of PowerPlex® 16 HS (Cat.# DC2100, DC2101), PowerPlex® 16 (Cat.# DC6530, DC6531), PowerPlex® 2.1 (Cat.# DC6470, DC6471), PowerPlex® 16 BIO (Cat.# DC6540, DC6541), and PowerPlex® ES Systems (Cat.# DC6730, DC6731);

(2) an Applied Biosystems commercial kit selected from the group consisting of SGM, SGM+, AmpFlSTR Identifiler, AmpFlSTR Profiler, AmpFlSTR ProfilerPlus, AmpFlSTR ProfilerPlusID, AmpFlSTR SEfiler, AmpFlSTR SEfiler Plus, AmpFlSTR Cofiler, AmpFlSTR Identifiler Direct, AmpFlSTR Identifiler Plus, AmpFlSTR NGM, AmpFlSTR Y-filer, and AmpFlSTR Minifiler; or (3) Investigator ESSPlex, Investigator ESSPlex SE, Investigator Nonaplex ESSPlex, Investigator Hexaplex ESSPlex, Investigator Triplex AFS QS, Investigator Triplex DSF, Investigator IDplex, Investigator Decaplex SE, Investigator HDplex, Investigator Argus X-12, Investigator Y-12 QS, Investigator DIPplex.

In another embodiment, one of the genomic loci is known to be unmethylated in all tissues of natural DNA. In one embodiment, one of the genomic loci is selected from the group consisting of Hypo23, Hypo28, and Hypo33.

In another embodiment, the method further comprises calculating at least one of the following ratios:

(1) D3S1358/D18S51,
(2) D3S1358/D7S820,
(3) D3S1358/Penta_D,
(4) D3S1358/TPOX,
(5) D3S1358/FGA,
(6) TH01/Penta_D,
(7) D21S11/D18S51,
(8) D21S11/D7S820,
(9) D21S11/Penta_D,
(10) D21S11/AMEL,
(11) D21S11/TPOX,
(12) D21S11/FGA,
(13) D5S818/D18S51,
(14) vWA/D18S51,
(15) D5S818/Penta_E,
(16) vWA/Penta_E,
(17) D5S818/D7S820,
(18) D5S818/Penta_D,
(19) D5S818/TPOX,
(20) D5S818/FGA,
(21) D13S317/D7S820,
(22) D13S317/Penta_D,
(23) D13S317/TPOX,
(24) D13S317/FGA,
(25) D16S539/D7S820,
(26) CSF1PO/D7S820,
(27) vWA/D7S820,
(28) D8S1179/D7S820,
(29) D16S539/TPOX,
(30) D16S539/FGA,
(31) CSF1PO/Penta_D,
(32) CSF1PO/TPOX,
(33) vWA/Penta_D,
(34) AMEL/TPOX,
(35) AMEL/FGA,
(36) vWA/D8S1179,
(37) vWA/TPOX,
(38) vWA/FGA,
(39) D8S1179/TPOX, and
(40) D8S1179/FGA.

In a particular embodiment, at least one of the genomic loci is TPOX (SEQ ID NO. 6) or FGA (SEQ ID NO. 9).

In another embodiment, the amplified loci are 90 bps or smaller in size.

In one embodiment, signal intensity is the amplification product's fluorescence level measured during capillary electrophoresis.

In one embodiment, steps (B) and (C) of the method disclosed above are performed by real-time PCR. That is, in one embodiment, all of the required reagents and primers and enzymes necessary for DNA digestion and amplification by PCR are present together in the same tube or vessel.

In one embodiment, fluorescently-labeled primers are used to PCR amplify the chosen loci of the digested DNA, wherein the signal intensity of each amplification product is the fluorescence level of each amplification product.

In another embodiment, the method further comprises hybridizing a fluorescently-labeled probe to an amplification product, wherein the signal intensity of the amplification product is the fluorescence level measured after hybridization of the probe to the product.

In another embodiment, the method further comprises assigning confidence levels to potential categories of a DNA sample, wherein the confidence level reflects the likelihood that a particular DNA category indicates the categorical source of the DNA sample; wherein the likelihood is calculated by:

(A) assigning a probability score to each comparison of a signal ratio to the reference values that correspond to the various categories of DNA, wherein the probability score is obtained by (i) assigning a gamma probability distribution function to the reference values of each potential category; wherein (ii) the probability score is equal to the value of the gamma probability distribution function assigned in step (A) at the observed signal ratio;

(B) for each category, calculating the category likelihood score, which is the product of the probability scores obtained in step (A); and (C) normalizing likelihood scores by dividing the category likelihood score of each potential category by the sum of all category likelihood scores;

wherein the confidence level of each category is the normalized likelihood score of that category.

In another embodiment, the method further comprises simultaneously performing DNA profiling with the DNA categorization.

In one embodiment, the steps of DNA digestion and polymerase chain reaction are performed together in a single tube.

In one embodiment, the genomic loci that are amplified are chosen to produce distinct signal ratios for different potential categories.

Another aspect of the present invention is a kit for categorization of a DNA sample into at least two predetermined categories and for obtaining an associated categorization confidence level, comprising (1) primers for amplification of specific genomic loci; and at least one or more reagents selected from the group consisting of (2) a reaction buffer, (3) control DNA, (4) a methylation sensitive restriction endonuclease and/or a methylation dependent restriction endonuclease, (5) a written protocol for performing categorization. In one embodiment of the present invention, the written protocol may comprise instructions for performing any of the methods disclosed herein, including but not limited to, DNA digestion parameters, PCR cycling parameters, signal ratio analysis, and categorization analysis, as well as DNA profiling methods.

In another embodiment, the kit further comprises analysis software for performing categorization analyses.

Another aspect of the present invention is a kit for categorizing a DNA sample as semen or non-semen and for obtaining an associated categorization confidence level, comprising:

(a) primer mix, comprising the following primers:

```
                                           (SEQ ID NO. 55)
SD1f (AAGAGCCCATCAGGCAGGTC);

(SEQ ID NO. 56)
SD1r (GTTTCTTGTCGAGCAGCACGTGGATGATG);

(SEQ ID NO. 57)
SD2f (CTCCAGAACTGGAACTTCCTG);

(SEQ ID NO. 58)
SD2r (GTTTCTTAACTTGGAGACGACGGCATC);

(SEQ ID NO. 59)
SD3f (TGGAGGACAATGCCCTGGTG);

(SEQ ID NO. 60)
SD3r (GTTTCTTGGCTTCACCTGCGACCGTCTC);

(SEQ ID NO. 61)
SD4f (CCCTCCGAGTGGCCAGCAG);

(SEQ ID NO. 62)
SD4r (GTTTCTGACCACTGCCGTGGGAATG);

(SEQ ID NO. 63)
SD5f (CTTCTCAGCCAATGGGAAGAG);

(SEQ ID NO. 64)
SD5r (ACGTAGAAGGACCCGAGGAC);

(SEQ ID NO. 65)
SD6f (TACAGACAAATCACTCAGCAGC);
and (SEQ ID NO. 66)
SD6r (GTTTCTTGTCTGACACTCGGTTGTAGGTATT);
```

(b) reaction buffer;
(c) HhaI restriction endonuclease;
(d) DNA polymerase
(d) a written protocol for performing categorization.

In another embodiment, the kit further comprises control DNA samples.

In another aspect of the present invention is a kit for categorizing a DNA sample as semen or non-semen and for obtaining an associated categorization confidence level, comprising at least one pair of forward (f) and reverse (r) primer pair combinations selected from the group consisting of:

```
                                           (SEQ ID NO. 55)
(1) SD1f (AAGAGCCCATCAGGCAGGTC)
and (SEQ ID NO. 56)
    SD1r (GTTTCTTGTCGAGCAGCACGTGGATGATG);

(SEQ ID NO. 57)
(2) SD2f (CTCCAGAACTGGAACTTCCTG)
and (SEQ ID NO. 58)
    SD2r (GTTTCTTAACTTGGAGACGACGGCATC);

(SEQ ID NO. 59)
(3) SD3f (TGGAGGACAATGCCCTGGTG)
and (SEQ ID NO. 60)
    SD3r (GTTTCTTGGCTTCACCTGCGACCGTCTC);

(SEQ ID NO. 61)
(4) SD4f (CCCTCCGAGTGGCCAGCAG)
and (SEQ ID NO. 62)
    SD4r (GTTTCTGACCACTGCCGTGGGAATG);

(SEQ ID NO. 63)
(5) SD5f (CTTCTCAGCCAATGGGAAGAG)
and (SEQ ID NO. 64)
    SD5r (ACGTAGAAGGACCCGAGGAC);

(SEQ ID NO. 65)
(6) SD6f (TACAGACAAATCACTCAGCAGC)
and (SEQ ID NO. 66)
    SD6r (GTTTCTTGTCTGACACTCGGTTGTAGGTATT).
```

In one embodiment, the concentration of the primers in the primer mix are: 0.6 μM SD1f, 0.6 μM SD1r, 1.75 μM SD2f, 1.75 μM SD2r, 1.25 μM SD3f, 1.25 μM SD3r, 1.75 μM SD4f, 1.75 μM SD4r, 1.75 μM SD5f, 1.75 μM SD5r, 0.9 μM SD6f, and 0.9 μM SD6r.

In one embodiment, the reaction buffer comprises 150 mM TRIS-HCl, 15 mM $MgCl_2$, 0.2 mM each dntp, and 0.1 μg/μl BSA.

In one embodiment, the kit further comprises a DNA ladder.

In one embodiment, the kit further comprises analysis software for performing categorization analyses.

Another aspect of the present invention is a kit for profiling, categorizing a DNA sample as semen or non-semen, and obtaining an associated categorization confidence level, comprising:

(a) primers for amplifying at least one semen-specific locus;
(b) primers for amplifying at least one locus used for DNA profiling;
(c) reaction buffer;
(d) HhaI restriction endonuclease,
(e) DNA polymerase
(f) a written protocol for performing categorization.

In one embodiment, the kit further comprises control DNA samples.

Another aspect of the present invention is a kit for profiling, categorizing a DNA sample as semen or non-semen, and obtaining an associated categorization confidence level, comprising:

(a) primers for amplifying at least one semen-specific locus; and
(b) primers for amplifying at least one locus used for DNA profiling.

In one embodiment, at least one semen-specific locus amplified by a kit disclosed herein is the L68346 locus. In one embodiment, the primers for amplifying a 70 by semen-specific amplification product from L68346 are a forward primer comprising the sequence of CAGCAACAGCAC- CCAGCTTG (SEQ ID NO. 68) (FAM) and a reverse primer comprising the sequence of CACAGGCTCAGTCGCGGATC (SEQ ID NO. 83).

In one embodiment, at least one semen-specific locus amplified by a kit disclosed herein is the L16264 locus. In one embodiment, the primers for amplifying a 95 by semen-specific amplification product from L16264 are a forward primer comprising the sequence of GGACGAGTTAACTTCCTTAATTTC (SEQ ID NO. 102) (FAM) and reverse primer comprising the sequence of GTTTCTTCGCGGAACCTGGTTTAACTTC (SEQ ID NO. 104).

In another embodiment, the reaction buffer comprises 150 mM TRIS-HCl, 15 mM MgCl$_2$, 0.2 mM each dntp, and 0.1 µg/µl BSA.

In another embodiment, the kit further comprises at least one of (a) a DNA ladder, (b) a Material Safety Data Sheet (MSDS), and (c) analysis software for performing categorization analyses.

Another aspect of the present invention is a kit for categorizing a DNA sample as blood, saliva, semen, or skin epidermis, and for obtaining an associated categorization confidence level, comprising:

(a) primer mix that comprises forward and reverse primers for amplifying the denoted loci as follows:

1. L91762

(forward GCAGCAGGCCGCGGAGAAG (SEQ ID NO. 67) (FAM);

reverse AGCAGCTGTGCCGGGCCAG) (SEQ ID NO. 82)

2. L68346
(forward CAGCAACAGCACCCAGCTTG (SEQ ID NO. 68) (JOE);

reverse CACAGGCTCAGTCGCGGATC) (SEQ ID NO. 83)

3. L50468
(forward AGGAAACCTCAGTAGCAAAATTG (SEQ ID NO. 69) (JOE);

reverse GCGAGACTTTAGGTGTGCATC) (SEQ ID NO. 84)

4. L14432
(forward CGTAGGCTGCGGTGAGCTC (SEQ ID NO. 70) (FAM);

reverse GATCCATGCCCGCTGGGATG) (SEQ ID NO. 85)

5. L4648
(forward CAGCCTAGACGTCAAGTTACAG (SEQ ID NO. 71) (JOE);

reverse ACGACCTCCGGATCCAACTG) (SEQ ID NO. 86)

6. L39664
(forward CCCAGCTGGTTGGACATGTTG (SEQ ID NO. 72) (FAM);

reverse CACTTCCTTCGTGGACGCC) (SEQ ID NO. 87)

7. L30139
(forward GAGAAGCGGGAGGATGAGAC (SEQ ID NO. 73) (FAM);

reverse CCGCATCTCCTCCGTCCTG) (SEQ ID NO. 88)

8. L55429
(forward GCCTTCAGCAGGAAGTCCAC (SEQ ID NO. 74) (JOE);

reverse CCTGTGCCTCACACAGACTC) (SEQ ID NO. 89)

9. L62086
(forward GTGCATGGTGTCTGGTACTTC (SEQ ID NO. 75) (FAM);

reverse GAAGCTCTCGTGGACTACTTG) (SEQ ID NO. 90)

10. L76138
(forward CAGCCTGCTCTTCACTGCAG (SEQ ID NO. 76) (JOE);

reverse AGAGGCCGATGAAGCCGTAG) (SEQ ID NO. 91)

11. L15952
(forward CTCCCTGATTTACGACAAGTTC (SEQ ID NO. 77) (FAM);

reverse GACAGTATGCTGATGCTTCTTG) (SEQ ID NO. 92)

12. L36599
(forward AAGGGCAGAGTTCCGCTGTC (SEQ ID NO. 78) (FAM);

reverse CGGATGCAGGAGGATCCTAG) (SEQ ID NO. 93)

13. L26688
(forward CGGACCAGATTGCTGGTCAC (SEQ ID NO. 79) (JOE);

reverse CGACCTTGCCAGATGTTTGAC) (SEQ ID NO. 94)

14. L81528
(forward AGCCTCATCCACACTGACCAG (SEQ ID NO. 80) (JOE);

reverse TCAGAGCTCTCCTATCTGGAC) (SEQ ID NO. 95)

15. L36556
(forward GCCAGGCCGTTGATGATGAC (SEQ ID NO. 81) (JOE);

reverse GAATATGGAGCCCTGGGCAG) (SEQ ID NO. 96)

(b) reaction buffer;
(c) HhaI restriction endonuclease;
(d) DNA polymerase
(e) a written protocol for performing categorization.

In another embodiment, the kit further comprises control DNA samples.

In one embodiment, the reaction buffer comprises 150 mM TRIS-HCl, 15 mM MgCl$_2$, 0.2 mM each dntp, and 0.1 µg/µl BSA.

In another embodiment, the kit further comprises at least one of (a) a DNA ladder, (b) a Material Safety Data Sheet (MSDS), and (c) analysis software for performing categorization analyses.

In one embodiment in any of the methods disclosed herein, the DNA sample comprises a mixture of DNA samples.

Another aspect of the present invention is a method for calculating a distance measure of differential methylation between DNA samples, comprising:

(A) digesting each DNA sample with a methylation-sensitive and/or methylation-dependent restriction endonuclease;
(B) performing PCR on each digested DNA amplifying at least two genomic loci of which at least one is a restriction locus;
(C) for each DNA sample, determining the intensity of the signal of each amplification product;
(D) for each DNA sample, calculating "signal ratios" between the intensities of the signals produced by the loci;
(E) calculating the differential methylation measure between DNA samples by performing a quantitative comparison of their corresponding signal ratios.

In one embodiment of this method, the distance measure is sum of absolute differences between the signal ratios of the DNA samples.

In another embodiment of this method, the distance measure is the square-root of the sum of squared differences between the signal ratios of the DNA samples.

In one embodiment of this method, the distance measured between a subject sample and a reference healthy sample indicates the amount of medication required to treat a pathological state.

In another embodiment of this method, the distance measured between a DNA sample obtained from cultured cells to a reference sample indicates the number of sub-culturing procedures that the cells underwent.

Another aspect of the present invention is a primer selected from the group consisting of:

```
 1. GCAGCAGGCCGCGGAGAAG;        (SEQ ID NO. 67)
 2. AGCAGCTGTGCCGGGCCAG;        (SEQ ID NO. 82)
 3. CAGCAACAGCACCCAGCTTG;       (SEQ ID NO. 68)
 4. CACAGGCTCAGTCGCGGATC;       (SEQ ID NO. 83)
 5. AGGAAACCTCAGTAGCAAAATTG;    (SEQ ID NO. 69)
 6. GCGAGACTTTAGGTGTGCATC;      (SEQ ID NO. 84)
 7. CGTAGGCTGCGGTGAGCTC;        (SEQ ID NO. 70)
 8. GATCCATGCCCGCTGGGATG;       (SEQ ID NO. 85)
 9. CAGCCTAGACGTCAAGTTACAG;     (SEQ ID NO. 71)
10. ACGACCTCCGGATCCAACTG;       (SEQ ID NO. 86)
11. CCCAGCTGGTTGGACATGTTG;      (SEQ ID NO. 72)
12. CACTTCCTTCGTGGACGCC;        (SEQ ID NO. 87)
13. GAGAAGCGGGAGGATGAGAC;       (SEQ ID NO. 73)
14. CCGCATCTCCTCCGTCCTG;        (SEQ ID NO. 88)
15. GCCTTCAGCAGGAAGTCCAC;       (SEQ ID NO. 74)
16. CCTGTGCCTCACACAGACTC;       (SEQ ID NO. 89)
17. GTGCATGGTGTCTGGTACTTC;      (SEQ ID NO. 75)
18. GAAGCTCTCGTGGACTACTTG;      (SEQ ID NO. 90)
19. CAGCCTGCTCTTCACTGCAG;       (SEQ ID NO. 76)
20. AGAGGCCGATGAAGCCGTAG;       (SEQ ID NO. 91)
21. CTCCCTGATTTACGACAAGTTC;     (SEQ ID NO. 77)
22. GACAGTATGCTGATGCTTCTTG;     (SEQ ID NO. 92)
23. AAGGGCAGAGTTCCGCTGTC;       (SEQ ID NO. 78)
24. CGGATGCAGGAGGATCCTAG;       (SEQ ID NO. 93)
25. CGGACCAGATTGCTGGTCAC;       (SEQ ID NO. 79)
26. CGACCTTGCCAGATGTTTGAC;      (SEQ ID NO. 94)
27. AGCCTCATCCACACTGACCAG;      (SEQ ID NO. 80)
28. TCAGAGCTCTCCTATCTGGAC;      (SEQ ID NO. 95)
29. GCCAGGCCGTTGATGATGAC;       (SEQ ID NO. 81)
    and
30. GAATATGGAGCCCTGGGCAG        (SEQ ID NO. 96)
31. AAGAGCCCATCAGGCAGGTC        (SEQ ID NO. 55)
32. GTTTCTTGTCGAGCAGCACGTGGATGATG (SEQ ID NO. 56)
33. CTCCAGAACTGGAACTTCCTG       (SEQ ID NO. 57)
34. GTTTCTTAACTTGGAGACGACGGCATC (SEQ ID NO. 58)
35. TGGAGGACAATGCCCTGGTG        (SEQ ID NO. 59)
36. GTTTCTTGGCTTCACCTGCGACCGTCTC (SEQ ID NO. 60)
37. CCCTCCGAGTGGCCAGCAG         (SEQ ID NO. 61)
38. GTTTCTGACCACTGCCGTGGGAATG   (SEQ ID NO. 62)
39. CTTCTCAGCCAATGGGAAGAG       (SEQ ID NO. 63)
40. ACGTAGAAGGACCCGAGGAC        (SEQ ID NO. 64)
41. TACAGACAAATCACTCAGCAGC      (SEQ ID NO. 65)
42. GTTTCTTGTCTGACACTCGGTTGTAGGTATT (SEQ ID NO. 66)
43. GGACGAGTTAACTTCCTTAATTTC    (SEQ ID NO. 102)
44. GTTTCTTCGCGGAACCTGGTTTAACTTC (SEQ ID NO. 104)
```

Another aspect of the present invention is a primer pair for amplifying a specific human genomic locus selected from the group consisting of:

1. L91762
(forward GCAGCAGGCCGCGGAGAAG (SEQ ID NO. 67)
(FAM);

reverse AGCAGCTGTGCCGGGCCAG) (SEQ ID NO. 82);

2. L68346
(forward CAGCAACAGCACCCAGCTTG (SEQ ID NO. 68)
(JOE);

reverse CACAGGCTCAGTCGCGGATC) (SEQ ID NO. 83);

3. L50468
(forward AGGAAACCTCAGTAGCAAAATTG (SEQ ID NO. 69)
(JOE);

reverse GCGAGACTTTAGGTGTGCATC) (SEQ ID NO. 84);

4. L14432
(forward CGTAGGCTGCGGTGAGCTC (SEQ ID NO. 70)
(FAM);

reverse GATCCATGCCCGCTGGGATG) (SEQ ID NO. 85);

5. L4648
(forward CAGCCTAGACGTCAAGTTACAG (SEQ ID NO. 71)
(JOE);

reverse ACGACCTCCGGATCCAACTG) (SEQ ID NO. 86);

6. L39664
(forward CCCAGCTGGTTGGACATGTTG (SEQ ID NO. 72)
(FAM);

reverse CACTTCCTTCGTGGACGCC) (SEQ ID NO. 87);

7. L30139
(forward GAGAAGCGGGAGGATGAGAC (SEQ ID NO. 73)
(FAM);

reverse CCGCATCTCCTCCGTCCTG) (SEQ ID NO. 88);

8. L55429
(forward GCCTTCAGCAGGAAGTCCAC (SEQ ID NO. 74)
(JOE);

reverse CCTGTGCCTCACACAGACTC) (SEQ ID NO. 89);

9. L62086
(forward GTGCATGGTGTCTGGTACTTC (SEQ ID NO. 75)
(FAM);

reverse GAAGCTCTCGTGGACTACTTG) (SEQ ID NO. 90);

10. L76138
(forward CAGCCTGCTCTTCACTGCAG (SEQ ID NO. 76)
(JOE);

reverse AGAGGCCGATGAAGCCGTAG) (SEQ ID NO. 91);

11. L15952
(forward CTCCCTGATTTACGACAAGTTC (SEQ ID NO. 77)
(FAM);

reverse GACAGTATGCTGATGCTTCTTG) (SEQ ID NO. 92);

12. L36599
(forward AAGGGCAGAGTTCCGCTGTC (SEQ ID NO. 78)
(FAM);

reverse CGGATGCAGGAGGATCCTAG) (SEQ ID NO. 93);

13. L26688
(forward CGGACCAGATTGCTGGTCAC (SEQ ID NO. 79)
(JOE);

reverse CGACCTTGCCAGATGTTTGAC) (SEQ ID NO. 94);

-continued

14. L81528
(forward AGCCTCATCCACACTGACCAG (SEQ ID NO. 80)
(JOE);

reverse TCAGAGCTCTCCTATCTGGAC) (SEQ ID NO. 95);

15. L36556
(forward GCCAGGCCGTTGATGATGAC (SEQ ID NO. 81)
(JOE);

reverse GAATATGGAGCCCTGGGCAG) (SEQ ID NO. 96).

16. SD1
(forward AAGAGCCCATCAGGCAGGTC (SEQ ID NO. 55)
(FAM);

reverse GTTTCTTGTCGAGCAGCACGTGGATGATG)
(SEQ ID NO. 56);

17. SD2
(forward CTCCAGAACTGGAACTTCCTG (SEQ ID NO. 57)
(FAM);

reverse GTTTCTTAACTTGGAGACGACGGCATC)
(SEQ ID NO. 58);

18. SD3
(forward TGGAGGACAATGCCCTGGTG (SEQ ID NO. 59)
(FAM);

reverse GTTTCTTGGCTTCACCTGCGACCGTCTC)
(SEQ ID NO. 60);

19. SD4
(forward CCCTCCGAGTGGCCAGCAG (SEQ ID NO. 61)
(FAM);

reverse GTTTCTGACCACTGCCGTGGGAATG)
(SEQ ID NO. 62);

20. SD5
(forward CTTCTCAGCCAATGGGAAGAG (SEQ ID NO. 63)
(FAM);

reverse ACGTAGAAGGACCCGAGGAC) (SEQ ID NO. 64);

21. SD6
(forward TACAGACAAATCACTCAGCAGC (SEQ ID NO. 65)
(FAM);

reverse GTTTCTTGTCTGACACTCGGTTGTAGGTATT)
(SEQ ID NO. 66);
and

22. L16264
(forward GGACGAGTTAACTTCCTTAATTTC (SEQ ID NO. 102)
(FAM);

reverse GTTTCTTCGCGGAACCTGGTTTAACTTC)
(SEQ ID NO. 104).

BRIEF DESCRIPTION OF THE DRAWINGS

FIGS. 1A-D. Tissue identification assay. (A) Schematic overview of the assay. (B) Biochemical procedure—methylated loci remain intact during digestion and subsequently are amplified efficiently in the PCR, producing a strong signal (locus A) while unmethylated loci are digested and subsequently amplify inefficiently in the PCR, producing a weak signal (Locus B). The signal ratio (SR; rfu of locus A/rfu of locus B) reflects the differential methylation level between loci A and B. (C) Signal ratios between locus 1 and locus 2 are different in blood, saliva, skin, and semen, reflecting the differential methylation patterns in these tissues. (D) The observed differences in signal ratios between blood and semen (i.e. the signal) are more than a magnitude greater than the observed differences in signal ratios obtained from different PCRs and from different amounts of input DNA (i.e. the noise).

FIG. 6. Simulation of degraded samples. Blood (top) and semen (bottom) samples were partially digested using DNAseI and analyzed with the combined semen detection and profiling assay. Although only partial profiles were obtained for both samples, the smaller tissue identification loci (the two loci in the top channel to the left of D3S1358) amplified successfully with the expected pattern, and the algorithm correctly identified the presence/absence of semen in these samples.

FIG. 7. Table 1.
FIG. 8. Table 2.
FIG. 9. Table 3.
FIG. 10. Table 4.
FIG. 11. Table 5.

DETAILED DESCRIPTION

1. Introduction

Figure 2:
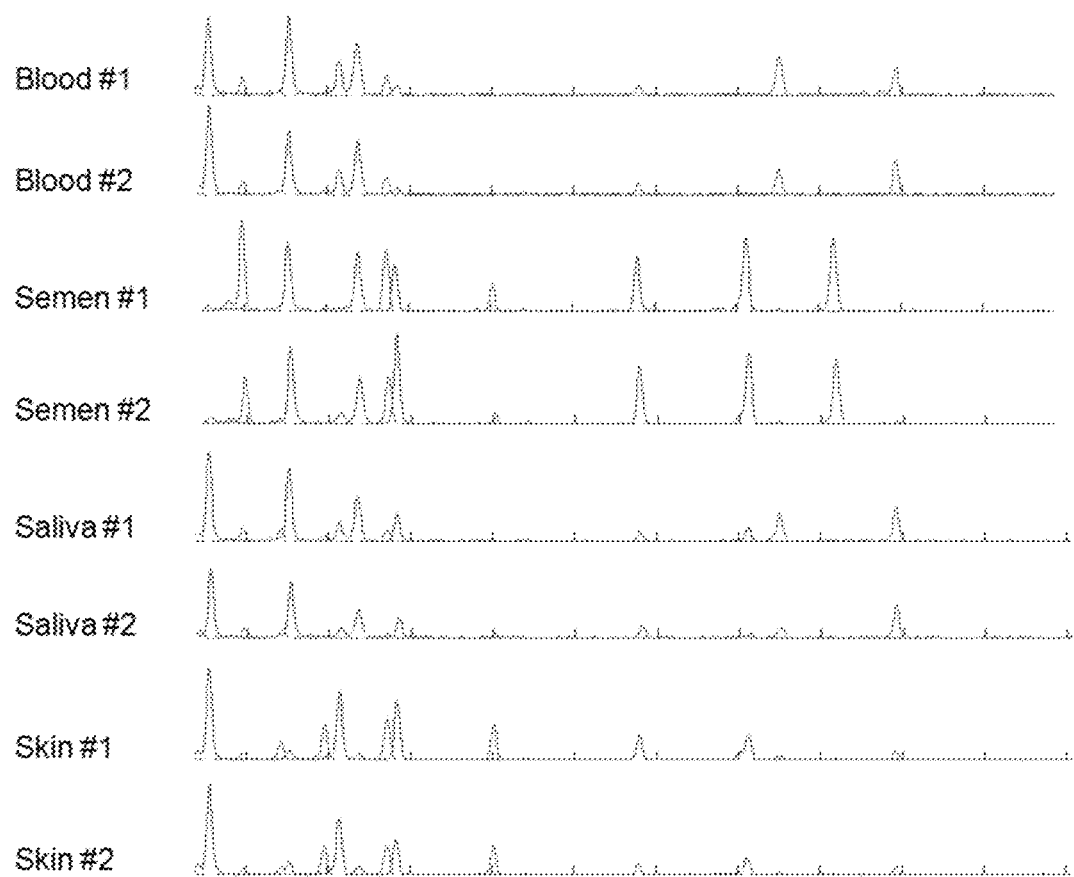
FIG. 2. Tissue identification of different tissue types. Electropherograms of 8 samples (2 samples from each of 4 different tissues) are depicted demonstrating the distinct amplification pattern observed for each tissue type.

The present invention relates to methods and assays that enable distinguishing between sources of DNA using loci-specific primers and commercially available enzymes. An underlying aspect of an inventive assay is the comparison of signals from at least two loci amplified from a particular source of DNA, which ultimately yields a numerical ratio that indicates whether that source of the DNA sample is, in one embodiment, natural or artificial. The inventive assays also can be used to distinguish between, for example, different physiological and pathological sources of DNA and between different tissues.

The signal ratios employed by the assay are correlated to methylation levels at specific genomic loci, but do not indicate actual methylation levels at any genomic locus. Therefore the invention setup eliminates the requirement for external DNA species and/or controls, thereby both simplifying and increasing the accuracy of the assay.

The inventive DNA categorization assays described herein are therefore powerful, multiplex, accurate, and inexpensive techniques applicable in any setting that calls for the categorization of a DNA sample. Thus, the inventive assays can be used, for example, by the police in a forensics capacity; the health care industry for diagnostic and therapeutic purposes; in the insurance industry to verify claims pursuant to anti-discrimination genetic laws, such as the Genetic Information Nondiscrimination Act (H.R. 493); by prosecutors and defense counsel for evidentiary purposes in criminal trials and civil proceedings and appeals; and the food and agriculture industry to verify the integrity of meats, crops, and plants such as grapevines and sources of coffee. The present invention is not limited to this non-exclusive, but representative, list of applications.

An underlying principle of a method disclosed herein therefore is the measurement of signal intensities between amplified genomic loci and their subsequent pairwise comparison against each other to produce ratios of signal intensities between the amplified loci. For example, if loci A, B, C, and D are all amplified according to the techniques described herein, then the signal intensity for each of A, B, C, and D is measured and recorded. Then, the signal intensities of A and B, A and C, and A and D are compared respectively and signal intensity ratios calculated for each of the A/B, A/C and A/D combinations. Then, the signal intensity ratios of B/C and B/D are calculated, and so on.

The value of each of those signal intensity ratios can then be compared against the values of known reference signal intensity ratios of DNAs whose source of origin is known. Thus, for instance, in the case of DNA whose source of origin is known to be human semen, the signal intensity ratios of loci, such as the pairwise ratios of the A, B, C, and D illustrative loci are known, or can be readily established afresh when analysing a test DNA sample. Thus the DNA category is "semen" and its respective signal intensity ratios for those loci are reference values against which the test DNA sample may be compared.

Accordingly, after establishing the various signal intensity ratios of loci A, B, C, and D, from the DNA sample, each ratio can be compared against one or more reference values of particular known categories of DNA, e.g., against the semen DNA ratio values. The ratio of any loci combination from the DNA sample that more closely approximates the signal intensity ratio reference value of a particular DNA category means it is highly likely that the tested DNA sample originated from that particular category of DNA to which it more or most closely approximates when compared. Thus, a signal intensity ratio from the tested DNA sample of the A/B loci that is the same as, or close to, the value of the signal intensity ratio of the A/B loci from semen indicates that the tested DNA sample likely originated from semen. By conducting the same comparative analysis across many different loci, and against many different reference categories, the likelihood that the tested DNA sample originated from a particular biological source, or that it did not originate from a particular biological source, increases.

Similarly, in a situation where a sample might comprise mixtures of DNA from different sources, such as saliva and blood, or saliva, blood, epidermis, and semen, it will be possible, by performing the methods disclosed herein, to identify the presence of different categories of DNAs within the sample. Thus, the identification of multiple as well as sole sources of DNA present in a sample can be achieved using the methods and reagents disclosed herein.

Accordingly, the present "categorization" methods can also be thought of as a tissue identification assay. In one example, as explained in the following passage, a tissue identification assay uses a panel of loci that are differentially methylated between tissues to determine the most probable source tissue of a DNA sample. See Table 1 (FIG. 7). A scheme of the assay is presented in FIG. 1A. DNA from a forensic sample is digested with, for example, the HhaI methylation-sensitive restriction enzyme, which cleaves DNA at its recognition sequence GCGC only if it is unmethylated (while leaving methylated targets intact).

A panel of tissue identification loci is then amplified by PCR from the digested DNA using fluorescently-labeled primers, and an aliquot of amplified products is separated by capillary electrophoresis. In the situation with HhaI-digested DNA, loci with higher methylation levels are amplified with higher efficiency because more DNA molecules are protected from digestion, producing a relatively strong signal in the electropherogram (FIG. 1B, locus A). Conversely, loci with a lower methylation level are amplified with lower efficiency, yielding a relatively weak signal in the electropherogram (FIG. 1B, locus B).

Automated signal analysis software disclosed herein enables analysis of an output electropherogram, and assigns heights (in rfu) to amplicons corresponding to tissue identification loci. Thus, the height of a single locus is correlated with its methylation level. Ratios of methylation levels between co-amplified loci can then be calculated as described generically above. For each pair of loci a signal ratio, calculated as the ratio between the heights of the first and second loci, and this ratio reflects the ratio between the methylation levels of the corresponding loci.

All calculated signal ratios can then be combined into a single numerical value. For example, 105 pairwise ratios can be calculated from a panel of 15 loci (e.g., as between locus 1 and 2, locus 1 and 3, etc.). Those can then be compared to a database of reference values obtained from a data set of samples of known tissue origin. The tissue identification algorithm calculates for each potential tissue source a likelihood score, reflecting the likelihood that the DNA sample originated from that tissue, and the output of the algorithm is the most likely tissue. Disclosed elsewhere herein are algorithms and specific calculations for deriving likelihood and probability scores from these ratios and comparisons.

As shown in Example 1, for instance, such a tissue identification assay was performed on 50 samples: 14 blood, 14 saliva, 11 semen, and 11 skin epidermis using a panel of 15 tissue identification loci, ranging in amplicon size from 66 to 150 bps. FIG. 2 depicts electropherograms of eight of these samples—two of each tissue type. Each tissue type had a distinct methylation profile. For example, the ratio of the L91762/L68346 loci in semen samples ranged from 0.04-0.53 and was higher in all other tissue samples (2.15-18.28; see Table 2 in FIG. 8). Therefore a low L91762/L68346 ratio was found to be distinctive of semen samples. The ratio of the L76138/L26688 loci, however, was low in blood and saliva (0.08-1.54) and higher in semen and skin epidermis (2.04-19.56; Table 2 in FIG. 8). Therefore a high ratio of L91762/L68346 concomitant with a high ratio of L76138/L26688 was distinctive of skin epidermis samples The tissue identification algorithm disclosed herein correctly identified the true tissue source of all 50 samples. Further analysis of the data using subsets of tissue identification loci revealed that the full set of 15 loci was redundant and 100% identification was achieved by using only 7 out of the 15 loci (L91762, L68346, L50468, L14432, L30139, L15952, and L26688).

Accordingly, this illustrative example corroborates the generic inventive aspect of the present invention, namely that the comparative signal intensity ratio analyses provides exacting and correct DNA sample identification and categorization.

Furthermore, another significant aspect of the present invention is that it can readily complement and expand the usefulness of existing commercial DNA profiling kits to do more than profile a particular subject's DNA. The combination of the inventive assays disclosed herein, such as the signal ratio assay described in detail below, with Promega Corporation's PowerPlex® 16 kit, for example, enables a user to not only profile an individual's DNA composition but also to determine whether the profiled DNA is from a natural source or has been artificially synthesized. In another example, combining DNA profiling with DNA categorization enables a user to both profile DNA and determine the source tissue of the DNA sample.

For instance, one assay described herein may employ both conventional profiling of a DNA sample, for example with the PowerPlex16 kit (Promega), and categorization of DNA into categories of natural vs. artificial. See, for instance, Example 6 below.

For illustrative purposes only of how combined categorization and profiling may work together as disclosed herein, two samples of DNA are analyzed: (1) a natural DNA sample extracted from the blood of subject A, and (2) an artificial DNA sample synthesized by in vitro multiple displacement amplification using a commercial kit from a minute quantity of subject A's real DNA as template.

Furthermore, this illustration demonstrates how the present inventive method is far superior to any existing method because it is able to distinguish artificial DNA from natural DNA samples even though conventional profiling kits would identify both samples as identical to one another—because both the natural and artificial DNA are from subject A. Accordingly, notwithstanding the fact that the profiling kit would identify the samples as the same, the present inventive signal intensity ratio analyses can readily tell them apart and identify one profile as generated from artificial DNA, while the other profile was generated from natural DNA.

To explain further, the two samples are first profiled with PowerPlex16 and analyzed using a conventional profiling software, such as GeneMapperID-X. The scheme of this procedure can be briefly described as (1) performing multiplex PCR using the PowerPlex16 primer mix on a DNA sample; (2) separating the amplification products on a capillary electrophoresis machine; and then (3) analyzing the output data with, for instance, the GeneMapperID-X software. For each of the samples, the end product of this assay is a profile. The profiles of the two samples are identical. See FIGS. 9A-B.

Furthermore, the GeneMapperID-X software determined the profiles of both samples to be single contributor (i.e. from a single person) profiles, with no anomalies. This shows that a profile obtained from artificial DNA can be identical to a profile obtained from natural DNA. See D.

Frumkin, et al., *Authentication of forensic DNA samples*, Forensic Sci. Int. Genet. (2009), doi:10.1016/j.fsigen.2009.06.009, which is incorporated herein by reference.

Both samples of DNA were subsequently also analyzed by a combined profiling and categorization assay based on the following scheme: digest a DNA sample with HhaI and perform multiplex PCR using the PowerPlex16 primer mix with the addition of primers for amplifying an additional locus, such as Hypo23; separating the amplification products on a capillary electrophoresis machine; and analyzing the output data with the capillary analyzer software, such as the software algorithm disclosed herein.

For each sample, the end product of this assay is a profile and assignment of category. As can be seen in FIGS. 9C and D, the natural DNA was assigned as "natural," in contrast to the artificial sample which was assigned as "artificial."

In this particular example, the assignment of category was performed by analysis of three parameters: (1) SR1 (signal ratio of TPOX/D8S1179), (2) SR2 (signal ratio of D3S1358/Hypo23), and (3) RR (representation ratio of OCA2/D3S1358).

The threshold values for these parameters are provided in Table 6:

TABLE 6

| | SR1 | SR2 | RR |
|---|---|---|---|
| Threshold for natural | >=0.9 | >=10 | >=2 |
| Threshold for artificial | <0.9 | <10 | <2 |

The observed values for these parameters, and the assigned category are provided in Table 7 (all values are above the threshold for natural DNA but only the RR category is above the threshold for artificial DNA).

TABLE 7

| | SR1 | SR2 | RR | Category |
|---|---|---|---|---|
| Natural DNA sample | 1.23 | 17.54 | 3.31 | Natural |
| Artificial DNA sample | 0.06 | 2.06 | 2.47 | Artificial |

Assignment of the category was performed according to the following rule:

If all observed parameter values are above their respective thresholds for natural DNA, then assign a "natural" category, otherwise assign an "artificial" category. Thus, the present inventive signal intensity ratio analyses can readily identify sources of DNA, such as for example from natural vs. artificial sources, and in conjunction with DNA profiling techniques provides a powerful and sophisticated method for identifying genomic materials.

Specific compositions, methods, or embodiments discussed are intended to be only illustrative of the invention disclosed by this specification. Variations on these compositions, methods, or embodiments are readily apparent to a person of skill in the art based upon the teachings of this specification and are therefore intended to be included as part of the inventions disclosed herein.

In practicing the present invention, many conventional techniques in molecular biology and recombinant DNA are used. These techniques are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); Perbal, *A Practical Guide to Molecular Cloning*; the series, Meth. Enzymol., (Academic Press, Inc., 1984); *Gene Transfer Vectors for Mammalian Cells*, Miller & Calos, Eds. (Cold Spring Harbor Laboratory, N.Y., 1987); and *Meth. Enzymol.*, Vols. 154 and 155, Wu & Grossman, and Wu, Eds., respectively.

2. Definitions

The present technology is described herein using several definitions, as set forth throughout the specification. Unless defined otherwise, all technical and scientific terms used herein generally have the same meaning as commonly understood by one of ordinary skill in the art to which this invention belongs. As used herein, unless otherwise stated, the singular forms "a," "an," and "the" include plural reference. Thus, for example, a reference to "a nucleic acid" is a reference to one or more nucleic acids.

As used herein, the term "allele" is intended to be a genetic variation associated with a segment of DNA, i.e., one of two or more alternate forms of a DNA sequence occupying the same locus.

The term "artificial DNA" or "artificially-synthesized DNA" or "artificial nucleic acid" as used herein refers to a nucleic acid which is synthesized by various in vitro methods. Herein disclosed are the characterizations of different methods for synthesizing DNA in vitro. Such in vitro generated nucleic acids include, but are not limited to:

1. Chemically synthesized oligonucleotides.
2. Products of PCR amplification of target sequences.
3. Products of Rolling circle amplification (RCA) of circular target sequences.
4. Products of molecular cloning (e.g. plasmids cloned in *E. coli*.)
5. DNA fragments assembled from other DNA fragments that were generated by any of methods 1-4, or a combination of them. Such assembly being achieved by any of the following methods (or a combination of them): annealing, ligation, polymerization. The process of assembly may also include steps of breaking DNA molecules (e.g. by restriction endonucleases, mechanical shearing etc.)
6. Products of PCR-based Whole genome amplification (WGA), and/or ligation mediated PCR (LMP)-based WGA methods, including primer extension preamplification (PEP)-PCR, degenerate oligonucleotide primed (DOP)-PCR, T7-based linear amplification of DNA (TLAD), Adaptor-Ligation PCR. The Genomeplex (Sigma) commercial kit utilizes Adaptor-Ligation PCR.
7. Products of WGA by Multiple displacement amplification (MDA) and Restriction and Circularization-Aided Rolling Circle Amplification (RCA-RCA). The Repli-G (Qiagen), and GenomiPhi (GE Healthcare) commercial kits utilize this method.
8. A mix of products from any of 1-7.
9. Products from any of 1-8 in which all or some products were methylated in vitro following their synthesis (e.g. by Sss1 Methylase).
10. Products from any of 1-8 mixed with natural DNA.
11. Products from 9 mixed with natural DNA.

The term "biological sample" or "test sample" as used herein, refers to, but is not limited to, any biological sample derived from, or obtained from, a subject. The sample may comprise nucleic acids, such as DNAs or RNAs. In some embodiments, samples are not directly retrieved from the subject, but are collected from the environment, e.g. a crime scene or a rape victim. Examples of such samples include but are not limited to fluids, tissues, cell samples, organs, biopsies, etc. Suitable samples include but are not limited to are blood, plasma, saliva, urine, sperm, hair, etc. The biological sample can also be blood drops, dried blood stains, dried saliva stains, dried underwear stains (e.g. stains on underwear, pads, tampons, diapers), clothing, dental floss, ear wax, electric razor clippings, gum, hair, licked envelope, nails, paraffin embedded tissue, post mortem tissue, razors, teeth, toothbrush, toothpick, dried umbilical cord. Genomic DNA can be extracted from such samples according to methods known in the art. (for example using a protocol from Sambrook et al., *Molecular Cloning: A Laboratory Manual*, Second Ed., Cold Spring Harbor Laboratory Press, Cold Spring Harbor, N.Y., 1989);

The term "capillary electrophoresis histogram" as used herein refers to a histogram obtained from capillary electrophoresis of PCR products wherein the products were amplified from genomic loci with fluorescent primers.

The term "methylated" as used herein means methylated at a level of at least 80% (i.e. at least 80% of the DNA molecules methylated) in DNA of cells of tissues including blood, saliva, semen, epidermis, nasal discharge, buccal cells, hair, nail clippings, menstrual excretion, vaginal cells, urine, and feces.

The term "partially-methylated" as used herein means methylated at a level between 20-80% (i.e. between 20-80% of the DNA molecules methylated) in DNA of cells of tissues including blood, saliva, semen, epidermis, nasal discharge, buccal cells, hair, nail clippings, menstrual excretion, vaginal cells, urine, and feces.

The term "unmethylated" as used herein means methylated at a level less than 20% (i.e. less than 20% of the DNA molecules methylated) in DNA of cells of tissues including blood, saliva, semen, epidermis, nasal discharge, buccal cells, hair, nail clippings, menstrual excretion, vaginal cells, urine, bone, and feces. The methods provided herein have been demonstrated to distinguish methylated and unmethylated forms of nucleic acid loci in various tissues and cell types including blood, saliva, semen, epidermis, nasal discharge, buccal cells, hair, nail clippings, menstrual excretion, vaginal cells, urine, bone, and feces.

The terms "determining," "measuring," "assessing," "assaying," and "evaluating" are used interchangeably to refer to any form of quantitative or qualitative measurement, and include determining if a characteristic, trait, or feature is present or not. Assessing may be relative or absolute. "Assessing the presence of" includes determining the amount of something present, as well as determining whether it is present or absent.

The term "forensics" or "forensic science" as used herein refers to the application of a broad spectrum of methods aimed to answer questions of identity being of interest to the legal system. For example, the identification of potential suspects whose DNA may match evidence left at crime scenes, the exoneration of persons wrongly accused of crimes, identification of crime and catastrophe victims, or establishment of paternity and other family relationships.

The term "locus" (plural—loci) refers to a position on a chromosome of a gene or other genetic element. Locus may also mean the DNA at that position. A variant of the DNA sequence at a given locus is called an allele. Alleles of a locus are located at identical sites on homologous chromosomes. A restriction locus is a locus that contains the recognition sequence of the restriction enzyme used in the assay. The term digested control locus as used herein refers to a genomic locus known to be unmethylated in all potential DNA categories. The term undigested control locus as used herein refers to a genomic locus that is either known to be methylated in all potential DNA categories, or is a genomic locus lacking the recognition sequence of the endonuclease used in the assay.

The term "natural DNA" or "natural nucleic acid" as used herein refers to, but is not limited to, nucleic acid which originates directly from the cells of a subject without modification or amplification.

The term "nucleic acid" as used herein refers to, but is not limited to, genomic DNA, cDNA, hnRNA, mRNA, rRNA, tRNA, fragmented nucleic acid, and nucleic acid obtained from subcellular organelles such as mitochondria. In addition, nucleic acids include, but are not limited to, synthetic nucleic acids or in vitro transcription products.

The term "nucleic-acid based analysis procedures" as used herein refers to any identification procedure which is based on the analysis of nucleic acids, e.g. DNA profiling.

The term "polymerase chain reaction (PCR) stutter" as used herein refers to PCR byproducts, obtained along with the main PCR product. These "stutter" byproducts are usually shorter by multiples of the repeated unit produced in the course of PCR amplification of STR sequences. The mechanism by which these artifacts are formed is understood, but it represents an intrinsic limitation of the PCR technology and therefore no effective remedy has been found to eliminate these spurious products (Olejniczak M, Krzyzosiak W J., Electrophoresis. 2006 October; 27 (19): 3724-34). The term "−1 stutter" as used herein refers to a stutter byproduct that is one repeat unit smaller than its associated allele. Similarly, "+1 stutter" refers to a stutter byproduct that is one repeat unit larger than its associated allele. The term '−1 stutter fraction' refers to the height (or area) of the −1 stutter peak divided by the height (or area) of the true allele peak. Similarly, "+1 stutter fraction" refers to the height (or area) of the +1 stutter peak divided by the height (or area) of the true allele peak.

The term "Restriction and Circularization-Aided Rolling Circle Amplification (RCA-RCA)" refers to a whole genome amplification procedure which retains the allelic differences among degraded amplified genomes while achieving almost complete genome coverage. RCA-RCA utilizes restriction digestion and whole genome circularization to generate genomic sequences amenable to rolling circle amplification.

The term "STR primers" as used herein refers to any commercially available or made-in-the-lab nucleotide primers that can be used to amplify a target nucleic acid sequence from a biological sample by PCR. There are approximately 1.5 million non-CODIS STR loci. Non-limiting examples of the above are presented in the website of the National Institute of Standards and Technology (NIST) that currently contains 3156 references for STRs employed in science, forensics and beyond. In addition to published primer sequences, STR primers may be obtained from commercial kits for amplification of hundreds of STR loci (for example, ABI Prism Linkage Mapping Set-MD10-Applied Biosystems), and for amplification of thousands of SNP loci (for example, Illumina BeadArray linkage mapping panel). The term "CODIS STR primers" as used herein refers to STR primers that are designed to amplify any of the thirteen core STR loci designated by the FBI's "Combined DNA Index System," specifically, the repeated sequences of TH01, TPDX, CSF1PO, VWA, FGA, D3S1358, D5S818, D7S820, D13S317, D16S539, D8S1179, D18S51, and D21S11, and the Amelogenin locus.

The term "signal ratio" as used herein refers to the ratio between the intensities of the signals obtained from amplification of two loci.

3. Methods for Distinguishing Between Natural and Artificial DNA Samples

In one aspect, the present invention provides a method for distinguishing between natural and artificial DNA samples. A general scheme of the invention is as follows: the method accepts as input a DNA sample. The DNA undergoes a procedure including one or more biochemical steps followed by signal detection. In the last step of the procedure, the signal is analyzed to determine whether the DNA is natural or artificial. In another aspect, the present invention provides a method for verifying that a DNA profile is of natural DNA. A general scheme of the invention is as follows: the method accepts as an input a DNA sample that underwent profiling (e.g. with Identifiler). The DNA sample undergoes a verification procedure which includes one or more biochemical steps followed by signal detection. In the last step of the entire procedure, data from both profiling and verification of the DNA sample are analyzed. The signal analysis determines whether the profile obtained from the DNA sample represents natural (in vivo) or artificial (in vitro) DNA.

In various aspects, the methods of the present invention concern the verification that DNA profiles represent natural DNA. The methods are employed on a DNA sample in question, for example, DNA from a blood sample found at a crime scene. The isolation of nucleic acids (e.g. DNA) from a biological sample may be achieved by various methods known in the art (e.g. see Sambrook et al, (1989) *Molecular Cloning: A Laboratory Manual*, 2nd ed. Cold Spring Harbor, New York). Distinguishing between natural and artificial DNA, or the determination whether a DNA profile represents natural DNA, may be accomplished using various strategies, including those described in the following sections.

4. Methylation

Methylation in the human genome occurs in the form of 5-methyl cytosine and is confined to cytosine residues that are part of the sequence CG (cytosine residues that are part of other sequences are not methylated).

Some CG dinucleotides in the human genome are methylated, and others are not. In addition, methylation is cell and tissue specific, such that a specific CG dinucleotide can be methylated in a certain cell and at the same time unmethylated in a different cell, or methylated in a certain tissue and at the same time unmethylated in different tissues. Since methylation at a specific locus can vary from cell to cell, when analyzing the methylation status of DNA extracted from a plurality of cells (e.g. from a forensic sample), the signal can be mixed, showing both the methylated and unmethylated signals in varying ratios. The inventors discovered that in some genomic regions all CG loci are constitutively methylated.

These regions are provided in Table 1 and in the section herein entitled Sequences. The inventors also discovered that in some genomic regions all CG loci are partially methylated. These regions are provided in Table 1 and in the section herein entitled Sequences. The inventors also discovered that in some genomic regions all CG loci are constitutively unmethylated. These regions are provided in Table 1 and in the section herein entitled Sequences. The inventors also discovered contiguous genomic regions containing constitutively methylated, partially methylated, and constitutively unmethylated CG loci. These regions are provided in Table 1 and in the section herein entitled Sequences. There are several different methods for determining the methylation level of genomic loci. Examples of methods that are commonly used are bisulfite sequencing, methylation-specific PCR, and methylation-sensitive endonuclease digestion. Further, various data sources are available for retrieving or storing DNA methylation data and making these data readily available to the public, for example MetDB (http://www.methdb.net).

Exemplary methods for determining the methylation level of nucleic acids include, but are not limited to the following methods:

Bisulfite Sequencing.

Bisulfite sequencing is the sequencing of bisulfite treated-DNA to determine its pattern of methylation. The method is based on the fact that treatment of DNA with sodium bisulfite results in conversion of non-methylated cytosine residues to uracil, while leaving the methylated cytosine residues unaffected. Following conversion by sodium bisulfite, specific regions of the DNA are amplified by PCR, and the PCR products are sequenced. Since in the polymerase chain reaction uracil residues are amplified as if they were thymine residues, unmethylated cytosine residues in the original DNA appear as thymine residues in the sequenced PCR product, whereas methylated cytosine residues in the original DNA appear as cytosine residues in the sequenced PCR product.

5. Methylation-Specific PCR

Methylation specific PCR is a method of methylation analysis that, like bisulfite sequencing, is also performed on bisulfite-treated DNA, but avoids the need to sequence the genomic region of interest. Instead, the selected region in the bisulfite-treated DNA is amplified by PCR using two sets of primers that are designed to anneal to the same genomic targets. The primer pairs are designed to be "methylated-specific" by including sequences complementing only unconverted 5-methylcytosines, or conversely "unmethylated-specific," complementing thymines converted from unmethylated cytosines. Methylation is determined by the relative efficiency of the different primer pairs in achieving amplification.

It should be understood in the context of the present invention that methylation specific PCR determines the methylation level of CG dinucleotides in the primer sequences only, and not in the entire genomic region that is amplified by PCR. Therefore, CG dinucleotides that are found in the amplified sequence but are not in the primer sequences are not part of the CG locus.

6. Methylation-Sensitive Endonuclease Digestion

Digestion of DNA with methylation-sensitive endonucleases represents a method for methylation analysis that can be applied directly to genomic DNA without the need to perform bisulfite conversion. The method is based on the fact that methylation-sensitive endonucleases digest only unmethylated DNA, while leaving methylated DNA intact. Following digestion, the DNA can be analyzed for methylation level by a variety of methods, including gel electrophoresis, and PCR amplification of specific loci.

In the procedure based on methylation-sensitive endonuclease digestion, each CG locus is comprised of one or more CG dinucleotides that are part of recognition sequence(s) of the methylation-sensitive restriction endonuclease(s) that are used in the procedure. CG dinucleotides that are found in the amplified genomic region, but are not in the recognition sequence(s) of the endonuclease(s) are not part of the CG locus.

In one embodiment, the one or more CG loci that are detected are partially methylated in natural DNA, but would be unmethylated in artificial DNA. Partial methylation would be expected to result in a mixture of T and C at the position being interrogated. Hybridization would be observed to both the T specific probes/primers and the C specific probes/primers, similar to detection of a heterozygous SNP. Relative amounts of hybridization may be used to determine the relative amount of methylation. Alternatively, both C and T would be observed upon bisulfite sequencing. Alternatively, fluorescent signals corresponding to amplification products of methylated or partially methylated CG loci can be detected.

7. Overview of the Present Signal Ratio Assay

As mentioned above, one particular assay of the present invention involves the quantitative comparison of intensity of the signals from a pair of locus-specific amplification products produced by performing a Polymerase Chain Reaction on restriction-digested DNA. See FIG. 1A,B. The numerical ratio of intensities corresponds to the category of the template DNA, for example whether the DNA sample was extracted from semen or from a non-semen tissue. For example, in one embodiment, locus 1 and locus 2 can be amplified using fluorescently labeled primers, separated by electrophoresis, and the intensity of the signals is the relative fluorescence units (rfu) of peaks corresponding to the loci. See FIG. 1B,C. The intensity of the signals will correspond to the successfulness of amplification of locus 1 and locus 2 from the source DNA template. By comparing rfu between the two amplification products one can calculate a signal ratio—a ratio that reflects the ratio of the quantities of the amplification products.

In addition, however, one aspect of this assay includes the predetermination of the expected signal ratios from various types of DNA categories. Thus, the template DNA that is subject to analysis is first digested with a methylation-sensitive restriction endonuclease before it is cycled through the quantitative-styled PCR amplification protocol. If the level of methylation at the site/s of the restriction recognition sequence/s in the pair of the two loci in the various categories of DNA is known, the skilled person can predict the expected signal ratios of amplification products of the pair of loci in the respective categories. Alternatively, if the levels of methylation are unknown, the skilled person can nonetheless empirically determine the signal ratios between a pair of genomic loci in the various categories of DNA by performing the assay on samples from known categories.

With this premise, the present inventive assays comprise digesting a DNA sample with a methylation-sensitive and/or methylation dependent enzyme, performing a PCR amplification reaction on the digested DNA, and determining the intensity of the signals from locus-specific amplification products. As mentioned, the intensity of signals can be quantified or measured by using fluorescent PCR. Determination of the category of the DNA sample is performed by comparing the observed signal ratios to reference ratios obtained from DNA samples of known categories, and determining which category corresponds best to the observed ratios.

This particular signal ratio assay is not reliant upon identifying or obtaining measurements of the absolute methylation fraction or level of selected loci. In addition, this particular signal ratio assay is not reliant upon the efficiencies of the primer pairs used, does not necessitate that both primer pairs have similar efficiencies, is not reliant upon amount of input template DNA, is not reliant upon specific thermocycler machine and reaction conditions. Rather, the assay determines the ratio between two signals which correspond to the ratio of methylation levels in the different loci. By this manner, the quantity or concentration of starting DNA material in the sample is irrelevant to the analysis and does not skew the output results. That is, the ratio of signal levels between a first locus and a second locus will remain constant regardless of how much DNA is used as a template for PCR and regardless of the number of amplification cycles that are run on the thermocycler. For example, a signal ratio of 10 between loci 1 and 2 will remain the same whether the input DNA represents methylation levels of 0.9 and 0.09 (90% methylation in locus 1 and 9% in 2), or 0.5 and 0.05 (50% methylation in locus 1 and 5% in 2), etc. In another example, a signal ratio of 10 between loci 1 and 2 will remain the same regardless of the amount of DNA template used in the reaction.

The fact that the inventive assay does not depend on determination of methylation levels at any genomic locus, and does not require any external control, allows the assay to be more accurate, cost effective, and applicable to samples with low amounts of DNA.

In the context of forensic tissue identification, the inventive assay represents a standardized procedure which is identical regardless of the specific tissue identification task that is being performed (except for the use of panel-specific primers), that requires only standard forensic procedures and equipment, thus enabling the assay to be automated and easily integrated into forensic labs.

Furthermore, the setup of the inventive assay makes possible combining tissue identification and DNA profiling into a single assay.

The fact that the inventive assay performs digestion and amplification in the same reaction minimizes the complexity (the number of required tubes and pipetting steps of the assay), thereby minimizing the risk of contamination and/or error.

This inventive assay therefore provides a useful biochemical marker in the form of, in one example, a numerical ratio, that can be used to differentiate between natural DNA and artificial DNA that was synthesized in vitro such as by PCR, chemical synthesis, or multiple displacement amplification (MDA). More particular details of this exemplary assay follow.

8. Characteristics of Primers for Locus-Specific Amplification

Accordingly, an aspect of the present invention concerns obtaining a "signal ratio" in which the fluorescence intensities of multiple DNA loci amplification products produced from fluorescent PCR are compared to one another in order to calculate ratios between successive pairs of loci, e.g., Loci #1 vs. Loci #2; Loci #1 vs. Loci #3; Loci #1 vs. Loci #4; Loci #2 vs. Loci #3, Loci #2 vs. Loci #4, and so on. When this technique is used to test the natural vs. artificial nature of a DNA sample, the primers that are used in the signal ratio amplification reactions are chosen so as to amplify a pair of loci that are differentially methylated in natural DNA (e.g. the first is 90% methylated and the second is 30% methylated in natural DNA).

One consideration for selecting which two pairs of primers (a first pair and a second pair) to use to amplify two loci (1) and (2) is the degree to which the two loci are differentially methylated in in vivo DNA. Thus, a pair of loci in which locus (1) is more methylated in comparison to locus (2), are examples of loci that can be used to design primers for the signal ratio amplification assay.

9. Selection of Genomic Loci

1. Selection of putative loci can be performed in any of three modes:

(i) Select a locus closest to the transcription start site of a gene that has been shown in the literature to be differentially expressed (mRNA data) in the relevant categories (e.g. different tissues).

(ii) Select a locus that has been shown in the literature to be differentially methylated between different categories (e.g. tissues).

(iii) Select a random genomic locus.

2. Design primers for putative loci.

3. Empirically test "informativeness" of putative loci. For each putative locus calculate the signal ratio between the putative locus and another putative locus, or alternatively, between the putative locus and an undigested control locus.

4. Choose "informative" loci (i.e. loci whose signal ratios are significantly different in the different DNA categories) for use in the assay.

10. Methylation-Sensitive Restriction Endonucleases

A second consideration of the present inventive method is the selection of loci that are or are not cut or digested by a methylation-sensitive and/or methylation-dependent restriction endonuclease, depending on their methylation status. The endonuclease is selected if, for instance, it is unable to cut the DNA strand if its recognition sequence in that locus is methylated. Thus, in the context of locus (1), which is methylated, and locus (2), which is not methylated, an endonuclease like HhaI or HpaII will not digest locus (1) but will digest locus (2). Accordingly, the selection of loci for amplification in the signal ratio assay may also take into account the presence of methylation-sensitive restriction endonuclease recognition sequences within each locus.

Forward and reverse primers can then be designed to anneal to a region of DNA that flanks the recognition sequence of the loci.

Accordingly, in the case of a methylation-sensitive enzyme, if a locus is methylated it will (A) not be digested but (B) it will be amplified. Conversely, if a locus is unmethylated, it will (A) be digested but (B) not amplified. In the case of a methylation-dependent enzyme, the situation is vice versa.

11. Advantages of the Signal Ratio Assay

The signal ratio assay of the present invention has several advantages and benefits over other approaches for analyzing methylation, and therefore the skilled person would appreciate the various advantageous uses to which this signal ratio assay can be put. For instance, this assay is insensitive to various "noise" factors inherent when relying on the absolute intensity level of an amplicon signal that fluctuates as a consequence of changes in template DNA concentration, thermocycler manufacturer, and PCR conditions, and presence of inhibitors. Instead, the presently-calculated methylation ratio does not depend on such factors, since the two analyzed loci are co-amplified in the same reaction and are therefore subject to the effects of such disparities. Thus, the present inventive method does not require absolute quantification of genomic targets or amplicons; and the assay is a single stand-alone reaction with no need for a standard curve or any external controls.

The signal ratio can be performed on very small quantities of DNA in a single biochemical reaction and is therefore an inexpensive, rapid, and powerful method for establishing, for example, whether a sample contains natural or artificial DNA. An important feature of the design of the inventive methods is that it can be combined with other PCR-based procedures, such as DNA profiling, in a single biochemical reaction.

12. Capillary Electrophoresis and Multiplexing

The rapidity of the analysis is evident in consideration of the use of, for instance, capillary electrophoresis to separate numerous amplification products produced from the amplification of multiple pairs of target loci. As described above the present signal ratio assay can be performed on multiple loci, and in each case a signal ratio is calculated for each pair of loci separately. For example, if four loci (A,B,C,D) are co-amplified in the reaction, six different signal ratios can be calculated, i.e.: A/B, A/C, A/D, B/C, B/D, C/D.

Accordingly, if "n" loci are co-amplified, then $(n^2-n)/2$ different ratios can be calculated. Therefore, the amount of information that is provided by the present methylation assay rises exponentially with the number of analyzed loci. Capillary electrophoresis, as opposed to real-time PCR amplification methods, can distinguish between a large number of loci in a single run. For example, for DNA profiling, 17 genomic loci are routinely co-amplified from a particular DNA sample, and analyzed together. As a consequence, the performance of the present signal ratio assay on all 17 loci yields 136 independent signal ratios. Real-time PCR cannot simultaneously distinguish in a single reaction those numbers of discrete amplification products necessary to produce 136 ratios. About four loci can by distinguished by real time PCR, which corresponds to the calculation of only six ratios.

By contrast, capillary electrophoresis can readily separate out amplification products from all paired permutations of 17 loci and can therefore readily produce data to simultaneously calculate all 136 signal ratios in a single reaction. Theoretically, hundreds of loci can be run together and separated in a single capillary electrophoresis run. In order to facilitate analysis of multiple ratios, it can be advantageous to calculate a single score, herein termed "Combined Signal Score" (CSS), from these ratios. The CSS can then be used, for example, in order to ascertain whether the source DNA sample is natural or artificial.

13. Sequences

The sequences provided herein for the various CODIS, PowerPlex® 16, and other loci commonly used for profiling, i.e., SEQ ID NOs. 1-25 are of genomic loci commonly used for STR profiling., have been analyzed herein to determine (1) the position of every cytosine-guanine (CG) dinucleotide, (2) the methylation level of all CG dinucleotides in the locus in natural DNA, and (3) the methylation sensitive and methylation dependent restriction enzyme profile for that particular locus. The sequence listing included within the text of this application therefore provides guidance to the skilled person in the identification of particular methylation-sensitive and methylation-dependent restriction endonucleases that can be used in accordance with the inventive ratio-generating assay methods. For example, SEQ ID NO. 8, which is the 751-long nucleotide sequence for the "vWA" CODIS and PowerPlex® 16-amplified locus, comprises only one CG dinucleotide at position 571. That CG and the nucleotides that immediately flank it, provide the recognition sequence for enzymes BssKI, HpaII, Nt.CviPII, and SEQ ID NOs 26-32 are genomic loci that have been found by the inventors to produce signal ratios with significantly different values between natural and artificial DNA samples. SEQ ID NOs 33-54 are genomic loci that have been found by the inventors to produce signal ratios with significantly different values (based on the Kolomogorov-Smirnov test using a threshold of p=0.05) between samples of DNA extracted from different tissues.

The sequence information provided herein also permits the skilled artisan to design forward and reverse amplification primers that anneal to regions of a selected locus that flank the CG and restriction site. Thus, the present invention is not limited to the amplification of, for instance, CODIS loci, using only those commercially available primers, although the use and availability of commercially available primers can be a more convenient and cost-effective option for performing the present inventive authentication assays.

14. Algorithm and Software

In one embodiment, calculation of signal ratios and/or representation ratios (for example in order to determine whether a DNA profile represents natural DNA) is performed based on analysis of the signal intensities of amplification products of fluorescent PCR that are run on a capillary electrophoresis machine. The output of the capillary electrophoresis machine is a binary computer file (for example, an FSA file in the case of capillary electrophoresis machines of Applied Biosystems). This file includes information regarding the capillary electrophoresis run, including the channel data, which is the relative fluorescent units (rfus) of each fluorophore as a function of each sampling time point (called datapoint).

The present invention also describes a software program that accepts as input a file that is the output a capillary electrophoresis machine run, and calculates the fluorescence intensities of a set of loci whose amplification products were run on the capillary electrophoresis machine. Based on these intensities, the software calculates signal ratios and/or representation ratios (or combined scores based on these ratios), based on a set of predefined pairs of loci for which the ratios are defined to be calculated. Finally, the software outputs a decision based on the comparison of the calculated ratios to predefined thresholds.

Following is a scheme of this analysis performed by the software program:

1. Subtract from the signal of each dye channel the baseline level, defined as the mean rfu level of that channel in the range 400-500 bps, and remove spectral overlap between fluorophores based on the matrix obtained from the spectral calibration procedure of the capillary electrophoresis machine.

2. Obtain the rfu level of each analyzed locus, defined as the maximal rfu level in the range −0.5 bp to +0.5 bp of the expected size of the locus.

3. Calculate signal ratios between a set of pairs of loci, defined as the ratio between the rfu levels of the first and second loci in the pair (to avoid division by zero assign a level of 50 rfus to all loci with rfu levels below 50).

4. For each ratio calculated in step 3 and for each tissue type calculate a Probability Score, defined as the value of the reference probability function (see below) at the observed ratio.

5. For each tissue type, calculate a Combined Probability Score, defined as the product of the separate Probability Scores for that tissue obtained in step 4 (where n is the number of signal ratios).

6. For each tissue type, calculate a Likelihood Score (representing the likelihood that the DNA sample originated from that tissue), defined as the ratio between the Combined Probability Score of the tissue and the sum of the Combined Probability Scores of all tissues. The tissue with the highest Likelihood Score is considered the source tissue of the sample.

15. Reference Probability Functions

The reference probability function of a certain pair of loci in a certain tissue is the gamma distribution function fitted to the set of signal ratios observed in samples of natural DNA of that tissue type.

16. Correction for Incomplete Digestion

Since incomplete digestion of template DNA might occur as a result of the presence of inhibitors in the sample, it is useful to incorporate into the assay an analysis of actual digestion level. This can be achieved by incorporation of at least one "digested control locus" and at least one "undigested control locus." A digested control locus is a genomic locus known to be unmethylated in natural DNA in all potential tissues. An undigested control locus is a locus that is either known to be methylated in natural DNA in all potential tissues, or is a locus lacking the recognition sequence of the endonuclease used in the assay. The signal ratio between a digested control locus and an undigested control locus is correlated to the actual digestion level in the assay. The algorithm can make use of such loci by checking whether adequate digestion occurred (and if not—aborting analysis), and by modifying actual rfu levels of loci to values representing rfu values that would have been obtained had complete digestion occurred. If this modification is performed, then signal ratios are calculated from the modified rfu values.

EXAMPLES

Materials and Methods

A. Collection of Biological Tissues

Blood (venous/menstrual), saliva, semen, skin epidermis, urine, and vaginal secretion were collected from volunteers. Informed consent was obtained from all participants recruited into the study.

B. DNA Extraction and Quantification

DNA was extracted from all samples using by organic extraction. The quantity of recovered DNA was determined using the Quantifiler® Human DNA quantification kit (Applied Biosystems) and the 7300 Real-Time PCR system (Applied Biosystems).

C. Selection of Genetic Loci and Primer Design

Random CpG islands (defined as a region $>=200$ bp and with a GC content$>=0.5$ and with at least 8 CGs; corresponding to observed/expected CpG ratio$>0.6$) were searched using a software program developed for this task. From these, CpG islands that contained a HhaI recognition sequence were selected for initial screening. Primers (18-28 bps) flanking the HhaI recognition sequence were designed with a Tm of 64-66° C. and for amplicon sizes of 66-150 bps. Fluorescently-labeled forward primers (FAM or JOE) were purchased from Integrated DNA Technologies. Loci were screened in pairs for differential methylation by comparing signals obtained from amplification of pooled DNA samples (each containing DNA from 10 individuals) of each tissue type. Loci that showed significant differential amplification patterns (defined as the largest signal ratio observed in all tissue types being greater that three times the smallest ratio observed) were selected for multiplexing. In total, 205 genomic loci were screened of which 38 showed significant differential amplification patterns. From these, 16 loci were used in the experiments. For the stand-alone tissue identification assay, 15 loci that could be co-amplified without significant noise were used. For the combined semen detection and profiling assay two loci (L68346 which was also used for the stand-alone assay and L16264) were used.

D. Endonuclease Digestion, PCR, and Capillary Electrophoresis

In stand-alone assay experiments, each DNA sample was digested by HhaI and subjected to PCR amplification in the same reaction, consisting of 30 U HhaI (New England Biolabs), 2.5 U AmpliTaq Gold (Applied Biosystems), 2.5 µg BSA (New England Biolabs), 0.2 mM each dNTP, 0.1-0.3 µM each primer, 2.5 µl reaction buffer (150 mM Tris-Hcl, 15 mM $MgCl_2$) and DDW to a total volume of 25 µl. The reaction composition in the combined tissue identification-profiling experiments was the same as in the stand-alone assay except for the primers, which were 0.2 µM each semen identification primer together with 5 µl Primer Set of ProfilerPlus (Applied Biosystems). Reactions (for both stand-alone and combined assay) were performed in a GeneAmp® PCR System 9700 (Applied Biosystems), and the thermocycling program used was: 37° C. for 15 min, 95° C. for 11 min, followed by 28 cycles of 94° C. for 1 min, 59° C. for 1 min, 72° C. for 1 min, and followed by a final extension step of 60° C. for 45 min. A mix containing 1.5 µl of amplification products, 24.5 µl HiDi formamide (Applied Biosystems) and 0.5 µl ROX size standard (Applied Biosystems) was denatured (95° C. for 3 min immediately followed by 3 min on ice), and run on an ABI 310 Genetic Analyzer (Applied Biosystems) according to the manufacturer's instructions. All resulting electropherograms were analyzed using in-house developed software, and electropherograms resulting from combined tissue identification-profiling experiments were also analyzed using GeneMapper ID-X analysis software (Applied Biosystems).

E. Tissue Identification Assay—Data Analysis

Data analysis for tissue identification was performed by an in-house developed software that accepts as input fsa files and outputs the most likely source tissue. Derivation of semen percentage in mixture samples was performed based on profiling loci and tissue identification loci. Derivation based on profiling loci was performed by dividing the sum of rfu values of alleles corresponding to the contributor of the semen by the total sum of rfu values of all alleles in STR loci that had 4 genotyped alleles. Derivation based on tissue identification loci was performed first by calculating the expected signal ratio for all possible percentages of mixtures (from 0 to 100% with 1% increments, based on the signal ratio of undigested DNA), and the algorithm provided the percentage of semen for which the expected signal ratio is closest to the observed signal ratio.

F. Simulation of Degraded Samples

Twenty nanograms of each sample were digested for 10 min at 37° C. with 0.01 U DNAseI (Ambion), 2 µl 10× DNAseI buffer (Ambion) in total reaction volume of 20 µl, followed by heat-inactivation at 75° C. for 10 min. One nanogram of each digested DNA sample was then subjected to the combined tissue identification-profiling assay.

Example 1

Categorization of DNA According to Tissue Type—Stand Alone Assay

In this example, the categorization procedure is termed "tissue identification assay." The tissue identification assay uses a panel of loci that are differentially methylated between tissues to determine the most probable source tissue of a DNA sample as shown in Table 1 (FIG. 7). A scheme of the assay is presented in FIG. 1A. One nanogram of DNA from a forensic sample in question is digested with the HhaI methylation-sensitive restriction enzyme, which cleaves DNA at its recognition sequence GCGC only if it is unmethylated (while leaving methylated targets intact). A panel of tissue identification loci is then amplified by PCR from the digested DNA using fluorescently-labeled primers, and an aliquot of amplified products is separated by capillary electrophoresis. Loci with higher methylation levels are amplified with higher efficiency (because more DNA molecules are protected from digestion), producing a relatively strong signal in the electropherogram (FIG. 1B, locus A). Conversely, loci with a lower methylation level are amplified with lower efficiency, yielding a relatively weak signal in the electropherogram (FIG. 1B, locus B).

Automated signal analysis software enables analysis of an output electropherogram, and assigns heights (in rfu) to amplicons corresponding to tissue identification loci. Although the height of a single locus is correlated with its methylation level, the actual methylation level cannot be derived, because that level also depends on the precise template concentration and specific PCR conditions. Instead, ratios of methylation levels between co-amplified loci can be calculated, since all the loci are subjected to the same template concentration and specific reaction conditions. Therefore, for each pair of loci a signal ratio, defined as the ratio between the heights of the first and second loci, is calculated, and this ratio reflects the ratio between the methylation levels of the corresponding loci. All calculated signal ratios are combined into a single vector (if, for example, in a 15-loci panel the vector contains 105 ratios—between locus 1 and 2, locus 1 and 3, etc.), which is then compared to a database of reference vectors obtained from a data set of samples of known tissue origin. The tissue identification algorithm calculates for each potential tissue source a likelihood score, reflecting the likelihood that the DNA sample originated from that tissue, and the output of the algorithm is the most likely tissue.

Figure 4:
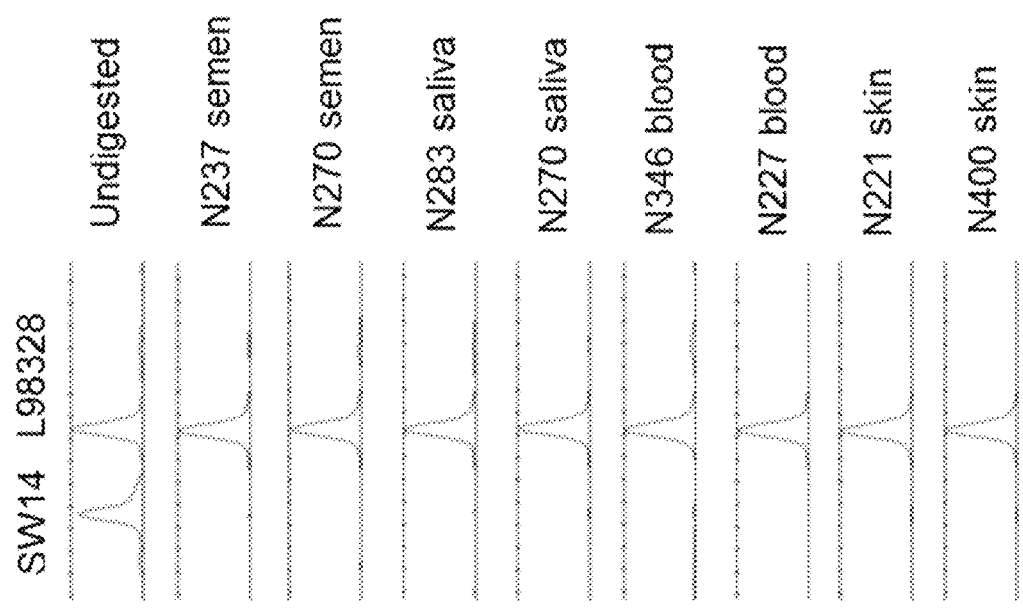
FIG. 4. Assessment of HhaI digestion. DNA samples of different sources were subjected to the same single digestion-amplification reaction used in the tissue identification experiments. In this experiment, the panel of loci consisted of two loci: an undigested control locus (L98328) that lacks an HhaI site and a digested control locus (SW14) thath is unmethylated in these tissues. All samples showed presence of the undigested control locus and complete absence of the digested control locus, indicating complete digestion by HhaI in contrast to the undigested sample which showed presence of both loci.

A stand-alone tissue identification assay was performed on 50 samples: 14 blood, 14 saliva, 11 semen, and 11 skin epidermis using a panel of 15 tissue identification loci, ranging in amplicon size from 66 to 150 bps. FIG. 2 depicts electropherograms of eight of these samples—two of each tissue type. Although samples of the same tissue type from different individuals were not completely identical (due to natural variability of methylation levels and stochastic PCR effects), it was nevertheless evident that each tissue type had a distinct methylation profile. For example, the ratio of L91762/L68346 in semen samples ranged from 0.04-0.53 and was higher in all other tissue samples (2.15-18.28; Table 2 in FIG. 8), and therefore a low L91762/L68346 ratio was distinctive of semen samples. The ratio of L76138/L26688 was low in blood and saliva (0.08-1.54) and higher in semen and skin epidermis (2.04-19.56; Table 2 in FIG. 8); therefore a high ratio of L91762/L68346 concomitant with a high ratio of L76138/L26688 was distinctive of skin epidermis samples. The tissue identification algorithm correctly identified the true tissue source of all 50 samples. Further analysis of the data using subsets of tissue identification loci revealed that the full set of 15 loci was redundant and 100% identification was achieved by using only 7 out of the 15 loci (L91762, L68346, L50468, L14432, L30139, L15952, and L26688). Because tissue identification relies on efficient digestion, complete digestion of template DNA by HhaI was assessed in a single digestion-amplification reaction setup. The 50 DNA samples were subjected to the same procedure but using a panel of two different loci as shown in Table 3 (FIG. 9)—a control locus without a HhaI site (L98328) and a locus which was previously shown to be completely unmethylated in these tissues (SW14; see D. Frumkin et al., Authentication of forensic DNA samples, Forensic Sci. Int. Genet. 2009, doi: 10.1016/j.fsigen.2009.06.009, which is incorporated herein by reference). All samples showed presence of the reference locus and complete absence of SW14, indicating complete digestion by HhaI in contrast to the undigested sample which showed presence of both loci (example runs are shown in FIG. 4).

Example 2

Analysis of Noise Factors Affecting Signal Ratios

The assay described in example 1 is based on utilizing loci that are differentially methylated between tissues, for which signal ratio values are generally tissue-specific (FIG. 1C). However, even in differentially methylated tissues, there potentially could be some overlap in the observed signal ratios as a result of natural variability in methylation levels among different individuals and/or artifacts associated with the PCR such as differences in DNA template concentration (e.g. as a result of pipetting errors and stochastic effects). The effect of each of these "noise" factors was analyzed in relation to the "signal," which is the average signal ratio difference between tissues. Two loci with an average 10-fold difference in signal ratio values between semen and blood were selected. Different PCRs were performed on the same semen sample using 1 ng and 2 ng DNA as template. The ratios obtained from these amplifications were compared to each other and to ratios obtained from amplification of different blood samples. The differences between the ratios obtained in different PCRs and using different amounts of input DNA were more than one order of magnitude smaller than the differences between the ratios obtained from the different tissues (FIG. 1D).

Example 3

Combined Semen Detection and DNA Profiling

In this example categorization of the DNA is into one of two categories: semen and non-semen where non-semen refers to all tissues except semen. The categorization is performed together with DNA profiling in the same reaction.

Figure 3A:
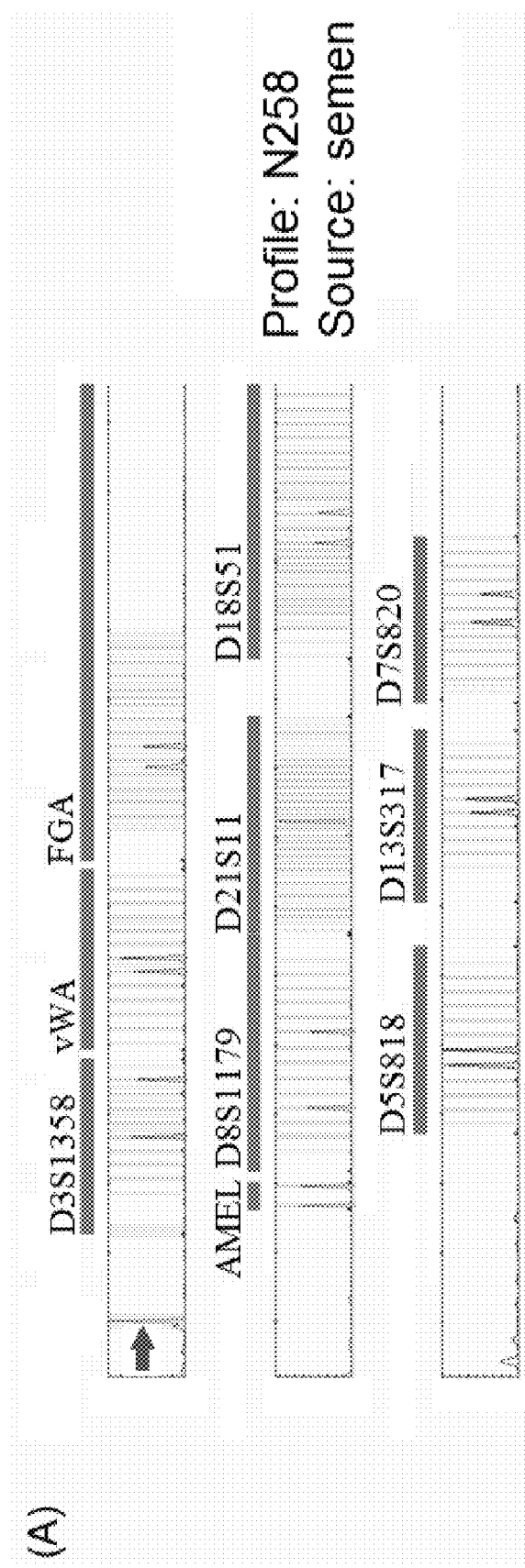
FIGS. 3A-D. Combined semen detection and DNA profiling. (A,B) Electropherograms of the combined assay performed on a semen (A) and urine (B) sample from the same individual. The ProfilerPlus profiles of the samples are identical, and the differences in tissue source are indicated by the differential amplification of two semen detection loci (arrows). (C) FAM channel data of the combined assay performed on samples from different tissue types. The signal ratio between the semen detection loci (arrows) is 25.04 in the semen sample, and less than 0.1 in all other tissue types. The top panel includes undigested DNA for reference. (D) FAM channel data of the combined assay performed on mixtures of semen and saliva (from different individuals) with various ratios. The signal ratio is correlated to the percentage of semen in the mixture.
Figure 3B:
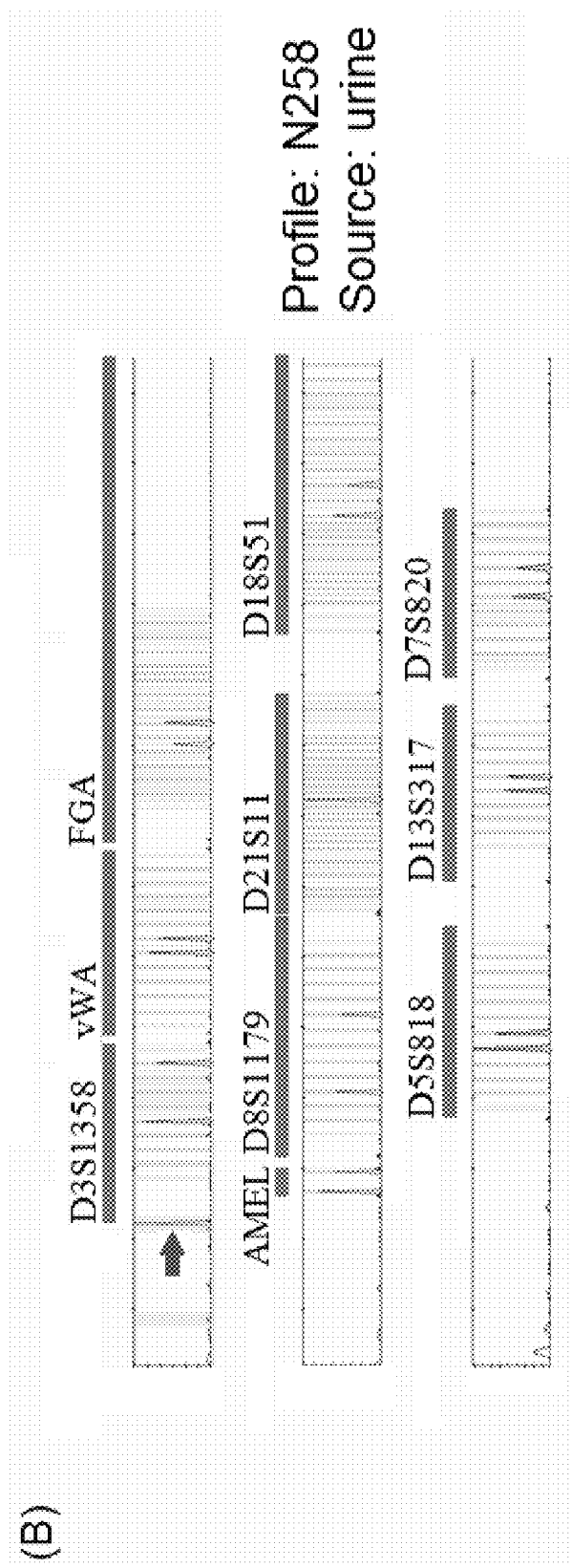
Figure 3C:
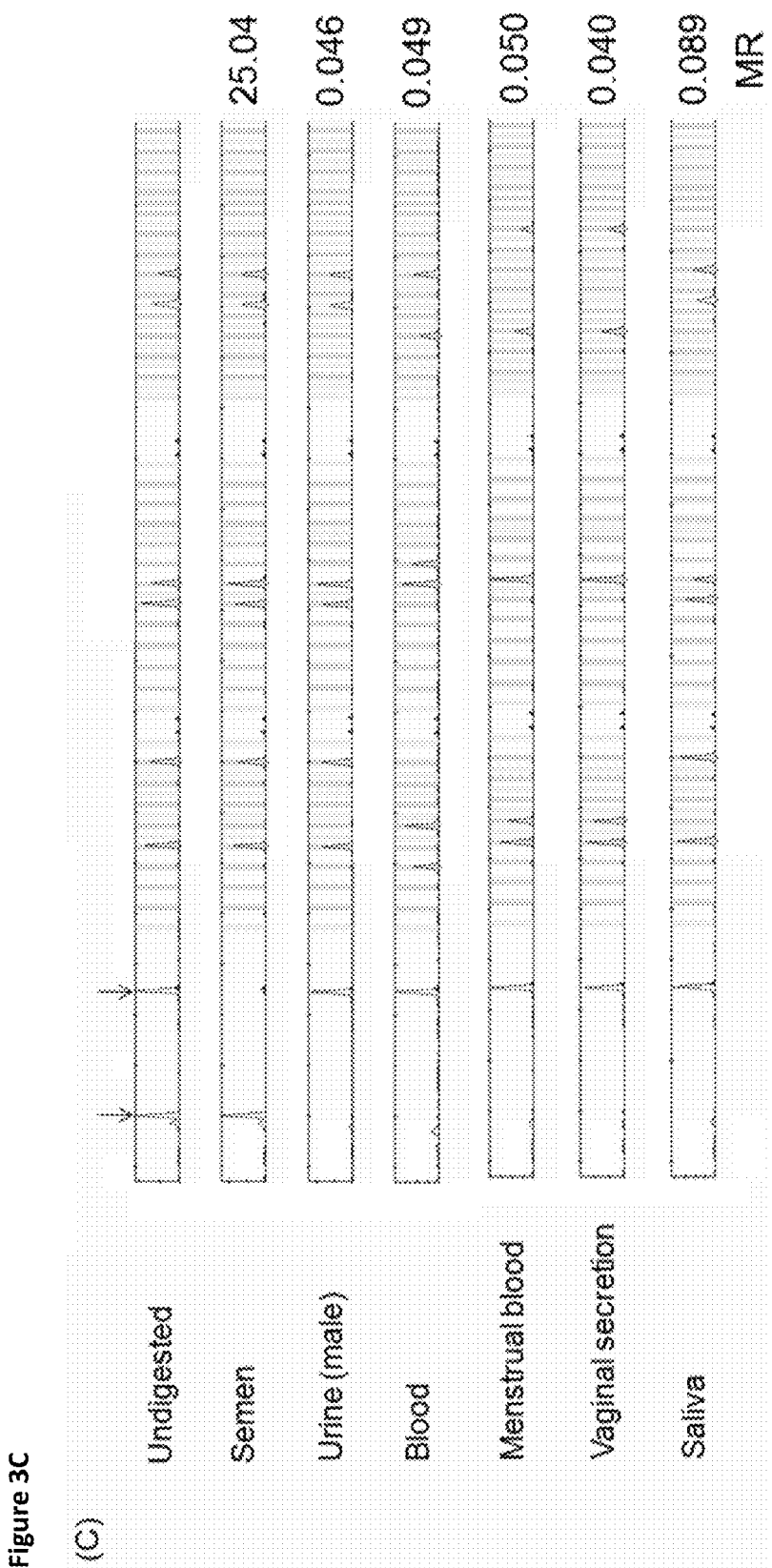
Figure 3D:
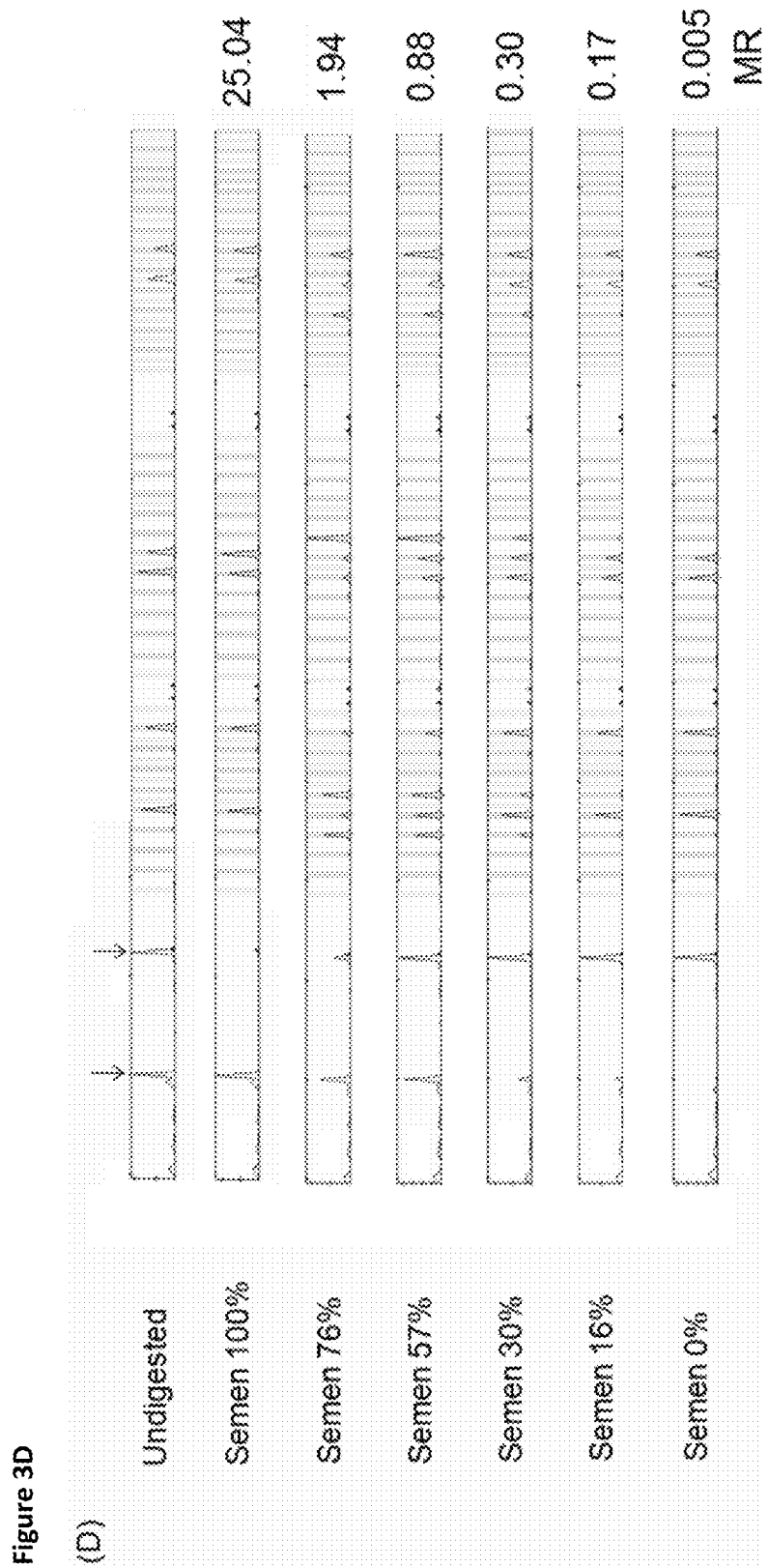

The tissue identification procedure utilizes the same platforms used in standard STR profiling (i.e. thermocycler and capillary electrophoresis instruments) and is therefore readily amenable to integration with DNA profiling in a single reaction. This capability was demonstrated by generating an integrated STR profiling and semen detection assay. A STR profiling kit (Profiler Plus) PCR was supplemented with primers specific for two semen identification loci (Table 4 in FIG. 10). These loci consist of a 70 bps amplicon which is efficiently amplified only in semen and a 95 bps amplicon which is efficiently amplified in all tissues except semen. The assay was tested on pure samples of semen, urine (male), venous blood, menstrual blood, vaginal secretion, and saliva. The correct pattern of semen identification amplification was observed and the tissue identification algorithm correctly identified presence/absence of semen in all samples. FIGS. 3A and B depict complete electropherograms of semen and urine samples (obtained from the same individual), and FIG. 3C depicts FAM channel data from all samples including the two semen identification loci and three profiling loci. The observed signal ratio was 25.04 in the semen sample, and 0.04-0.089 in the other samples. The combined assay was also tested on mixtures of semen and saliva at various ratios (FIG. 3D). For each of these mixtures the percentage of the semen in the sample was derived from the signal ratio of the semen identification loci and compared with the corresponding percentage derived from the profiling loci (the semen and saliva samples were obtained from different individuals and could therefore be differentiated based on STR loci). The percentages derived were comparable, with a maximum difference of 10% (Table 5 in FIG. 11). Moreover, the presence vs. absence of semen was correctly determined in all samples (including a sample that contained only 13% semen; FIG. 3D). The STR profiles obtained from the samples using the integrated profiling-semen detection assay were identical to profiles obtained from the same samples using ProfilerPlus (without semen detection).

Example 4

Categorization of Aged and Degraded DNA Samples

Figure 5:
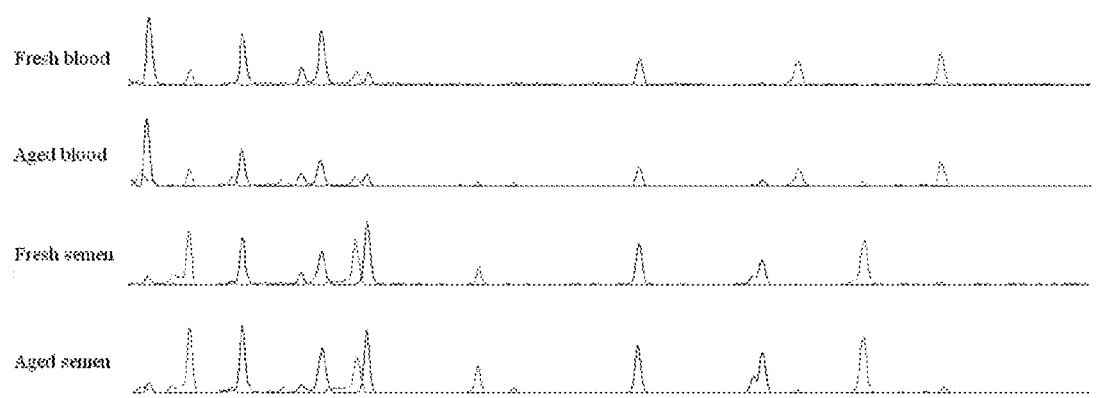
FIG. 5. Aged samples. The stand-alone tissue identification assay was tested on DNA samples extracted from 20-month old stains of blood and semen. Both samples amplified well, similar to their fresh counterparts, and their source was correctly identified by the analysis software.

The stand-alone tissue identification assay (described in example 1) was tested on two DNA samples extracted from 20-month old stains (blood and semen on cotton) as a proof-of-concept for application to forensic-type samples. Both samples amplified well, similarly to fresh samples (FIG. 5), and the algorithm correctly identified the tissue source of both samples. In order to simulate degraded DNA samples, two additional DNA samples (blood and semen) were subjected to digestion with DNAseI under conditions that yield partial digestion. These samples were then analyzed with the combined semen detection and profiling assay. DNAseI digestion resulted in dropout of alleles in the larger STRs in both samples such that their profiles were partial. In the blood sample only D3S1358 and Amelogenin alleles were typed, and in the semen sample dropout of alleles was observed in FGA, D21S11, D18S51, D13S317 and D7S820 (FIG. 6). The smaller tissue identification loci amplified successfully with the expected pattern, and the algorithm correctly identified the presence/absence of semen in these samples.

Example 5

Combined Profiling and Categorization of DNA

This particular assay employs both conventional profiling of a DNA sample (with the Promega PowerPlex16 kit), and categorization of DNA into categories of natural vs. artificial.

One aspect of this assay, therefore, is to check the natural nature of the DNA against several or all types of artificial DNA (see the Definitions section), and therefore contains an analysis of several different ratios. The combination of ratios makes it possible to therefore compare a single parameter various DNAs synthesized from various methods. A single parameter, for example representation ratio, can distinguish between a sample that contains the entire genome (natural DNA but also MDA synthesized DNA—as in this example) and a sample that contains only a subset (for example, only CODIS loci).

Two samples of DNA were analyzed—a natural DNA sample extracted from the blood of subject A, and an artificial DNA sample synthesized by in vitro multiple displacement amplification using a commercial kit (from a minute amount of subject A's real DNA as template).

The two samples were first profiled with a conventional kit (PowerPlex16) and analyzed using a conventional profiling software (GeneMapperID-X). The scheme of this procedure can be briefly described as performing multiplex PCR using the PowerPlex16 primer mix on a DNA sample; separating the amplification products on a capillary electrophoresis machine; and then analyzing the output data with, for instance, the GeneMapperID-X software.

For each sample, the end product of this assay is a profile. The profiles of the two samples are identical, as can be seen in FIG. 9A,B. Furthermore, the GeneMapperID-X software determined the profiles of both samples to be single contributor (i.e. from a single person) profiles, with no anomalies. This shows that a profile obtained from artificial DNA can be identical to a profile obtained from natural DNA. See D. Frumkin, et al., *Authentication of forensic DNA samples*, Forensic Sci. Int. Genet. (2009), doi:10.1016/j.fsigen.2009.06.009, which is incorporated herein by reference.

Both samples of DNA were subsequently also analyzed by a combined profiling and categorization assay based on the following scheme: digest a DNA sample with HhaI and perform multiplex PCR using the PowerPlex16 primer mix with the addition of primers for amplifying an additional locus, such as Hypo23; separating the amplification products on a capillary electrophoresis machine; and analyzing the output data with the capillary analyzer software, such as the software algorithm disclosed herein.

For each sample, the end product of this assay is a profile and assignment of category. As can be seen in FIGS. 9 C and D, the natural DNA was assigned as "natural," in contrast to the artificial sample which was assigned as "artificial."

In this example, the assignment of category was performed by analysis of three parameters:

SR1 (signal ratio of TPOX/D8S1179), SR2 (signal ratio of D3S1358/H o23), and RR (representation ratio of OCA2/D3S1358).

The threshold values for these parameters are provided in Table 6:

TABLE 6

|  | SR1 | SR2 | RR |
| --- | --- | --- | --- |
| Threshold for natural | >=0.9 | >=10 | >=2 |
| Threshold for artificial | <0.9 | <10 | <2 |

The observed values for these parameters, and the assigned category are provided in Table 7 (all values are above the threshold for natural DNA but only the RR category is above the threshold for artificial DNA).

TABLE 7

|  | SR1 | SR2 | RR | Category |
| --- | --- | --- | --- | --- |
| Natural DNA sample | 1.23 | 17.54 | 3.31 | Natural |
| Artificial DNA sample | 0.06 | 2.06 | 2.47 | Artificial |

Assignment of the category was performed according to the following rule:

If all observed parameter values are above their respective thresholds for natural DNA, then assign a "natural" category, otherwise assign an "artificial" category.

Example 6

Combined Profiling and Categorization of DNA (MDA Vs. Non-MDA)

This particular assay employs both conventional profiling of a DNA sample (with the Promega PowerPlex16 kit), and categorization of DNA into categories of MDA (artificial DNA that was synthesized by Multiple Displacement Amplification vs. other (non-MDA) types of DNA.

Two samples of DNA were analyzed—a natural DNA sample extracted from the blood of subject A, and an artificial DNA sample synthesized by in vitro multiple displacement amplification using a commercial kit (from a minute amount of subject A's real DNA as template).

The two samples were first profiled with a conventional kit (PowerPlex16) and analyzed using a conventional profiling software (GeneMapperID-X). The scheme of this procedure is as follows:

DNA→multiplex PCR using the PowerPlex16 primer mix→separation of amplification products on a capillary electrophoresis machine→analysis of data with the GeneMapperID-X software For each sample, the end product of this assay is a profile. The profiles of the two samples are identical, as can be seen in FIG. 15A-B. Furthermore, the GeneMapperID-X software determined the profiles of both samples to be single contributor (i.e. from a single person) profiles, with no anomalies.

Both samples of DNA were subsequently also analyzed by the Capillary Analyzer software. For each sample, the end product of this assay is a profile and assignment of category. As can be seen in FIG. 15C-D, the natural DNA was assigned as "non-MDA," in contrast to the MDA sample which was assigned as "MDA."

In this example, the assignment of category was performed by analysis of three parameters:

RR1 (representation ratio of vWA/D18S51), RR2 (representation ratio of CSF1PO/Penta_D), and RR3 (representation ratio of D21S11/D7S820).

A Combined Representation Score was calculated based on these three ratios as follows:

$$CRS = \sqrt[3]{R1 * R2 * R3}$$

The threshold value that was determined based on analysis of multiple MDA-samples and non-MDA-samples was 1.5, hence an unknown sample with a CRS value of above 1.5 is categorized as "MDA," while an unknown sample with a CRS value of below 1.5 is categorized as "non-MDA."

The CRS values of the MDA sample and non-MDA sample were calculated, and are as follows:

CRS value of MDA sample=2.04
CRS value of non-MDA sample=0.91

Based on the threshold value, both samples were correctly categorized.

Example 7

Stand Alone Semen Detector Kit

The assay employed by the kit accepts as input a DNA sample which then undergoes a biochemical procedure followed by signal analysis by a dedicated software. The output of the assay is the category of the DNA sample (semen or non-semen), and a statistical confidence level representing the likelihood that the outputted category is the true category of the DNA sample.

A semen detection kit of the present invention may comprise one or more of the following components:

1. A box that may comprise one or more of the following components:

Tube 1 comprising a 5× primer mix of:

```
                                              (SEQ ID NO. 55)
0.6 µM SD1f (AAGAGCCCATCAGGCAGGTC);

(SEQ ID NO. 56)
0.6 µM SD1r (GTTTCTTGTCGAGCAGCACGTGGATGATG);

(SEQ ID NO. 57)
1.75 µM SD2f (CTCCAGAACTGGAACTTCCTG);

(SEQ ID NO. 58)
1.75 µM SD2r (GTTTCTTAACTTGGAGACGACGGCATC);

(SEQ ID NO. 59)
1.25 µM SD3f (TGGAGGACAATGCCCTGGTG);

(SEQ ID NO. 60)
1.25 µM SD3r (GTTTCTTGGCTTCACCTGCGACCGTCTC);

(SEQ ID NO. 61)
1.75 µM SD4f (CCCTCCGAGTGGCCAGCAG);

(SEQ ID NO. 62)
1.75 µM SD4r (GTTTCTGACCACTGCCGTGGGAATG);

(SEQ ID NO. 63)
1.75 µM SD5f (CTTCTCAGCCAATGGGAAGAG);

(SEQ ID NO. 64)
1.75 µM SD5r (ACGTAGAAGGACCCGAGGAC);

(SEQ ID NO. 65)
0.9 µM SD6f (TACAGACAAATCACTCAGCAGC);
and
                                              (SEQ ID NO. 66)
0.9 µM SD6r (GTTTCTTGTCTGACACTCGGTTGTAGGTATT)
```

The forward primers (e.g., SD_f) are fluorescently labeled;

Tube 2 comprising a 10× reaction buffer (150 mM TRIS-HCl, 15 mM MgCl$_2$, 0.2 mM each dntp, 2.5 µg BSA);

Tube 3 comprising HhaI restriction endonuclease;

Tube 4 comprising a control semen DNA sampl;

Tube 5 comprising a control non-semen DNA sampl;

Tube 6 comprising a DNA ladder; and a Material Safety Data Sheet (MSDS).

2. A paper detailing the following protocol, or similar instructions:

(a) For each reaction, combine in a 0.2 ml tube (not provided) the following ingredients: 5 µl 5× primer mix, 2.5 µl 10× reaction mix, 0.5 µl HhaI endonuclease, 0.5 µl DNA polymerase, 0.5 ng DNA, and DDW (distilled water) to a total volume of 25 µl.

(b) In addition to the tested DNA, set up a positive control semen reaction using the supplied semen DNA, a positive control non-semen reaction using the supplied blood DNA, a negative control reaction using DDW instead of DNA, and a digestion control reaction using DDW instead of HhaI.

(c) Place the reaction tubes in the thermal cycler and run the following program: 37° C. for 15 min, 95° C. for 11 min, followed by 30 cycles of 94° C. for 1 min, 59° C. for 1 min, 72° C. for 1 min, followed by a final extension step of 60° C. for 45 min, and hold at 25° C.

(d) For each post-amplification reaction, mix 1.5 µl product with 24.5 µl formamide and 0.5 µl fluorescent size standard in a new 0.2 ml tube.

(e) Denature samples at 95° C. for 3 minutes, then immediately chill on ice for 3 minutes.

(f) Run denatured samples in the capillary electrophoresis machine using the following parameters:

Module=GS STR POP4 (1 mL) F;

Inj. secs=5;

Inj. kV=15;

Run kV=15;

Run C=60;

Run time=24 min (g) Analyze output .fsa files in the TissueIdentifier analysis software.

3. "TissueIdentifier" analysis software implementing the tissue identification algorithm as described in the "Algorithm and Software" section above, with the following modifications:

In step 3 of the algorithm, the set of pairs of loci used are: {SD1,SD6}, {SD2,SD6}, {SD3,SD6}, {SD4,SD6}, and {SD5,SD6}.

A correction for incomplete digestion was performed using the signal ratio of {SD5,SD6}. SD5 acted as a digested control locus and SD6 acted as an undigested control locus.

Reference probability functions of semen and non-semen were obtained for {SD1,SD6}, {SD2,SD6}, {SD3,SD6}, {SD4,SD6} using a set of 27 reference semen samples obtained from 27 different individuals and 86 reference non-semen samples (blood, saliva, urine, vaginal swab, menstrual blood) obtained from different individuals.

The assay is based on analysis of 6 genomic loci. Of these, 4 loci were found by the inventors to be differentially methylated in semen vs. non-semen tissues. Two of these four loci are methylated in all tissues except semen, and the two other loci are unmethylated in all tissues except semen. The assay also includes an undigested control locus that does not contain a HhaI recognition sequence (SD6) and is therefore expected to be amplified successfully regardless of the tissue type, and a digested control locus (SD5) which was found by the inventors to be unmethylated in all potential tissues.

Figure 12:
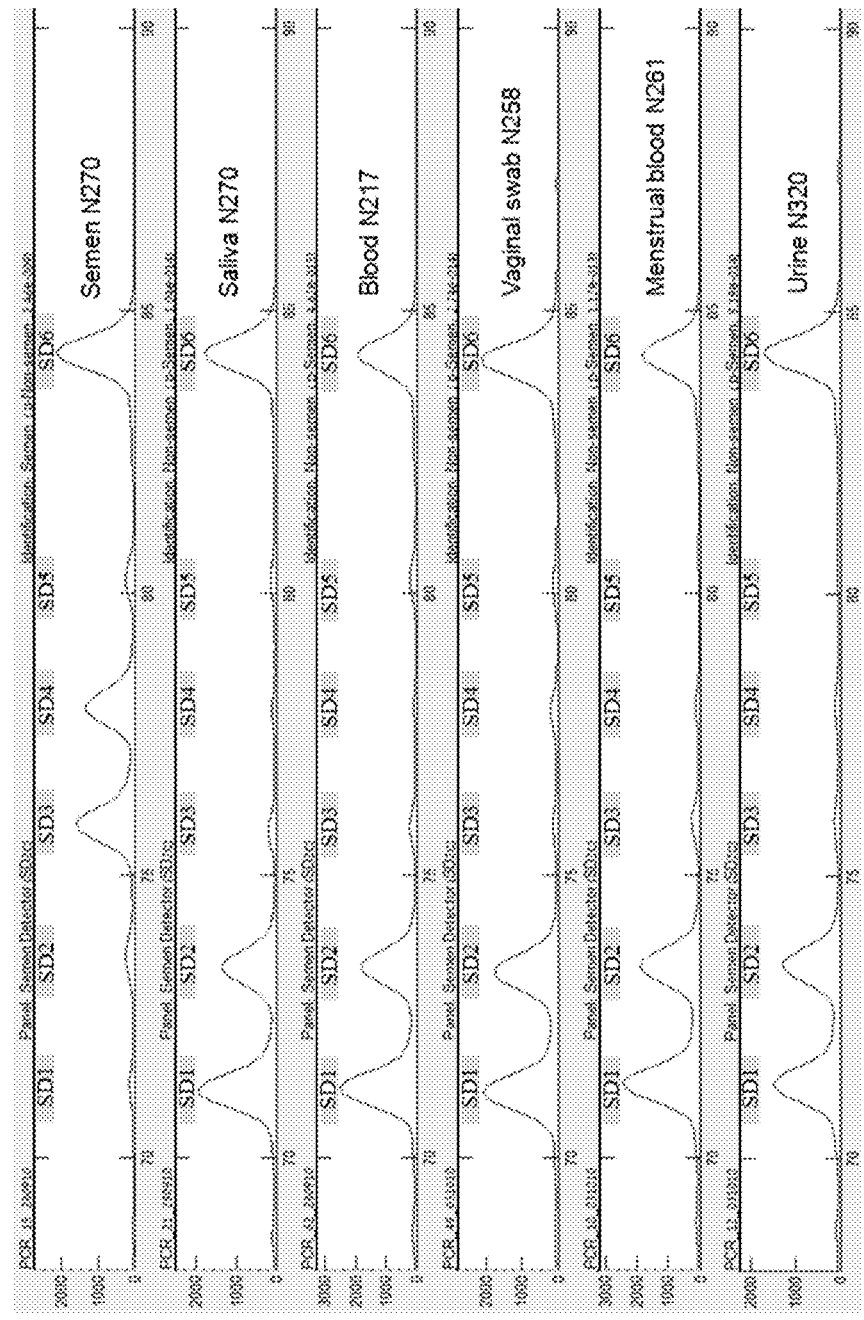
FIG. 12. Stand alone semen detection assay. Sample plots of 6 DNA samples from different tissue types are depicted. Correct categorization (semen vs. non-semen) was achieved for all samples. For each sample the confidence level of the least likely category is shown (e.g. for a "semen" categorization, the p value of non-semen is shown)
Figure 12:
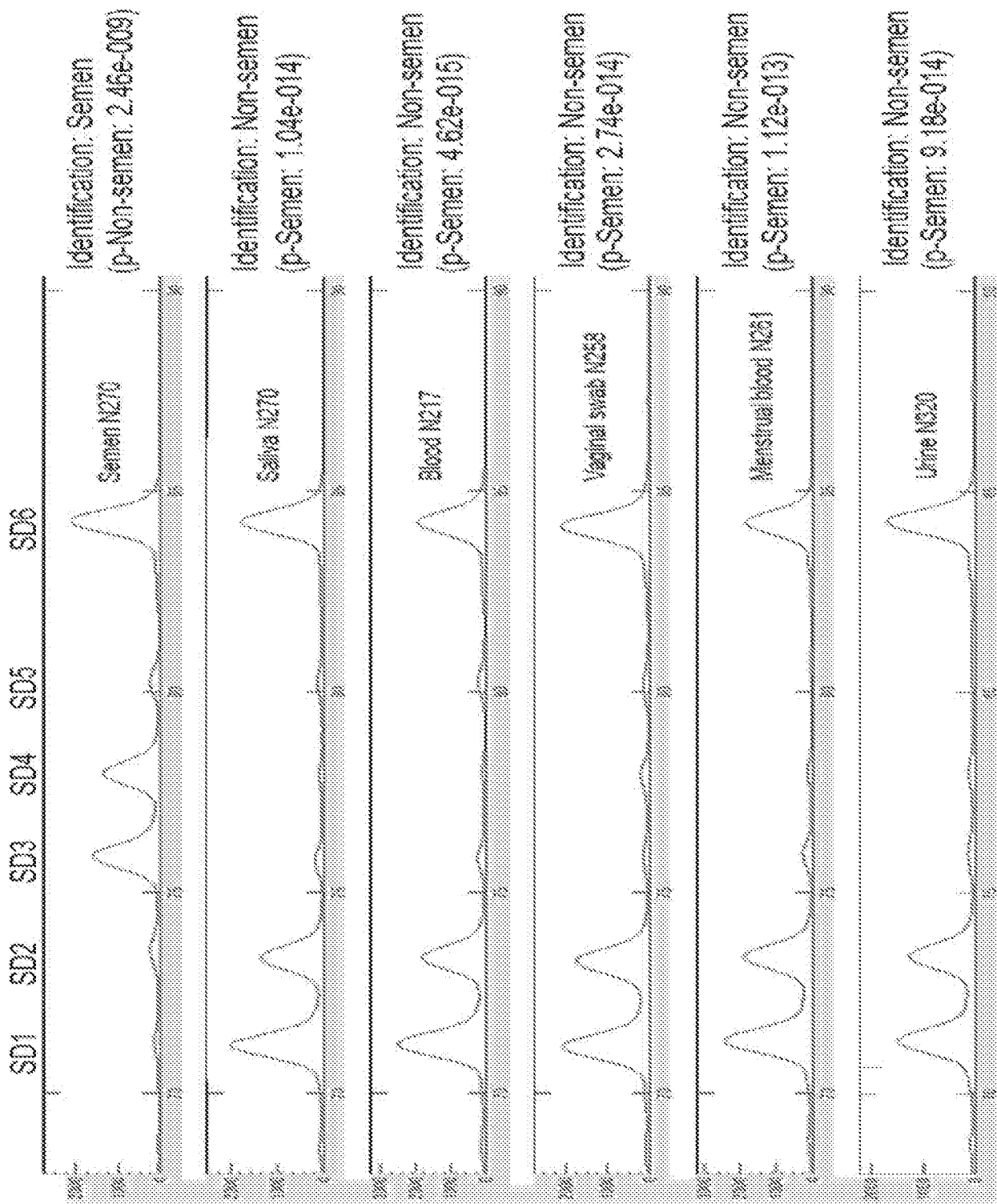

The kit was tested on 27 semen and 86 non-semen (blood, saliva, urine, vaginal swab, menstrual blood) DNA samples from 95 different donors of different sexes, ages, and ethnicities. The algorithm correctly identified the source of all samples with a typical confidence level>99.999999%. FIG. 12 shows sample plots of 6 samples. The tested samples were the same samples used for obtaining reference probability functions. However, in order to avoid bias, in each specific analysis, the analyzed sample was not used for obtaining the reference probability functions.

What is claimed is:

1. A method for categorizing a mammalian DNA sample as semen or non-semen, comprising:
   (A) applying the DNA mammalian sample to digestion with at least one methylation-sensitive restriction endonuclease or at least one methylation-dependent restriction endonuclease, to obtain restriction enzyme-treated DNA;
   (B) co-amplifying at least two different genomic loci from the same digest of restriction enzyme-treated DNA in a single reaction mixture using at least two different locus-specific primer pairs, wherein at least one of the loci is a restriction locus differentially methylated between semen and non-semen DNA, thereby generating a specific amplification product for each locus of said at least two different genomic loci, wherein said co-amplifying comprises using fluorescent PCR;
   (C) determining a signal intensity of each amplification product in said single reaction mixture;
   (D) calculating a signal ratio between the signal intensities of amplification products of the at least two different genomic loci determined in step (C) in said single reaction mixture;
   (E) providing a reference value representing a ratio between signal intensities of amplification products of said at least two different genomic loci in semen DNA;
   (F) comparing the signal ratio to the reference value; and
   (G) determining that the categorical source of the DNA sample is semen if the signal ratio matches the reference value,
   wherein the restriction endonuclease is Hhai and the at least two different genomic loci comprise L91762 (SEQ ID NO: 39) and L68346 (SEQ ID NO: 40), and wherein the step of amplifying is performed using the following primers:

1. L91762 (forward GCAGCAGGCCGCGGAGAAG (FAM) (SEQ ID NO: 67); reverse AGCAGCTGTGCCGGGCCAG (SEQ ID NO: 82));
and 2. L68346 (forward CAGCAACAGCACCCAGCTTG (JOE) (SEQ ID NO: 68); reverse CACAGGCTCAGTCGCGGATC (SEQ ID NO: 83)).

2. The method of claim 1, wherein a signal ratio of L91762/L68346 that is between 0.04 to 0.53 is indicative of semen.

3. The method of claim 1, wherein the at least two different genomic loci further comprise at least one of L50468 (SEQ ID NO: 41), L14432 (SEQ ID NO: 42), L30139 (SEQ ID NO: 45), L15952 (SEQ ID NO: 49), and L26688 (SEQ ID NO: 51).

4. The method of claim 3, wherein the step of amplifying is performed further using at least one of the following pairs of primers:

```
3. L50468 (forward AGGAAACCTCAGTAGCAAAATTG (JOE)
(SEQ ID NO: 69); reverse GCGAGACTTTAGGTGTGCATC
(SEQ ID NO: 84));

4. L14432 (forward CGTAGGCTGCGGTGAGCTC (FAM) (SEQ
ID NO: 70); reverse GATCCATGCCCGCTGGGATG (SEQ ID
NO: 85));

5. L30139 (forward GAGAAGCGGGAGGATGAGAC (FAM) (SEQ
ID NO: 73); reverse GACAGTATGCTGATGCTTCTTG (SEQ ID
NO: 92);

6. L15952 (forward CTCCCTGATTTACGACAAGTTC (FAM)
(SEQ ID NO: 77); reverse GACAGTATGCTGATGCTTCTTG
(SEQ ID NO: 92);
and 7. L26688 (forward CGGACCAGATTGCTGGTCAC (JOE) (SEQ
ID NO: 79); reverse CGACCTTGCCAGATGTTTGAC (SEQ ID
NO: 94).
```

5. The method of claim 1, wherein the at least two different genomic loci further comprise L76138 (SEQ ID NO: 48) and L26688 (SEQ ID NO: 51), and wherein a signal ratio of L76138/L26688 that is between 2.04-19.56 is indicative of semen.

6. The method of claim 1, wherein step (E) further comprises providing a plurality of reference values representing signal intensity ratios in mixtures of semen and non-semen at various proportions; step (F) further comprises comparing the signal ratio to the plurality of reference values; and step (G) comprises determining that the categorical source of the DNA sample is a mixture of semen and non-semen if the signal ratio matches one of said plurality of reference values.

7. The method of claim 1, wherein signal intensity is the amplification product's fluorescence level measured during capillary electrophoresis.

8. The method of claim 1, wherein step (B) is performed by real-time PCR.

9. The method of claim 1, further comprising simultaneously performing DNA profiling with the DNA categorization.

10. The method of claim 1, wherein the steps of digesting and co-amplifying the DNA sample are performed in a single tube.

11. The method of claim 1, wherein said single test tube comprises DNA template, digestion and amplification enzymes, buffer, primers designed to specifically amplify the at least two different genomic loci, and accessory ingredients.

12. The method of claim 1, wherein said single test tube is closed and placed in a thermal cycler, where the single reaction takes place.

13. The method of claim 1, wherein the at least two different genomic loci further comprise (1) a plurality of restriction loci and (2) a locus lacking a recognition sequence of the methylation-sensitive or methylation-dependent restriction endonuclease, and wherein step (D) comprises calculating a plurality of signal ratios, between the signal intensity of the amplification product of the locus lacking said recognition sequence and the signal intensities of each restriction locus, and wherein step (F) is repeated for each of said plurality of signal ratios.

14. The method of claim 13, wherein step (D) further comprises calculating signal ratios between the signal intensity of the amplification product of each one of said plurality of restriction loci and the signal intensity of the amplification product of each of the remaining of said plurality of restriction loci.

15. The method of claim 13, wherein step (D) comprises calculating a plurality of signal ratios, between the signal intensity of the amplification product of each one of said plurality of restriction loci and the signal intensity of the amplification product of each of the remaining of said plurality of restriction loci.

16. The method of claim 1, wherein no standard curve from control DNA is generated and wherein no actual methylation level at any genomic locus is indicated by said method.

17. The method of claim 1, wherein the DNA mammalian sample is a human DNA sample.

* * * * *

UNITED STATES PATENT AND TRADEMARK OFFICE
CERTIFICATE OF CORRECTION

PATENT NO. : 9,752,187 B2
APPLICATION NO. : 13/492187
DATED : September 5, 2017
INVENTOR(S) : Wasserstrom et al.

Page 1 of 2

It is certified that error appears in the above-identified patent and that said Letters Patent is hereby corrected as shown below:

In the Drawings

Replace Figure 12 with the attached.

In the Specification

Column 26:
Line 7, after "example MetDB", delete "(http://www.methdb.net)".

Signed and Sealed this
Thirty-first Day of October, 2017

Joseph Matal
*Performing the Functions and Duties of the
Under Secretary of Commerce for Intellectual Property and
Director of the United States Patent and Trademark Office*

SEQUENCE LISTING

<160> NUMBER OF SEQ ID NOS: 104

<210> SEQ ID NO 1
<211> LENGTH: 889

<212> TYPE: DNA
<213> ORGANISM: Homo sapiens

<400> SEQUENCE: 1

```
ctcttctcat tccacaagct ctccccaaaa gaccccattc ctccccacct tcaaccatct      60
ctggcaggga ggaggggaa ctgagaggct actttctgac ccaggaccct aagcctgtgt     120
acggagagag catgagctgg gtgagctgct tgccaaggag tggcatctgc cctcatcagt     180
ggacacaaaa agccccaggg gttaagtggc catggctgcc ctcatggctg caccgggagg     240
atgactgtgt tcccactctc agtcctgccg aggtgcctga cagccctgca cccaggagct     300
gggggggtcta agagcttgta aaaagtgtac aagtgccaga tgctcgttgt gcacaaatct     360
aaatgcagaa aagcactgaa agaagaatcc agaaaccac agttcccatt tttatatggg     420
agcaaacaaa ggcagatccc aagctcttcc tcttccctag atcaatacag acagacagac     480
aggtggatag atagatagat agatagatag atagatagat agatagatat cattgaaaga     540
caaacagag atggatgata gatacatgct tacagatgca cacacaaacg ctaaatggta     600
taaaaatgga atcactctgt aggctgtttt accacctact ttactaaatt aatgagttat     660
tgagtataat ttaattttat atactaattt gaaactgtgt cattaggttt ttaagtctat     720
ggcatcactt tcgcttgtat ttttctattg atttcttttc ttttcttttc ttttttgaga     780
cagagtctca ctctcaccca ggctggagta ccgtggcacg atcttggctc attgcaacca     840
ccacctcccg ggctcaagtg attatcctgc ctcagcctcc caaatagct                889
```

<210> SEQ ID NO 2
<211> LENGTH: 843
<212> TYPE: DNA
<213> ORGANISM: Homo sapiens

<400> SEQUENCE: 2

```
atatgctaac tggatgtgaa caattgtgtt ctaatgagct taatatgagt ttcataatttt      60
gtgcattttg ctgttaaaaa gccagaaaac aaaacaaaac aaaatactga aaccagtgtg     120
aacaagagtt acacgatgga aggcatcagt tttcacacca gaaggaataa aaacaggcaa     180
aaataccata agttgatcct caaaatatga ttgattttaa gccttatgag ataattgtga     240
ggtcttaaaa tctgaggtat caaaaactca gagggaatat atattcttaa gaattataac     300
gattccacat ttatcctcat tgacagaatt gcaccaaata ttggtaatta aatgtttact     360
atagactatt tagtgagatt aaaaaaaact atcaatctgt ctatctatct atctatctat     420
ctatctatct atctatctat ctatctatct atcgttagtt cgttctaaac tatgacaagt     480
gttctatcat acccttttata tatattaacc ttaaaataac tccatagtca gcctgaccaa     540
catggtgaaa cccgtctctct aaaaaaaata caaaaattag ctggatgcag tagcacatgc     600
ctgtagtccc agctactcag gaggctgggg caggagaacc acttgaccca agaagcggag     660
gttgcagtga gccgagatcg caccactgca ctccagcctg ggtgacagag tgagactcca     720
tctcaagata aagaaataaa taaaaacaaa caaacaaaaa aattccatag ggggtcaggt     780
gcggtggctc atgcctgtaa tcccagcact ttgggaggcc gaagcaggtg gatcacttga     840
ggt                                                                    843
```

<210> SEQ ID NO 3
<211> LENGTH: 792
<212> TYPE: DNA
<213> ORGANISM: Homo sapiens

<400> SEQUENCE: 3

```
aatatgaatt caatgtatac agagagagag agagagagag agagagagag agacttctac      60
agagctctaa gcataattgt gtaactccaa gctcacagtg cctaagacca gtaccaggct     120
gactcattgg aaagctgcca tagtaagact cttctgttca ctgcattatt tattgatgta     180
ttgcaagcac ttagttacat ttctagcata taacacatga tcaataaata ttttgacatg     240
aacaaatggt aattctgcct acagccaatg tgaatattgg gatgggttgc tggacatggt     300
atcacagaag tctgggatgt ggaggagagt tcatttcttt agtgggcatc cgtgactctc     360
tggactctga cccatctaac gcctatctgt atttacaaat acattatcta tctatctatc     420
tatctatcta tctatctatc tatctatcaa tcaatcatct atctatcttt ctgtctgtct     480
ttttgggctg cctatggctc aacccaagtt gaaggaggag atttgaccaa caattcaagc     540
tctctgaata tgttttgaaa ataatgtata ttaatgaatg tacaaatttc cccacttgta     600
ctttcagact gttatctgtg agttaaaact cctccactct ttttcctacc caaataatag     660
catactttt tctgagtata ttttgggaag aagagttatt cagttattgt tatattttaa      720
aaaattcctt ataccaaact ctacttgatc taaggctatt cattgaaact ttcagcatgc     780
ttaatagcag tc                                                         792
```

<210> SEQ ID NO 4
<211> LENGTH: 735
<212> TYPE: DNA
<213> ORGANISM: Homo sapiens

<400> SEQUENCE: 4

```
ccctctgtgt agcctggcta tgtgccacat tgtgaggttc tctccctcta gctacttctt      60
ccagtttcct ctttcaggat cccaattcct ttctcaaagc actggtgaat aactccaaat     120
actccatcat ttcattatac agagtaatat aagtcttctt tttctaaacc tctcccatct     180
ggatagtgga cctcatattt cagatgctaa taggctgttg aggtagtttc ctaagcaaaa     240
aagtaattgt ctctctcaga ggaatgcttt agtgcttttt agccaagtga ttccaatcat     300
agccacagtt tacaacattt gtatctttat ctgtatcctt atttatacct ctatctatct     360
atctatctat ctatctatct atctatctat ctatcttcaa aatattacat aaggatacca     420
aagaggaaaa tcacccttgt cacatacttg ctattaaaat atactttat tagtacagat      480
tatctgggac accactttaa ttagaagctt taaaagcata tgcatgtctc agtatttaat     540
tttaaaatta ttcataatt atatactcct ttgaattaga aaattacaaa tgtggctatg      600
tattattttc tcccatgtat tttcaaaatg aggggtaag ccagaccctc tccctctccc      660
atgcctaata gctcaaagtt aaaggtaaag aaacaagaaa atatggtgaa agttaaccag     720
cttcacttca gagga                                                      735
```

<210> SEQ ID NO 5
<211> LENGTH: 949
<212> TYPE: DNA
<213> ORGANISM: Homo sapiens

<400> SEQUENCE: 5

```
attcaacaca tgaggcacgg ccagacctaa atgtctcaga gcctgctccc actccgatga      60
gctgctgcct tgcttcaggg tctgagtcca gtgactgcca ctgcctgcac ccaatcacca     120
tagccagaga cctggaggtc atccttatct cctttctctt cctcatccct gcatctcaga     180
ctcttccaca caccactggc catcttcagc ccattctcca gcctccaggt tcccacccaa     240
```

```
cccacatggt gccagactga gccttctcag atactatctc ctggtgcaca cttggacagc    300
atttcctgtg tcagaccctg ttctaagtac ttcctatctc tctatctatc tatctatcta    360
tctatctatc tatctatcta tatctctaat ctatctatct tctatctatg aaggcagtta    420
ctgttaatat cttcatttta caggtaggaa aactgagaca caggggtggtt agcaacctgc    480 tagtccttgg cagactcagg ttggaacact gccctggagt gtgtgctcct gaccaccacg    540
aagtgcctcc tctgtacaat ctgaccccat cactctcctc tttacaatga cctcccaata    600
ggttaagatg cagttattct ttctcacttt aagacacctt tacctccggc ttctgccacc    660
tcctctgctc cctgtggcc actcctcaca ccactccaca tcccagctgt tgtcaagttc     720
tttcagtgtt ccaaatgatc tatgttctct ttgcctttga gccttgcata tgttcctccc    780
tctgccagaa gcgctgttcc ccttcctttc ccacccttct gcccggccaa ctcaccttca    840
ttcttcccat cccagtttag aggccacctt ctcgaagcct gggttggggg gactcttcag    900
tgttcccagg acaccttgtg cttcccccat aatcactggg tgatcattg                949

<210> SEQ ID NO 6
<211> LENGTH: 832
<212> TYPE: DNA
<213> ORGANISM: Homo sapiens

<400> SEQUENCE: 6
cccagcacac accttgcctc tggctgggac cccctttgct gctggccctg ctcaggcccc     60
acagcttgat ctcctcatgt tcccactgct gacttcccca agctaactgt gccacagagt    120
gggggacccc ctcccggctc tcacaacccc caccttcctc tgcttcactt ttcaccaact    180
gaaatatggc caaaggcaaa aacccatgtt cccactggcc tgtgggtccc ccatagatc     240 gtaagcccag gaggaagggc tgtgtttcag ggctgtgatc actagcaccc agaaccgtcg    300
actggcacag aacaggcact tagggaaccc tcactgaatg aatgaatgaa tgaatgaatg    360
aatgaatgtt tgggcaaata aacgctgaca aggacagaag ggcctagcgg aagggaaca    420 ggagtaagac cagcgcacag cccgacttgt gttcagaaga cctgggattg gacctgagga    480
gttcaatttt ggatgaatct cttaattaac ctgtggggtt cccagttcct ccctgagcg     540 cccaggacag tagagtcaac ctcacgtttg agcgttgggg acgcaaacac gagagtgctt    600
ggtgtgagca cacaggagga gtcacgacag agcagtgtaa gagccgccac gtgggtccca    660
cacaggggga gtcacgacac agcagtgtaa gagccgccac gagggtccca cacagggga     720 gtcgcgacac agcagtgtaa gagccgccac gagggtccca cacaggggga gtcacgacac    780
agcagtgtaa gagccgccac gagggtccca cacaggggga gtcacgacac ag            832

<210> SEQ ID NO 7
<211> LENGTH: 766
<212> TYPE: DNA
<213> ORGANISM: Homo sapiens

<400> SEQUENCE: 7
ttacccttgg ggtgggggtg taggatgcag ctggggctgc agttccaggc cacggagagc     60
ctgtgaggct gggccccggg gcgccctggg gaggggatgc ctgatgggga gcctggtggg    120
ggagggtagg ggagggcggg ggaggacggg ggagggcgcc ctgtgtccct gagaaggtac    180
ctggaaatga cactgctaca actcacacca catttcaatc aaggtccata aataaaaacc    240
cattttaaat gtgccaggga gcccaaggtt ctgagtgccc aaggaggcac cgaagacccc    300
```

| | |
|---|---|
| tcctgtgggc tgaaaagctc ccgattatcc agcctggccc acacagtccc ctgtacacag | 360 |
| ggcttccgag tgcaggtcac agggaacaca gactccatgg tgaatgaatg aatgaatgaa | 420 |
| tgaatgaatg agggaaataa gggaggaaca ggccaatggg aatcacccca gagcccagat | 480 |
| acccttttgaa ttttgccccc tatttgccca ggaccccca ccatgagctg ctgctagagc | 540 |
| ctgggaaggg ccttggggct gcctccccaa gcaggcaggc tggttggggt gctgactagg | 600 |
| gcagctgggg cagagggagg caggggcagg tgggagtagg gtgggggctg ggtgcagcag | 660 |
| ccggggaccct ctggccatct tggattttttt ggatggattt gtttccacat tccgatcgtt | 720 |
| aagattcaag atgaaacaag acacagagac ccacacgacc cccgag | 766 |

<210> SEQ ID NO 8
<211> LENGTH: 751
<212> TYPE: DNA
<213> ORGANISM: Homo sapiens

<400> SEQUENCE: 8

| | |
|---|---|
| agatgataga tacatatgtt agacagagat aggatagatg atagatacat aggttagata | 60 |
| gagataggat agattataaa tagatacaca ggttagatag attagacaga cagatagata | 120 |
| catacataga tataggatag ataactagat acaatagaga tagatagata gatagataga | 180 |
| tgatagagga tagatgataa atagatatat agcttagata gagataggat agatgataga | 240 |
| tacataggat agatagagac aggatagatg ataaatagat acataggtta gatagagata | 300 |
| ggacagatga taaatacata ggatggatgg atagatggat agatagatag atagatagat | 360 |
| agatagatag atagatagat agacagacag acagacagac agatagatca atccaagtca | 420 |
| catactgatt attcttatca tccactaggg ctttcacatc tcagccaagt caacttggat | 480 |
| cctctagacc tgtttcttct tctggaaggt gggaactcta ccttatagga tcagtctgag | 540 |
| gagttcacaa ataataagg gcaaagtgcc cggcacattg taggagacta gtaatgtcta | 600 |
| taaaatgagg ggcttgaagt aaatgatccc tctagttctc tctactgcta acattctaag | 660 |
| acctccttta cattaattgt tctcaagcca catctccctc ccctacagga cttctattta | 720 |
| tttctgatca atttcatgag tacaaataag t | 751 |

<210> SEQ ID NO 9
<211> LENGTH: 945
<212> TYPE: DNA
<213> ORGANISM: Homo sapiens

<400> SEQUENCE: 9

| | |
|---|---|
| actgaacatt tgcttttgaa atttactatc tatgtaccgt tggaaaattt acttaatatc | 60 |
| tctgaatttt ttttcttcaa ctgtggagtg aggaaaataa tacctacttt taggtagatg | 120 |
| atggatataa cacttttctc tgcatatagt agacactcag tgcataacta tcgccttcct | 180 |
| tttccctcta ctcagaaaca aggacatctg ggaccacagc cacatactta cctccagtcg | 240 |
| tttcatatca accaactgag ctctaacatt tttctgcaga agctggatat gctgtacttt | 300 |
| ttctatgact ttgcgcttca ggacttcaat tctgcttctc agatcctctg cactcggtt | 360 |
| gtaggtatta tcacggtctg aaatcgaaaa tatggttatt gaagtagctg ctgagtgatt | 420 |
| tgtctgtaat tgccagcaaa aagaaagga agaaggaag gaaggagaaa gaaagaaaga | 480 |
| aagaaagaaa gaaagaaaga aagaaagaaa gaaagaaaga aagagaaaaa agaaagaaag | 540 |
| aaactagctt gtaaatatgc ctaatttttat tttggttaca gtttaatctg tgagttcaaa | 600 |
| acctatgggg catttgactt ttggataatg ttatgccctg cagccttcca tgaatgccag | 660 |

```
ttaagatgtc ctaatagcaa ttagtaatcc caaagaaata tagaagaaga actttctttg      720
gaattttaaa ggtgtaattt ggagttaaaa tagttggttt gattgcattt caattatttt      780
ataacatcct taatcaaggg acttgaacat attggatttt cttactgatg agcttttctt      840
tttaatctat agatttgaaa tggttcctaa gctgttttgg gtcaacagga tcactcactt      900
gccagctagt gttgcatcac tgattttaaa tgtcaagtgt ttgtg                      945
```

<210> SEQ ID NO 10
<211> LENGTH: 823
<212> TYPE: DNA
<213> ORGANISM: Homo sapiens

<400> SEQUENCE: 10

```
gttggctggg gctcagagag aacaaaaagg cagaggaaaa acaaatttcc cctctcactt       60
ctggagatgg aacactttc ttctgctttt ggacatcaga aatccaagtt ctctggcctt      120
tggactttgg gacttgtgcc agcaccctcc tgggttccct ggcctttggc ctcaaactga      180
aggttacact atcagcttcc gttgttctaa gggcttcaga cttggacagc cacactgcca      240
gcttccctga ttcttcagct tgtagatggt ctgttatggg acttttctca gtctccataa      300
atatgtgagt caattcccca agtgaattgc cttctatcta tctatctatc tgtctgtctg      360
tctgtctgtc tgtctatcta tctatatcta tctatctatc atctatctat ccatatctat      420
ctatctatct atctatctat ctatctatct atctatctat cgtctatcta tccagtctat      480
ctacctccta ttagtctgtc tctggagaac attgactaat acaacatctt taatatatca      540
cagtttaatt tcaagttata tcataccact tcatacatta tataaaacct tacagtgttt      600
ctcccttctc agtgtttatg gctagtaatt ttttactggg tgccagacac taatttttat      660
tttgctaagt ggtgaatatt ttttatatcc ttaaaaatat ttttgagtgt tgatctgggt      720
aaagttaagt tcaatattgg aaaaatattg attcttttga ggatagttat cttctaatta      780
gtctacctgt tgccccataa atggcatgat tttccactct gtg                       823
```

<210> SEQ ID NO 11
<211> LENGTH: 824
<212> TYPE: DNA
<213> ORGANISM: Homo sapiens

<400> SEQUENCE: 11

```
tactacagca agagcgcttg aaccagatgt aggggagata gcagctggag agcataacag       60
aggcactgac atgtgagcag ctaacgaggc cttttacaag acatctgtga ccacacggcc      120
aagtagaaga aagccgttaa aagcatcaag gtagttaggt aaagctgagt ctgaagtaag      180
taaaacattg ttacaggatc cttggggtgt cgcttttctg gccagaaacc tctgtagcca      240
gtggcgcctt tgcctgagtt ttgctcaggc ccactgggct ctttctgccc acacggcctg      300
gcaacttata tgtatttttg tatttcatgt gtacattcgt atctatctgt ctatctatct      360
atctatctat ctatctatct atctatctat ctattcccca cagtgaaaat aatctacagg      420
ataggtaaat aaattaaggc atattcacgc aatgggatac gatacagtga tgaaaatgaa      480
ctaattatag ctacgtgaaa ctatactcat gaacacaatt tggtaaaaga aactggaaac      540
aagaatacat acggttttg acagctgtac tattttacat tcccaacaac aatgcacagg      600
gtttcagttt ctccacatcc ttgtcaacat ttgttatttt ctgggttttt gataatagct      660
gtgaaaggaa aataaaaact tgggccgggc gcggtggctc acgcctgtaa tcccagcact      720
```

```
ttgggaggcc aaggcgggca gatctcaagg tcgggagatt gagaccatcc tggctaacat    780
ggtgaaaacc catctctact aaaaatacaa aaacaaaaaa ttag                     824
```

<210> SEQ ID NO 12
<211> LENGTH: 927
<212> TYPE: DNA
<213> ORGANISM: Homo sapiens

<400> SEQUENCE: 12

```
catgccacta agctgtacac tgaaaaacgg ttaacatgat aaattttatg ttacatacat     60
tttaccacaa tttaaaaaaa ttattaaaaa atactaacaa taggccaagc gtgatggctc    120
acacctgtaa tcccagcact tgggaggct gagacaggtg gatcaattga gctcaggagt    180
ttgagaccag cctgggtaac acagtgagac ccctgtctct acaaaaaaat acaaaaatta    240
gttgggcatg gtggcacgtg cctgtagtct cagctacttg cagggctgag gcaggaggag    300
ttcttgagcc cagaaggtta aggctgcagt gagccatgtt catgccactg cacttcactc    360
tgagtgacaa attgagacct tgtctcagaa agaaagaaag aaagaaagaa agaaagaaag    420
aaagaaagaa agaaagaaag aaagaaagaa agaaagaaaa agagagagga aagaaagaga    480
aaaagaaaag aaatagtagc aactgttatt gtaagacatc tccacacacc agagaagtta    540
atttaatttt taacatgtta agaacagaga gaagccaaca tgtccacctt aggctgacgg    600
tttgtttatt tgtgttgttg ctggtagtcg ggtttgttat ttttaaagta gcttatccaa    660
tacttcatta acaatttcag taagttattt catctttcaa cataaatacg cacaaggatt    720
tcttctggtc aagaccaaac taatattagt ccatagtagg agctaatact atcacattta    780
ctaagtattc tatttgcaat ttgactgtag cccatagcct tttgtcggct aaagtgagct    840
taatgctgat caggtaaatt aaaaattata gttaattaaa agggcataaa tgttacctga    900
ctcaataagt catttcaatt aggtctg                                        927
```

<210> SEQ ID NO 13
<211> LENGTH: 731
<212> TYPE: DNA
<213> ORGANISM: Homo sapiens

<400> SEQUENCE: 13

```
ctggttttgg tggaattgac tccctctgtc acaaactcag cttcagccca taccctgagc     60
catagaccta tccctctaat gcattgtact agtctcaggg ctaataacaa gggagaggtg    120
tcaaagggcc agttccacct ccaccaccag tggaaaagct attcccaggt gaggactgca    180
gctgccaggg cactgctcca gaatgggcat gctggccata ttcacttgcc cacttctgcc    240
cagggatcta ttttttctgtg gtgtgtattc cctgtgcctt tgggggcatc tcttatactc    300
atgaaatcaa cagaggcttg catgtatcta tctgtctatc tatctatcta tctatctatc    360
tatctatcta tctatctatc tatctatcta tgagacaggg tcttgctctg tcacccagat    420
tggactgcag tggggaatc atagctcact acagcctcaa actcctgggc tcaagcagtc    480
ctcctgcctc agcctcccaa gtacctggga ttataggcat gagccaccat gtccggctaa    540
tttttttttt taagagatgg ggtctcgctg tgttccccag cctgtctta aactcctggc    600 ctcaagtgat cctcccatct cagccttcca aagtgctgag attacagcag aggcttttaa    660
gtcaaagctt tccctgctag gacaagccct agttaaagtc ctggagcact ggccactgca    720
gctgcacttg g                                                         731
```

<210> SEQ ID NO 14
<211> LENGTH: 1026
<212> TYPE: DNA
<213> ORGANISM: Homo sapiens

<400> SEQUENCE: 14

```
cctactcggg aggctgaggc aggagaatcg cttgaaccca ggaggggcg actgcagtga        60
gccgagatcg tgccactgca ctccagcctg ggtgacagag cgagactcca tctcaaaaaa       120
aaaaaaaaaa aaacagaatc ataggccagg cacagtggct aattgtacct tgggaggctg       180
agacgggagg atcgagacca tcctgggcac catagtgaga ccccatctct acaaaaaaaa       240
aaaaaaattt tttttaaata gccaggcatg gtgaggctga agtaggatca cttgagcctg       300
gaaggtcgaa gctgaagtga gccatgatca caccactaca ctccagccta ggtgacagag       360
caagacacca tctcaagaaa gaaaaaaaag aagaaaaga aagaaaaga aagaaaaga           420
aagaaaaga aagaaaaga aagaaaaga aagaaaaaa cgaaggggaa aaaaagagaa           480
tcataaacat aaatgtaaaa tttctcaaaa aaatcgttat gaccataggt taggcaaata       540
tttcttagat atcacaaaat catgacctat taaaaaataa taataaagta agtttcatca       600
aaacttaaaa gttctactct tcaaaagata ccttataaag aaagtaaaaa gacacgccac       660
aggctaagag aaagtacttc taatcacata tctaaaaaag gacttgtgtc cagattaaag       720
aattcttaca catcaataag acaacccaat taaaaatggg caaagatttt gaagagatat       780
ttaaccaaag aaaacatata aatgtgtccg ggcgcgatgg taatcccagc actttgagag       840
gccgaggcag gcggatcact tgaggtcagg agtttaggac cagtctggcc aacatggtga       900
aaccctgtct ctaataaaaa tacaaaaatt agctgggtgt ggtggcgtaa gcctgtaatc       960
ccagctgctc aggaggctga ggcagaagaa ttgcttgaac ctgggaggtg gaggctgcag      1020
taagcg                                                                1026
```

<210> SEQ ID NO 15
<211> LENGTH: 977
<212> TYPE: DNA
<213> ORGANISM: Homo sapiens

<400> SEQUENCE: 15

```
cacatgtgga catttcttat tttctcatat tggtggtatg gctcatttat gaagttaata        60
ctggacattg tggggaggct gtgtaagaag tgttaaaggg gatcagggat acattcactt       120
ctcttttcct tgctagttc tgtggtctta agcaaagtag cctcaaacat cagtttcctc        180
ttttataaaa tgaggaaaat aatactcatt accttgcatg catgatataa tgattacata       240
acatacatgt gtgtaaagtg cttagtatca tgattgatac atggaaagaa ttctcttatt       300
tgggttatta attgagaaaa ctccttacaa ttttcttttc ttttcttttc ttttctttga       360
gactgagtct tgctcagtcg cccaggctgg agtgcaatgg cgtgatctcg gctcacttca       420
atctccacct cctgggttca agtgattctc ctgtttcagc ctccagagta gctgggatta       480
caggtgccta ccaccacacc cagctaattt tttgtatttt agtagagacg gggtttcacc       540
atgttgccca ggctggtctt gatctcctga gctcaggtaa tacacctgca tcggcctccc       600
aaagtgctag gattgcaggc gtgaatcacc gcacctgtcc acaattttct tgttattggt       660
acccttcat gttggtaaaa tgtatttttat tttctcttat caaataattt tcaatgcaat       720
gagacgtcaa cttaagccc aaagtagacc agtagtaaaa ctaaggctga aaccattgat       780
tgattattac catatattgt cctaaaatat tcggctttta aaacatttgg tttcatttt        840
```

```
catgataaaa atatgtagca tttttgcact tttaattcac tttgtagagt tctcaatcat      900
ttctaacaca tgcttggcaa tgacaagcca tttgtgaaag agttttgctg gctttaaaat      960
atatgcaaat gtaatat                                                    977
```

```
<210> SEQ ID NO 16
<211> LENGTH: 706
<212> TYPE: DNA
<213> ORGANISM: Homo sapiens

<400> SEQUENCE: 16
aggtctcctc ttctatacag cacatttgtt caaactaaaa acagacctca agtatattct       60
gcactatata gattttttta aagtagcttc agtctccttt aatgtgaaca attgcatact      120
gacttaatct cttcctctct cttctcttcc ttcactctct cccttcctct ctctttctat      180
tctcctcccc tcctccctgt aaaagctacc acctcatcct gggcaccctg gttatatcaa      240
cttcagctat gaggtaattt ttctctttac taattttgac cattgtttgc gttaacaatg      300
ccctgggctc tgtaaagaat agtgtgttga ttctttatcc cagatgtttc tcaagtggtc      360
ctgattttac agttcctacc accagcttcc cagtttaagc tctgatggtt ggcctcaagc      420
ctgtgtcgtc ccagcagcct cccgcctggc cactctgact cagtctgtcc tcctaaatat      480
ggccgtaagc ttacccatca tgaaccacta ctcagggagg ctccatgata gggcaaaaag      540
taaactctga ccagcttggt tctaacccag ctagtaaaat gtaaggatta ggtaagatgt      600
tatttaaaac tctttccagc tcaaaaaact cctgattcta agatagtcac actctatgtg      660
tgtctcttgc ttgcctctgc tgaaatatta gtgactaagt ggtata                    706
```

```
<210> SEQ ID NO 17
<211> LENGTH: 712
<212> TYPE: DNA
<213> ORGANISM: Homo sapiens

<400> SEQUENCE: 17
ttattctcca atattttgaa atgtgaatat tacagtaatt tcccttgtcc aaatgagaaa       60
accagggttc caaagagagg aaattatttg cccaaagtta gtaattttac ctaatcttta      120
cattttaccg gatgggatag aaccaagctg gtcagtcaga gttgacttt tgcccttca      180 tggaaccttc ctgagcagtg gttcatgaat gaataaactt acagccatat ttaggaggaa      240
agagtcaatc cgaatggtca ggcaggaggg tgctggagca acacaggctt gaggccaacc      300
atcagagctt aaactgggaa gctgatggta ggaactgtaa aattgggacc acttgagaaa      360
ccactttatt tgggatgaag aatccaccca ctattcttta cagagcccag gggactgcta      420
atgcaaacag tgatcaaaat tagtaaagag aaaaattacc tcatagctga agttgatata      480
accagggtgc ccaggatgag gtggtagctt ttatagggag gaggggagga gaagagaaag      540
agagaggaag ggagagtgtg aaggaaggga agagagagta agagattaag tcaatatgca      600
attgttaaca ttaagagaga ctaaaattac ttttaaaaaa tctatatagt acagaatata      660
tttgaggtct gttttcgtt aaaacaagtg tgctatgtag gagaggagac tt              712
```

```
<210> SEQ ID NO 18
<211> LENGTH: 840
<212> TYPE: DNA
<213> ORGANISM: Homo sapiens

<400> SEQUENCE: 18
acaaggcacg gaactcacac ccagcctctc tccatacaac agaatatggg ttcttgcgga       60
```

```
gctggactct gcaggagtct atctaatatg gactctgtgt caatgactcc tgggcctcct    120
ctgatcaccc cattaaagtc cttcgattgc tttgagcctc aaatctatgt gacatcaata    180
cgttcatttc ttcctagcac ttagaactgt ttcttgttga tacatttgct ggcttcttcc    240
ctgtctcacc ccttttccta ccagaatgcc agtcccagag gcccttgtca gtgttcatgc    300
ctacatccct agtacctagc atggtacctg caggtggccc ataatcatga gttattcagt    360
aagttaaagg attgcaggag ggaaggaagg acggaaggaa ggaaggaagg aaggaaggaa    420
ggaaggaagg aaggaaggaa ggaaggcagg caggcaggca ggcaggcagg caaggccaag    480
ccatttctgt ttccaaatcc actggctccc tcccacagct ggattatggg ccagtaggaa    540
ttgccatttt cagggttttg ctgtcactgt agtcaggacc atgaagtctt taggcacctc    600
cactccacac accccctggt gagagctccc atctccctgt tctgaaacag ctccccaata    660
tagtactgat tccggttaaa cttgaacccc tgcccctgcc cctgcccctg atttacatga    720
ggacactgag gccagagggg gtaaagtgac tgccagggga cacacagcta gaaagtggcg    780
gtgccagaac tggaaggagg ccctcattcc tgagtcacgg cttttccata gcacagcctt    840
```

<210> SEQ ID NO 19
<211> LENGTH: 780
<212> TYPE: DNA
<213> ORGANISM: Homo sapiens

<400> SEQUENCE: 19

```
atgaaactgg acacagaaac cagacccag agcacatacc gtatgagtcc attggtatga     60
agtttaaaaa cagatggcac tagtccaaag gattggaagt tggaatagtg gttaccagga    120 ctgggggggag gaagggatgg tggatggtga acaaaaggac cttggagggc tcctgggggtt  180 ctaggaatca atcttccttc tttccttcct tccttccttc ctctttctct ctttctttct    240 gttttttattt caataggttt ttaaggaaca ggtggtgttg gttacatgaa taagttcttt    300
agcagtgatt tctgatattt tggtgcaccc attacccgaa taaaaatctt ctctctttct    360
tcctctctcc ttccttcctt ccttccttcc ttccttcctt ccttcttcc ttccttccta    420 ccttctttcc ttcaacagaa tcttattctg ttgcccaggc tggagtgcag tggtacaatt    480
atagcttttt gcagcctcaa cctcctgggc tcaagtgatc ttcctgcccc agcctcctga    540
gtagccagga ctacaggaat gtgccaacat gcctggctaa ttttaaaaaa ttttttatag    600
agaagaggtc tcactatgtt gcccagacta gacttgaact ccttccctca agtgatcttt    660
ctgcatcagt cttccaaagt gctgggattg caggcatgag ccacctcacc cagccttaga    720
aatgttctgt ttcttgacct gagagctgga tatacaggat tgctcacttt gtgaaaattc    780
```

<210> SEQ ID NO 20
<211> LENGTH: 887
<212> TYPE: DNA
<213> ORGANISM: Homo sapiens

<400> SEQUENCE: 20

```
gtacttcaga gtcaggatgc ctctcttgct ctgggcctcc ttgcccacat aggagtcctt     60
ctgacccatg cccaccatca ctccctggtg cctaggtgc cccacaatgg aggggaagac    120
ggcctgggga gccttgcgca tgctggagca gttgtcgacg acgacgagcg cggtgatagc    180
atcatccatg gtgagctggc ggcgggtgcg gacgcaaggc gcagcggcaa ggacaaggtt    240
ctgtgctcgc tgggctgacg cggtctccgc ggtgtaagga ggtttatata tatttctaca    300
```

| | |
|---|---|
| acatctcccc taccgctata gtaacttgct ctttctttcc ttcctttctt tctttctttc | 360 |
| tttctttctt tctttctttc tttctttctt tctttctttc tttctttttc tttctttctt | 420 |
| tctttctttc tttctttctt tctttctctt tctttctttc tctttctttc tttttctttc | 480 |
| tttttcttcc ttccttcctt tctctctctc tctctttctt tctttctaac tctctttgtc | 540 |
| tctttctttc tttctttttga cggagtttca ctcttgtcgc ccagattgga gtgcaatggc | 600 |
| atgacctcgg ctcactgtag cctccacctc ccaggttcaa gcgattatcc tgcctcagcc | 660 |
| tccctaggag ctggaattac agacgtgcac caccaagcct ggctaatttt tgtattatta | 720 |
| gtagagacgg ggtttcacct tgttggccag gctggtctcg aactcctgac ctcaggtgac | 780 |
| ccacctgcct taggctccca aagtcctggg attataggca tgagccacag tgcccagcct | 840 |
| tcttttcatt taatactata gtagtgtgat cctctctacc tattaca | 887 |

<210> SEQ ID NO 21
<211> LENGTH: 720
<212> TYPE: DNA
<213> ORGANISM: Homo sapiens

<400> SEQUENCE: 21

| | |
|---|---|
| ttctgttttg cggtggttcc tagtatggta cctggccaag ggcacactag atctttgtca | 60 |
| aggtaatgac tacttttat taaatgcttt ccatgtatca agttctgtgc caagcacttg | 120 |
| acatatatca ttttatttta tcccgtgaag tagttattgg tatcttcatt tacaaataaa | 180 |
| aaaacaagct tagtacttaa ctcactgcct tgaacataat tattgcttta aggtagcta | 240 |
| ggattcttaa tagctattat taccaaagca tgaacaatca gtaaaaagca aacctgagca | 300 |
| ttagccccag gaccaatctg gtcacaaaca tattaatgaa ttgaacaaat gagtgagtgg | 360 |
| aaggaaggaa ggaaggaagg aaggaaggaa ggaaggaagg aaggaaggaa atgaagacaa | 420 |
| tacaaccaga gttgttcctt taataacaag acaagggaaa aagagaactg tcagaataag | 480 |
| tgttaattat aatatccagg ggtgggatac agaggtttta gcatctgctc tttgccaagc | 540 |
| actgcactta ttcctgagga ataccctgagg gaaaagtat ggtttctcac aggatctagt | 600 |
| tggactggaa atatgacatt catattggaa tccagtgtct ttttctgaaa aagagagttc | 660 |
| gttccaagct tagctcacat gcaagctaag acaaccacta gaaattactc tccccagggc | 720 |

<210> SEQ ID NO 22
<211> LENGTH: 780
<212> TYPE: DNA
<213> ORGANISM: Homo sapiens

<400> SEQUENCE: 22

| | |
|---|---|
| gtcatgccta cagtgtaacg ggaattgacc aggtaggcga cttgaactcc aactgcaggc | 60 |
| tatggggaga catgtgacaa tgctaatccc ttaggcattt attcagtgca ttgcagttta | 120 |
| aatgtctgcc tttcaggcat tcagagatt atgtcaccta agaggcagg ctggaattca | 180 |
| aaacggcaag ccaggaaaga gagaaaccat gtgattccac cgcagcacaa aactcgttta | 240 |
| gcagctgtaa gcgcctggtc tttgtttatt tttaatttcc tttctttccc aattctcctt | 300 |
| cagtcctgtg ttagtcagga ttcttcagag aaatagaatc actagggaac caaatatata | 360 |
| tacatacaat taaacacaca cacacctatc tatctatcta tctatctatc tatctatcta | 420 |
| tctatctatc tatctatcta tctatctatc tacatcacac agttgaccct tgagcaacac | 480 |
| aggcttgaac ttatatgggg attttcttcc atctctacca cccctgagac agcaagacca | 540 |
| actcctcctc ctccttctca gcctactcaa catgaagata ataaggatga agacctttac | 600 | aatgacccag ttccacttaa taaatagtaa atgtatttcc tcttccctat gattttcttg    660 ataacatttc ttttctctgg cttatttatt gtaagaatac agtatataat ataaataatt    720 ataaaacatg ttaattggtt ctttacgtta tcgataagac ttctggtcaa tggtaggcta    780

<210> SEQ ID NO 23
<211> LENGTH: 780
<212> TYPE: DNA
<213> ORGANISM: Homo sapiens

<400> SEQUENCE: 23
gagcccaagt ttaaacccag gccctctgtg tcccctaca gggtgactgc atctccgagt     60
cctggcttgt catgcctgac agagggctgc cgagtgagca gcttaaggca tcctgccact    120
gtgcagctgc caaccctaca gcccggcagc cctgcgggag gaagctctag tgcaggcctc    180
ttaggatctg gggtccagga tgctgatttc agggccggga ccttgggcac cgtccctctg    240
gtctgcataa gacccactat gggcaaacct taaacctgat cgttggaatt ccccaaactg    300
gccagttcct ctccacccta tagaccctgt cctagccttc ttatagctgc tatggggct      360 agattttccc cgatgatagt agtctcatta ttattattat tattattatt attattatta    420
ttattattac tattattgtt ataaaaatat tgccaatcat acattcgcgt gatcactcac    480
actgtgccgg gcactcttga gagcacttta catatattgt ctcatttaat tctctcaact    540
tgggcacagg cactgtcact atttccattc tacagctgag gagactgaag cacagagagc    600
cttagggact tgcctgaggt cacacagcta agaaatggtg gagccaggat cagaaaccag    660
gccacctaca gagctccctg caaggggaac agcatccggt tccagaggct gtgattttat    720
cagctacact gtgtgactcc atcttcacac tctcctgccc ctcaagaaga catataacct    780

<210> SEQ ID NO 24
<211> LENGTH: 780
<212> TYPE: DNA
<213> ORGANISM: Homo sapiens

<400> SEQUENCE: 24
atgaagagat ggtcaggcga ggtatggggg aaggggcgtg gagcttccat gtcctccctg     60
ggcgccaccc tccaggaacc tccacgtgtt cagctataca gaagcttcct gaacccagtc    120
ctcttggggt ttgagggaag cttcatgaca tcagcattcc ttcctccagg gtattaatgg    180
gaccctctct gaagagattc ttaagaccca cggccagaaa gttgggtaaa gactagagtc    240
ctgccttggg gcaggtgaaa ggagtgcaag agaaggtaag agagattctg ttcctgagcc    300
ctaatgcacc caacattcta acaaaggct gtaacaaggg ctacaggaat catgagccag    360
gaactgtggc tcatctatga aaacttctat ctatctatct atctatctat ctatctatct    420
atctatctat ctatatcata acaccacagc cacttagctc caattaaaa gattaatcat    480 aaacatttgg gaaggagagt gaagattttt gtgatgttaa ataagaatga ttatactaaa    540
aaccaaaata atatgttatt tatggctggg tgtggtggct taagcctgta atcccagaac    600
tttgggaggc caaggcttgt ggatcacttg agcccagaag ttcaagacca gcctgggcaa    660
catagggaga ccctgtctct acaaaaaatt ttaaaattag ctggacatga tggcacgcac    720
ccgtagtctc agctactcag gaggctcacg ccactgcatt ccagtctggg taacgcacac    780

<210> SEQ ID NO 25
<211> LENGTH: 780
<212> TYPE: DNA

<213> ORGANISM: Homo sapiens

<400> SEQUENCE: 25

| | | | | | |
|---|---|---|---|---|---|
| gtcaggagtt | cgagaccagc | ctggccaaca | tggcgaaacc | ctgtctctac | taaaaataca | 60 |
| aaaaaattag | ctgggcatgg | tggtgtgttc | ctgtaacccc | agctactcag | gaggctgagg | 120 |
| caagagaatc | gctggaaccc | aggaggtgga | agttgcagtg | agctgagatt | gcaccactgc | 180 |
| actccagtgt | gggcaacaga | gcgagactct | gtctcagaaa | aaaaaagaa | tacatgaaat | 240 |
| cagagaaact | caaattgtga | tagtagtttc | ttctggtgaa | ggaagaaaag | agaatgatat | 300 |
| cagggaagat | gaaaaagag | actgtattag | taaggcttct | ccagagagaa | agaatcaaca | 360 |
| ggatcaatgg | atgcataggt | agatagatag | atagatagat | agatagatag | atagatagat | 420 |
| agatagacag | acagacagac | agacagacag | acagatgaga | ggggatttat | tagaggaatt | 480 |
| agctcaagtg | atatggaggc | tgaaaaatct | catgacagtc | catctgcaag | ctggagaccc | 540 |
| agggacacta | ggagcatggc | tcagtccagg | tctaaaagcc | aaaaaaccag | ggaaactgat | 600 |
| ggtgtaatta | tccatcccag | gtggaaggcc | tgagaacctg | gagtgcccct | ggtataagtc | 660 |
| ccagagtaca | agacaggag | agcctggagt | tctgacttcc | aagggcagaa | gaatgtgtcg | 720 |
| cagctccagg | agagagagag | aaagaatttc | tttcctccgc | cttttgattc | tatctggggg | 780 |

<210> SEQ ID NO 26
<211> LENGTH: 540
<212> TYPE: DNA
<213> ORGANISM: Homo sapiens

<400> SEQUENCE: 26

| | | | | | |
|---|---|---|---|---|---|
| cttgaacctg | agaggcagag | gttgcagtga | gccgagacca | tgccattgca | ctccagcctg | 60 |
| ggcaatagag | taaaactcca | tcctcccgct | ccaaaaaagt | agacaacgtc | catgaggtga | 120 |
| tgaggaaggg | gttatcgtgt | gttgcttgct | gagaacagga | cccccagact | caccgtgtcg | 180 |
| acgccggcca | gcagcatctc | agtcacgttg | gcgtagatct | cctgcagcgt | cagagcctgg | 240 |
| ctaaggaaga | ggtatgtgag | aagtcccccg | ctcaccctcc | ggcctcggtc | catttggtac | 300 |
| tgtatgtccc | tcaacttgtt | gtcaacatga | atttggcctg | tttgaaaaca | gtatttcttt | 360 |
| tgaaaggagt | ttgggttgag | aatcatcttt | tcagtctcaa | agccctctgt | cctcccagta | 420 |
| gcttaactaa | accagtggca | ggtgacagag | ggtaaggaaa | cccaatttat | ctaacgtcaa | 480 |
| cctgggagtt | tcactcatac | acttgcttat | gtaaatgaat | gaaaagttaa | aagacaagct | 540 |

<210> SEQ ID NO 27
<211> LENGTH: 537
<212> TYPE: DNA
<213> ORGANISM: Homo sapiens

<400> SEQUENCE: 27

| | | | | | |
|---|---|---|---|---|---|
| agagagccca | ggagacaggc | agaaaggaag | gcatgtgacc | ggatcacaat | catcagctct | 60 |
| ctgctgtcct | ctttgggaag | ggttttagta | ttaaaaggac | atttattctc | attaatgcaa | 120 |
| aattaaggag | ttttaaaagc | ttttacaacc | tagactccct | ctgagaggtt | agccttgaca | 180 |
| ccctaatcgc | cttctgctcc | cgccactgct | cggtgccaag | cagctcccac | ggccccggcg | 240 |
| ggtctgatga | tagccggaca | gggaggagga | agggaggag | gaagagcctg | catcagctcc | 300 |
| tacgattgcc | cagccccatc | ctgggagtga | ttaaacggtg | catcaccaaa | tgccagtccc | 360 |
| actgacaggc | aggtcaccgt | gcacttcagg | gcactctaaa | ttgccgactc | tccatgtaga | 420 |
| gagggatgaa | tccaatattg | aaatcctcat | aactacagcc | ccccaaagta | gccgtccatc | 480 |

```
ttctgcttaa aatgttgatc tgtagtaaaa tgttgatttt gttgaagctg agtgatg        537
```

<210> SEQ ID NO 28
<211> LENGTH: 609
<212> TYPE: DNA
<213> ORGANISM: Homo sapiens

<400> SEQUENCE: 28

```
ttgaacctag gagatggagg ttgcagtgag ctgcgatcat gccacttccc tccaggctgg       60
gcaacagagc gagactccat ctcaaaaaaa caaaaaagaa aaccaacctt tgaatgtag       120 gggaaacttt tcaaaggata tctagttttc aattacagta aacttgtgga agggaggttc      180
agagttgaga ttgagattat agattttgct gatgataaac catgagttcc agaggacata     240
gtagactatt ctgggcagtt atacaggggt ggatggaatg tgggagtggg gttgtatagt     300
gccataaaga aatgagagtc cggattaaaa ataatgagct ggactcgcga gccttttgta     360
actgaaataa atagaaaaat aagaaataca ttatttctgt gattgttgag aggaagaaat     420
ggtggaaatc ttgtgagaag cacactgagc tctagcacca cctcttcact cctacagatg     480
gtggaataaa cggcaggcaa gttcaaaatc acatatagtc attattgcaa gatagttcta     540
tggatataga tactacatac aatataaatc atgctcattg aatggttcag tggaaactac     600
tctgaactt                                                             609
```

<210> SEQ ID NO 29
<211> LENGTH: 732
<212> TYPE: DNA
<213> ORGANISM: Homo sapiens

<400> SEQUENCE: 29

```
gagtttggga agggtatttt aggggggaat aacttttgag ttcccagcgt gcggggaag       60 ggcgggacgg gagggtgtcc caaggcctga gaagatcagt gtgggcagg ggtcaggaat     120 aacctgggag ggggccttgt atgggggaaa taattgggaa gaggagagat gggatgaagg     180
gggcctcagc gggtcgtctc ctgtgtatgc agggtcgttc tgcagcgtct ctggagatg      240 gcgtccctgg gagccctcag gtcgcccta cccgctgcgg ggtgctttcc tggcgtcacg      300
ccttcctggc ccctggaggg aaggaagtga aactctcctc ttcccccacc cggctggaat     360
gcgagtcagg aagcctgggg ctccagcctg ctccggctgc ccgggtcggg gatggggagg     420
ggcgtggccg gagcgcaaag ccccgcccct ccgcgccccc ccccggaag ccccgccgcc      480 ggccgctaag gcgatcacgg gccctgtcct aatatgggca accggaagcg gcccgcgcga     540
ctgccctacg tcactccgtc caaatttagt tgtggaagtc agcgggcgct ggtggcggga     600
aggcgccgcg agccagtgcg ggcggaaagg gggcggggg cgcaccaccc cttaaagggc      660
ccgcaccagg aatgaatgga gccattcgaa caattctgca tcctattttt ggaggaagtg     720
gaattagtat tt                                                          732
```

<210> SEQ ID NO 30
<211> LENGTH: 488
<212> TYPE: DNA
<213> ORGANISM: Homo sapiens

<400> SEQUENCE: 30

```
tttattttta aaaagaaag aaagaagaga aagggatgg gtttattgtc cttttcaaca       60
gactagagta tacggggtga aactgcttca cttgattcaa taaaatcgtt tccggtaaca    120
```

```
ggccccagga atcctagacc taagcctggc gcgaaactac atttcccaca atccttcggg      180
ggctgataag gctccgcaat ggtctgaact acaattccca caatccaggg cgatttccgc      240
tttgtcgcgt ttcctcaagg ctccgcccca tttcccatct ttcttttcag tccttgcgca      300
ccggggaaca aggtcgtgaa aaaaaaggtc ttggtgaggt gccgccattt catctgtcct      360
cattctctgc gcctttcgca gagcttccag cagcggtatg ttgggccaga gcatccggag      420
gttcacaacc tctgtggtcc gtaggagcca ctatgaggag ggccctggga aggttagtgt      480
gtaagggg                                                               488

<210> SEQ ID NO 31
<211> LENGTH: 248
<212> TYPE: DNA
<213> ORGANISM: Homo sapiens

<400> SEQUENCE: 31
accctcattt cacatttcac cccttcctca aaatgctccc ttcatattac ctcctcagaa       60
accaagaata tggctactaa ttctccctgg ccccatgctg caggtgaacc ggtagcccag      120
aggtatcaca taattctccc aaagtcacac agcaaatcaa gatgcatcca ggactagaag      180
ccatgtcagc cacactggga agccccagcg aagctgacag aaagtttcat aataccaccc      240
tctcccct                                                               248

<210> SEQ ID NO 32
<211> LENGTH: 480
<212> TYPE: DNA
<213> ORGANISM: Homo sapiens

<400> SEQUENCE: 32
aaacacccca gtctgaaaat aaccatagtt tgttgctctt acgagtgaaa atgctatttc       60
atacacgaag ctttgtcctt cagcacccaa gatttaagga taattatgga tgaatattat      120
ggattcattt taaatccttt ggcaaatctg ctctgggggc ttctctgtca gaaggtctct      180
ccttcccaac tctaagaaac gttattccta tgcaaatgct gctgagtcaa gacggggagg      240
gaagtgcaga gagaagggct ggtggcatgg tcagtaagtc atgagggtga gattagtggg      300
gacacactgc ttgccaacgt aggagaaggc tctgccctca cctagcaggt ctgatggaag      360
ccccttattc cgtccttcct gccgggttcc accgagatcc aaaaaggaat gctgtgtagg      420
agcacatgat atgtgataaa tgagagaaag gtcaaacatt taaggaacgc ccagagaaag      480

<210> SEQ ID NO 33
<211> LENGTH: 463
<212> TYPE: DNA
<213> ORGANISM: Homo sapiens

<400> SEQUENCE: 33
cgctgggcgc gagtgaagag cccatcaggc aggtcgcgca ggaagcgctt gagcgccgag       60
gaaacatcat ccacgtgctg ctcgccctcc ttgaggtgca cagagcgcgc atcctgccgc      120
aggctctcca gcagccgctg tgtcttcgat gtctgcccac acttgcggta gatgccctcg      180
gaggtcaggc ctagggaggg gcgggccaa gcgttcgggg cctgaggcat agagtcatgg      240
ggcggggccg cgcagctctg gggcgggagg cggctctccg ggaggggcgg ggctggcacc      300
ctaggggcag ggctcaccgc actgcgtgat gtagtccaca cagcggtaca cgatcaccgg      360
gatatccgag tccccaagct gctgctccga cagcgtgtcc cccatgctgg cggctgcttt      420
ctggatggcc cccagccaac ccatgaagtc cagccgccgc tcg                        463
```

```
<210> SEQ ID NO 34
<211> LENGTH: 324
<212> TYPE: DNA
<213> ORGANISM: Homo sapiens

<400> SEQUENCE: 34
cgatcccgtt cactcgcctg cccatccgca tggccaaggg gctgggcaac atctctgcca        60
agtatcgctg gttcgccgtc ttctacctga tcatcttctt cttcctgatc ccgctgacgg       120
tgtttggcct ctcgctggcc ggctggcggg tgctggttgg tgtcggggtt cccgtcgtct       180
tcatcatcat cctggtactg tgcctccgac tcctgcagtc tcgctgccca cgcgtcctgc       240
cgaagaaact ccagaactgg aacttcctgc cgctgtggat gcgctcgctg aagccctggg       300
atgccgtcgt ctccaagttc accg                                              324

<210> SEQ ID NO 35
<211> LENGTH: 264
<212> TYPE: DNA
<213> ORGANISM: Homo sapiens

<400> SEQUENCE: 35
cgcgagagga ggggaatggc aggtccccgc ttcgcgtacc ttggaaataa gctcatcgtg        60
tttggccagg tgtgcacggc agtggacaca gctgtaagtg cggtgacagc ggggcagata       120
gctgcggaaa gtcttggtgg ggaggcaggc agggcccgga ccggggtcac agctgggcat       180
gacgggctgg aggacaatgc cctggtgggc tggaggggct ggcgccgtgc agcccccgca       240
gagacggtcg caggtgaagc agcg                                              264

<210> SEQ ID NO 36
<211> LENGTH: 300
<212> TYPE: DNA
<213> ORGANISM: Homo sapiens

<400> SEQUENCE: 36
cggtgctcac cggctcgacc ccccagcaac acgagagacc tcacagaggg agtcacacta        60
acgtggtcgg ggctccagag cgaaaccccca accactatgc tcacagccag gaccgagcag      120
gctgggccaa cggcagtccc tgcccagcgc ccggctccct ccgagtggcc agcagcgccc       180
tctggtggag actggctcgg cctccgcggc actgcattcc cacggcagtg gtccatctag       240
tccccaagtc ctagaggagg cccctctctc tccctcagcc ctggcagggt ccttggcgcc       300

<210> SEQ ID NO 37
<211> LENGTH: 482
<212> TYPE: DNA
<213> ORGANISM: Homo sapiens

<400> SEQUENCE: 37
ctgagagcca tggcgagagc aatgctaggc cggtgaacag taggctcgag tttaggtttg        60
aaaggtgagg tgagagaaat cggcaaaggg aaccccctgcg cagatctcgg gttcctttac      120
tttataaccg cgggttccgg ttcctgccag gtgactgcac agttcatcct catgacccctt      180 ctcagccaat gggaagagag cgacgcccag gaagtcccgc cctgtcccgg cctgtgggcg       240
cgtcctcggg tccttctacg tcgctgactc gtgacctgac cggtattttt ttcctaaact       300
gggatcttgg gtaggaggaa gaaaagataa ggagttcctc tatctgaaat tagtcgggct       360
gttttgagga gtactggtta ggtatattgg agaatgtgcc tttattggaa ttttttcgcat     420
```

```
aattacacag ggttatgggc ttaggggtac atgattgttg gccgggcgtg gtggctcacg    480
cc                                                                  482
```

<210> SEQ ID NO 38
<211> LENGTH: 1301
<212> TYPE: DNA
<213> ORGANISM: Homo sapiens

<400> SEQUENCE: 38

```
ttgcagggct agccaggata agcaatggat gctgtttaat tcatcttagc ctcagaatgg     60
atcaagagta aggtgctatt ccctctcaaa ggaaacgcta attaaatgat ccttggtgaa    120
actcaggctg agggctcaga ggtgtggtga tgtaatgggc tttggaatta gacagggact    180
gaacatttgc ttttgaaatt tactatctat gtaccgttgg aaaatttact taatatctct    240
gaattttttt tcttcaactg tggagtgagg aaaataatac ctactttag gtagatgatg     300 gatataacac ttttctctgc atatagtaga cactcagtgc ataactatcg ccttcctttt    360
ccctctactc agaaacaagg acatctggga ccacagccac atacttacct ccagtcgttt    420
catatcaacc aactgagctc taacattttt ctgcagaagc tggatatgct gtactttttc    480
tatgactttg cgcttcagga cttcaattct gcttctcaga tcctctgaca ctcggttgta    540
ggtattatca cggtctgaaa tcgaaaatat ggttattgaa gtagctgctg agtgatttgt    600
ctgtaattgc cagcaaaaaa gaaggaagaa aggaaggaa ggagaaagaa agaaagaaag     660
aaagaaagaa agaaagaaag aaagaaagaa agaaagaaag agaaaaaaga agaaagaaa     720 ctagcttgta aatatgccta attttatttt ggttacagtt taatctgtga gttcaaaacc    780 tatgggcat ttgacttttg gataatgtta tgccctgcag ccttccatga atgccagtta     840
agatgtccta atagcaatta gtaatcccaa agaaatatag aagaagaact ttctttggaa    900 ttttaaggt gtaatttgga gttaaaatag ttggtttgat tgcatttcaa ttatttata     960 acatccttaa tcaagggact tgaacatatt ggattttctt actgatgagc ttttcttttt    1020
aatctataga tttgaaatgg ttcctaagct gttttgggtc aacaggatca ctcacttgcc    1080
agctagtgtt gcatcactga tttaaatgt caagtgtttg tgaaggtgta aaaaggcaaa    1140
gcaaaacttg agaaactgag gactccctag actcgctgtc catgcccaga gtgaatgcaa    1200
tgtttcctaa ccctaatgag tagactgtga gaatgacgta gcttgaccct atattttaaa    1260
tttaaaaatc tacctaatca gctcagtgga gtctgggagt t                       1301
```

<210> SEQ ID NO 39
<211> LENGTH: 660
<212> TYPE: DNA
<213> ORGANISM: Homo sapiens

<400> SEQUENCE: 39

```
gaactgaaat tcggagggga gctaagagct ccatgttttt attttactat tctttaaaca     60
agcagacaca gtgctggttt ctgatcatgt gggaggtgtg taggagagaa cacaggtaaa    120
gtaaaataaa aatataaagc cataaatgcc acaacagaaa ttcaatgaac aaacatagaa    180
gagaatacct taattcctag aagacagaga gaagagttta tgaaaggcat cctagaagag    240
gagatatttg cactgattct taaaggtga gagtacaaga cttcctctcc aggagtcggc     300
ggagggaggg cagactcaaa gtgctcctgg acgcagaggc tcttgtcaga gggcacagac    360
cggttggaac aaagtaagga tctgagcgac cccaactttg cagccgaggc ctccagctcc    420
gaggtgcata gcaaccctag ggttccggta ggcgttcctc cgtccgcgac cctggcagag    480
```

```
ccgcagagcc ctcctccaga cccgaccact gccccaggcc ccgagcgacc ggaaggctca      540
gcagcaggcc gcggagaagg gcggcgccca ccaggcccct agcactgccc agtctggccc      600
ggcacagctg ctgcagaagg cgcacgacga gctcgtgtgg tacatgcggg tcaaggacca      660

<210> SEQ ID NO 40
<211> LENGTH: 349
<212> TYPE: DNA
<213> ORGANISM: Homo sapiens

<400> SEQUENCE: 40
cgcggacctc ggactcacca agtgccgagt ggcagatgtg ctgctgaggg tgcgccgggg       60
cgcagctgca tgcctcaccc agccccgggg gccgcagcaa cgccagcagc cgcagcaaca      120
gcacccagct tggcgcgggc cgagggctcc caggcatgac actgcagatc cgcgactgag      180
cctgtgaggt ctgggggact ggacggcccc agcagggctc cttcccaagg ccgttgtgcc      240
cctcgcccca ggctttatga ggtggcccta agggccaatc ccgccccgac gggctccgcc      300
ttcctttggc tctaggccac ccgcggaggc aggacccgag gctcttccg                 349

<210> SEQ ID NO 41
<211> LENGTH: 422
<212> TYPE: DNA
<213> ORGANISM: Homo sapiens

<400> SEQUENCE: 41
cgcgtgccac ggggaggagg actgggggcg tttgagggge tcagcgcacc agaggagtga       60
ggtggaggag ggcgttcccg cgtcctcctc ttcaatccag agcagctcaa cgacgtggct      120 cccttttctat gtatccctca aagccttcgc gtcggattaa aggtgttctt gatccttctt      180
taccaaccac ggtgcgggcc aggcgtgatg agggatgagg gagaggaaac ctcagtagca      240
aaattgttca gaggacgttc ggagggcgcg ggagcagcc ggatgcacac ctaaagtctc       300
gcaacaccca actcctcctc cgcaggcagt cccttaagag aatagataaa aaggccaagc      360
aaagatcctc tccccctcggc cccggggcac tgccacattc agtctaggca tccccttctg      420
ct                                                                     422

<210> SEQ ID NO 42
<211> LENGTH: 620
<212> TYPE: DNA
<213> ORGANISM: Homo sapiens

<400> SEQUENCE: 42
gctcgggtcc gggggtgtgg atgaaggagc cccaggcagt ctcatgagca cagagagcac       60
cgtaggctgc ggtgagctcc ggctcatcct cccagctaca tgactgcagc ctcctatgcg      120
catcccagcg ggcatggatc agggccagtc cctgagcatc cttggccagg aagctcaggt      180 acccccagtgg gttgccaggg acggcccttgg tcaagtggca ggaggtcctg taccagcgga      240
gggcagggga gcccccagg gccaccccca ggaagcccag catcccaaac agccctgcct      300 gaaccccat tctgcactgg cccagtccag tcagacaaag cccctgggat gcctgccctt      360
ggtggcccca ccaggcggca gctgagcagt ggaacggaag cggagcccag caggcccggt      420
gcggcgggac caatgaatgg agctgcggga ggaggaggaa agaggctgga gtatggggtg      480
atcttgggct tgtaaccgaa tccaccagcc gggcaggacg ctgattggct gaggagtgca      540
cttgccaggg cccacgcccc cattctgcct gccttctcag caccatccag tcacctgctg      600
```

```
ccagccctgc ctagattggg                                                  620

<210> SEQ ID NO 43
<211> LENGTH: 1012
<212> TYPE: DNA
<213> ORGANISM: Homo sapiens

<400> SEQUENCE: 43
cggcgcgctg gctccctgga gcggggcggg acgcggccgc gcggactcac gtgcacaacc        60
gcgcgggacg gggccacgcg gactcacgtg cacaaccgcg ggaccccagc gccagcggga       120
ccccagcgcc agcgggaccc cagcgccagc gggaccccag cgccagcggg accccagcgc       180
cagcgggacc ccagcgccag cgggacccca gcgccagcgg gtctgtggcc cagtggagcg       240
agtggagcgc tggcgacctg agcggagact gcgccctgga cgcccagcc tagacgtcaa        300 gttacagccc gcgcagcagc agcaaagggg aaggggcagg agccgggcac agttggatcc       360
ggaggtcgtg acccagggga aagcgtgggc ggtcgaccca gggcagctgc ggcggcgagg       420
caggtgggct ccttgctccc tggagccgcc cctcccaca cctgccctcg cgccccag          480 cagttttcac cttggccctc gcggtcact gcgggattcg gcgttgccgc cagcccagtg        540
gggagtgaat tagcgccctc cttcgtcctc ggccttccg acggcacgag gaactcctgt        600
cctgccccac agaccttcgg cctccgccga gtgcggtact ggagcctgcc ccgccagggc       660
cctggaatca gagaaagtcg ctctttggcc acctgaagcg tcggatccct acagtgcctc       720
ccagcctggg cgggagcggc ggctgcgtcg ctgaaggttg gggtccttgg tgcgaaaggg       780
aggcagctgc agcctcagcc ccaccccaga agcggccttc gcatcgctgc ggtgggcgtt       840
ctcgggcttc gacttcgcca gcgccgcggg gcagaggcac ctggagctcg cagggcccag       900 acctggggttg gaaaagcttc gctgactgca ggcaagcgtc cggagggggc ggccaggcga      960
agccccggcg ctttaccaca cacttccggg tcccatgcca gttgcatccg cg              1012

<210> SEQ ID NO 44
<211> LENGTH: 295
<212> TYPE: DNA
<213> ORGANISM: Homo sapiens

<400> SEQUENCE: 44
cgcgctgagc ggttggtgag gagacagggg tcatcgtgca ggttgtcaaa gggcagcagg        60
gcccggccgt tgtcttggaa gcgctggttg acggccagca gccccagctg gttggacatg       120
ttgcgcaggt tcctgccag gggctcctcg ctgccgtaca ccatgctggc gtccacgaag        180
gaagtgagcg cgttgatctg gttgcggatg gtgatgttgc tcccggggca agccgggcag       240
gagcggaaga acgggatgca gtcggcttgg ttcttgatgc gggggtcatt gggcg            295

<210> SEQ ID NO 45
<211> LENGTH: 801
<212> TYPE: DNA
<213> ORGANISM: Homo sapiens

<400> SEQUENCE: 45
tgcccaccag aagcccatca ccaccagcaa agccaccacc aaagccacca cccaagccag        60
caccaaggcc accaccatat cctcccccaa agccactacc aaagctgctg ctgctgctgc       120
tgaagccacc gccatagccg cccccagcc cgcaggctcc cccagaggag aagcgggagg       180
atgagacaga caggccgccc ccgtaggtgc tgggggcgcg gcaggaccct ccggccagga       240
cggaggagat gcggctggag ccgcccccga tgccgccccc gatgccgcag gagcccttca       300
```

```
tggagctgga ggaggtgaac tgcggctgc  aggtggtcat ggtgcagagg agggaggtga    360
gcgagcgagc agttggctga gtgaagagaa ggtgctcggg taaattggaa agggatgcga    420
gtgctttata ctcgtgggta gggggcgggt ctggcacttt ccattcccct tggctttcat    480
cacccacagg ctagcgccaa ctcccagcca ggtccctcct ctcatccgcc tcatcatgtc    540
tgtcatattt tactggaaac tcattgtttg gagtgttttg ggctttcttg tcccgccagg    600
cgtgattcac aggggaggt  gtgggcctgc aggctacact ttcccatcgg accctgggag    660
tcccagccct caggaacccg cgcactgggc ttagccaggg tgacagagag cagggcctct    720
gcaccttaaa cctagttacc tgctagctct ccatgaactg aatgggcctt taacatccac    780
gtagaggaag cctgctgctg c                                              801
```

```
<210> SEQ ID NO 46
<211> LENGTH: 434
<212> TYPE: DNA
<213> ORGANISM: Homo sapiens

<400> SEQUENCE: 46
cgatggagga catcgtcatg gtcacaggga tggcgtcgaa gtaggacgag tgaggcgcga     60
gcgtgaggat ggccgcctcg gtgggcagcg cctgccgccc cttcacggcc acccggtgga    120
agccgccggc gaaccacatg gtgcgcatga tggccttcag caggaagtcc acaaccctgc    180
aaaagagggc gctgcgtcac gcgggcacac gtccgcagtc tcggagtctg tgtgaggcac    240
aggggcggtc ccacgggaga gccctccagg gcgcagtcca ggccacgggc ttcctgtggt    300
cgccgccgct gggacatctg cttgagggaa gaaaagacgc gcgccttcc  tggcctccgc    360 ctgtgtcctc gctggctgcg ctctcaccta cgaaggaggc cgcggggccc tgtgtggtgg    420
tcacgggcca cgcg                                                      434
```

```
<210> SEQ ID NO 47
<211> LENGTH: 411
<212> TYPE: DNA
<213> ORGANISM: Homo sapiens

<400> SEQUENCE: 47
cgtccatctc ggccttcgaa ggcacgtgcg tctccatccc ctgccgcttt gacttcccgg     60
atgagctgcg gccgctgtg  gtgcatggtg tctggtactt caatagcccc tacccccaaga   120 actaccccc  ggtggtcttc aagtcgcgca cccaagtagt ccacgagagc ttccagggcc    180
gcagccgcct cctgggggac ctgggcctgc gaaactgcac cctcctgctc agcaacgtca    240
gccccgagct gggcgggaag tactacttcc gtggggacct gggcggctac aaccagtaca    300
ccttctcaga gcacagcgtc ctggatatcg tcagtgagtc cccagcggtt gtgcaggcac    360
cgggagctgg ggcagcgggg cgggaaggag tgtggccgga aggcctcccc g             411
```

```
<210> SEQ ID NO 48
<211> LENGTH: 600
<212> TYPE: DNA
<213> ORGANISM: Homo sapiens

<400> SEQUENCE: 48
cgggtggctc caccctgcgt cgggcctcag tcagcccccg ggggaggcca tgaacgccac     60
ggggaccccg gtggccccg  agtcctgcca acagctggcg gccggcgggc acagccggct    120
cattgttctg cactacaacc actcgggccg gctggccggg cgcgggggc  cggaggatgg    180
```

```
cggcctgggg gccctgcggg ggctgtcggt ggccgccagc tgcctggtgg tgctggagaa    240
cttgctggtg ctggcggcca tcaccagcca catgcggtcg cgacgctggg tctactattg    300
cctggtgaac atcacgctga gtgacctgct cacgggcgcg gcctacctgg ccaacgtgct    360
gctgtcgggg gcccgcacct ccgtctggc ccccgcccag tggttcctac gggagggcct    420
gctcttcacc gccctggccg cctccacctt cagcctgctc ttcactgcag gggagcgctt    480
tgccaccatg gtgcggccgg tggccgagag cggggccacc aagaccagcc gcgtctacgg    540
cttcatcggc ctctgctggc tgctggccgc gctgctgggg atgctgcctt tgctgggctg    600
```

<210> SEQ ID NO 49
<211> LENGTH: 540
<212> TYPE: DNA
<213> ORGANISM: Homo sapiens

<400> SEQUENCE: 49

```
cggggcgagc acgtgcacct cgtgaccacc ggctctctag agcccaggc agaggcccag     60 ctctgcagta gggaaggcat cgggagtgcc agggtgaacg taccccaagg gcccggcacg    120
actgacctct cgtgcctgct ctctcccttc ctcgccaagc cccgtgatg tgggaagcca    180 gcgtgaggcc ggtggggcag ccgccttccc gtggctgtgc caagtccccc cggtcctctg    240
cacatcatgc ctccttccac accctgacag gaagcagctg ggagaagccg ttgggtgcac    300
tcactccctg atttacgaca agttccttcc tcagcgcctc tctctcctgc ctcctcctgc    360
tctcctgccc tcccctgggc ctcgggaggt gccacgcaag cccaagaagc atcagcatac    420
tgtccctccc tctcctgtgg ccacgggctc cccagggag ctgagagtag cagcagctca    480
cagcccaagc caccttgcc cgtttctagg caggtggtgg caccaggcac gaaggaagca    540
```

<210> SEQ ID NO 50
<211> LENGTH: 224
<212> TYPE: DNA
<213> ORGANISM: Homo sapiens

<400> SEQUENCE: 50

```
cggtgacccg gccgggtcga agggcagagt tccgctgtca ctagccctcc acccgtcctg     60
tgtgctggga tgccctcgcg gcgccgtcca cgccaccgcc gcccctctct tgtgggttctg    120 tctcctccgt gtctaggatc ctcctgcatc cgttttttcct tcctcccttc tctccctccg    180
tctgtcttgc ccgcacctga ggttgtcgca gaggcgctga gacg                     224
```

<210> SEQ ID NO 51
<211> LENGTH: 316
<212> TYPE: DNA
<213> ORGANISM: Homo sapiens

<400> SEQUENCE: 51

```
cgcgggctgc ggggctgcgg ggagggaggg gcgggttcag ggctgtgggc cccgcccggg     60
gcaccgcctg gatcaggcct gaggccggct gcagagaact tgggcaccgc ggaccagatt    120
gctggtcacc aggatgaaaa ataaaaaaga cccaaacagc tcccccgacc ccgccttcgc    180
gcaggcccct ggcgttctgc tcagggggttt ttgtttaatg aagaacgtca aacatctggc    240
aaggtcggaa tgattttgcg atgagcaccg cctggattct gcggtgaaag cgactgtgtg    300
cgcgctcacg gcctcg                                                    316
```

<210> SEQ ID NO 52
<211> LENGTH: 372

<210> SEQ ID NO 52
<211> LENGTH: 372
<212> TYPE: DNA
<213> ORGANISM: Homo sapiens

<400> SEQUENCE: 52
cgggcgccgc cccccttcct cctccatcag caacaggcgg cgccggccag cctcatagtc     60
agcctcatcc acactgacca gcaggcgaac agcctcccgg cccacagcct ctcgcagggc    120
ctcagtcagg aacacgcccc gcagggcctg cagcagggcg ccactcaggt agtcgcccca    180
gaaggcgtcc agataggaga gctctgagaa cttgatgtca caaccacag agcccaggtc    240 ccttgagcgc agcactgcgg tggcctgccc aaacacgtcc agctgccgcg ccagcgcctg    300
gggccgccgg gatgccacgc cctgctccaa ggctggccca tgctcgcagt actctgctcg    360
aacccggagc cg                                                        372

<210> SEQ ID NO 53
<211> LENGTH: 258
<212> TYPE: DNA
<213> ORGANISM: Homo sapiens

<400> SEQUENCE: 53
cgcccagggc caggccgttg atgatgacgg ggcccccgtt gaggagcact gctggggagc     60
cgctggctgc caggaagctc ccgttcacca ggatggagga ggaagccggg caaggcgcgg    120
gagggccggt ccctgccagg aatatggagc cctgggcagc ggcctcggcg gacactgggg    180
ccgcccctct ctccaggtcc tcaggacttc ggctggactc gtcctcagtc gtgggattcc    240
catcagactc gctggccg                                                  258

<210> SEQ ID NO 54
<211> LENGTH: 398
<212> TYPE: DNA
<213> ORGANISM: Homo sapiens

<400> SEQUENCE: 54
cgccttttcc ttcggtcact cagaccgcgc ccgaggtccc tggtgccccc gcggggagc      60 tgaggtttgc ggtccctcct ggggttcgct tcccgcgggg ctaaaccgcg gcgaccaggg    120
cccctttctc cactggtgcc ttttccggga aacgctgctc cttagatgga cgaatacgta    180
ctcggtaccc agcacatcct ggacgagtta acttccttaa tttccatatt tgccggagaa    240
ccagctggtt cagagcgcac agcaaacggg agaagttaaa ccaggttccg cgacccagag    300
cccaggggtg gccccgggga cacccacctg actccgcacc ccccacgaga gggaggatc    360 cttgcagacc tcacctttgc tggcaacgct gcggcccg                             398

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
aagagcccat caggcaggtc                                                 20

<210> SEQ ID NO 56
<211> LENGTH: 29
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 56
gtttcttgtc gagcagcacg tggatgatg                                    29

<210> SEQ ID NO 57
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
ctccagaact ggaacttcct g                                            21

<210> SEQ ID NO 58
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
gtttcttaac ttggagacga cggcatc                                      27

<210> SEQ ID NO 59
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
tggaggacaa tgccctggtg                                              20

<210> SEQ ID NO 60
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
gtttcttggc ttcacctgcg accgtctc                                     28

<210> SEQ ID NO 61
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
ccctccgagt ggccagcag                                               19
```

<210> SEQ ID NO 62
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 62
gtttctgacc actgccgtgg gaatg                                          25

<210> SEQ ID NO 63
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 63
cttctcagcc aatgggaaga g                                              21

<210> SEQ ID NO 64
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 64
acgtagaagg acccgaggac                                                20

<210> SEQ ID NO 65
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 65
tacagacaaa tcactcagca gc                                             22

<210> SEQ ID NO 66
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 66
gtttcttgtc tgacactcgg ttgtaggtat t                                   31

<210> SEQ ID NO 67
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 67
gcagcaggcc gcggagaag                                            19

<210> SEQ ID NO 68
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
cagcaacagc acccagcttg                                           20

<210> SEQ ID NO 69
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
aggaaacctc agtagcaaaa ttg                                       23

<210> SEQ ID NO 70
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
cgtaggctgc ggtgagctc                                            19

<210> SEQ ID NO 71
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
cagcctagac gtcaagttac ag                                        22

<210> SEQ ID NO 72
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
cccagctggt tggacatgtt g                                         21

<210> SEQ ID NO 73
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 73
gagaagcggg aggatgagac                                                    20

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
gccttcagca ggaagtccac                                                    20

<210> SEQ ID NO 75
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
gtgcatggtg tctggtactt c                                                  21

<210> SEQ ID NO 76
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76
cagcctgctc ttcactgcag                                                    20

<210> SEQ ID NO 77
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
ctccctgatt tacgacaagt tc                                                 22

<210> SEQ ID NO 78
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
aagggcagag ttccgctgtc                                                    20
```

<210> SEQ ID NO 79
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
cggaccagat tgctggtcac                                               20

<210> SEQ ID NO 80
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
agcctcatcc acactgacca g                                             21

<210> SEQ ID NO 81
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
gccaggccgt tgatgatgac                                               20

<210> SEQ ID NO 82
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
agcagctgtg ccgggccag                                                19

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
cacaggctca gtcgcggatc                                               20

<210> SEQ ID NO 84
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
gcgagacttt aggtgtgcat c                                              21

<210> SEQ ID NO 85
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
gatccatgcc cgctgggatg                                                20

<210> SEQ ID NO 86
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
acgacctccg gatccaactg                                                20

<210> SEQ ID NO 87
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
cacttccttc gtggacgcc                                                 19

<210> SEQ ID NO 88
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
ccgcatctcc tccgtcctg                                                 19

<210> SEQ ID NO 89
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
cctgtgcctc acacagactc                                                20

<210> SEQ ID NO 90
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
gaagctctcg tggactactt g                                            21

<210> SEQ ID NO 91
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
agaggccgat gaagccgtag                                              20

<210> SEQ ID NO 92
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
gacagtatgc tgatgcttct tg                                           22

<210> SEQ ID NO 93
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
cggatgcagg aggatcctag                                              20

<210> SEQ ID NO 94
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94
cgaccttgcc agatgtttga c                                            21

<210> SEQ ID NO 95
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
tcagagctct cctatctgga c                                            21
```

<210> SEQ ID NO 96
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
gaatatggag ccctgggcag                                              20

<210> SEQ ID NO 97
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
gcgaaggaag tgctggagtc                                              20

<210> SEQ ID NO 98
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
caaagtactg gggttacagg tg                                           22

<210> SEQ ID NO 99
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
gtttcttgaa agggccagac ac                                           22

<210> SEQ ID NO 100
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
ggatgaacct ttaagacatc atc                                          23

<210> SEQ ID NO 101
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 101
cagcaacagc acccagcttg                                        20

<210> SEQ ID NO 102
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
ggacgagtta acttccttaa tttc                                   24

<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
cacaggctca gtcgcggatc                                        20

<210> SEQ ID NO 104
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
gtttcttcgc ggaacctggt ttaacttc                               28